United States Patent
Carter et al.

(10) Patent No.: US 11,230,538 B2
(45) Date of Patent: Jan. 25, 2022

(54) HERBICIDES

(71) Applicant: SYNGENTA PARTICIPATIONS AG, Basel (CH)

(72) Inventors: Neil Brian Carter, Bracknell (GB); Emma Briggs, Bracknell (GB); Christiana Kitsiou, Bracknell (GB); Kenneth Ling, Bracknell (GB); James Alan Morris, Bracknell (GB); Joseph Andrew Tate, Bracknell (GB); Jeffrey Steven Wailes, Bracknell (GB); John Williams, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 231 days.

(21) Appl. No.: 16/087,074

(22) PCT Filed: Mar. 16, 2017

(86) PCT No.: PCT/EP2017/056291
§ 371 (c)(1),
(2) Date: Sep. 20, 2018

(87) PCT Pub. No.: WO2017/162524
PCT Pub. Date: Sep. 28, 2017

(65) Prior Publication Data
US 2019/0330179 A1    Oct. 31, 2019

(30) Foreign Application Priority Data
Mar. 23, 2016    (GB) ..................... 1604970

(51) Int. Cl.
| | | |
|---|---|---|
| C07D 401/04 | (2006.01) | |
| C07D 401/14 | (2006.01) | |
| C07D 409/14 | (2006.01) | |
| C07D 417/14 | (2006.01) | |
| A01N 43/40 | (2006.01) | |
| A01N 43/54 | (2006.01) | |
| A01N 43/78 | (2006.01) | |
| A01N 53/00 | (2006.01) | |

(52) U.S. Cl.
CPC ........... *C07D 401/04* (2013.01); *A01N 43/40* (2013.01); *A01N 43/54* (2013.01); *A01N 43/78* (2013.01); *C07D 401/14* (2013.01); *C07D 409/14* (2013.01); *C07D 417/14* (2013.01); *A01N 53/00* (2013.01)

(58) Field of Classification Search
None
See application file for complete search history.

(56) References Cited

U.S. PATENT DOCUMENTS

| | | |
|---|---|---|
| 9,708,295 B2 * | 7/2017 | Xiao .................. C07F 9/65583 |
| 2013/0005574 A1 | 1/2013 | Epp et al. |
| 2014/0274703 A1 | 9/2014 | Eckelbarger et al. |

FOREIGN PATENT DOCUMENTS

| | | | | |
|---|---|---|---|---|
| EP | 0537423 A1 | 4/1993 | | |
| JP | 2014208631 | * 11/2014 | | |
| JP | 2014208631 A | 11/2014 | | |
| RU | 2065861 C1 | 8/1996 | | |
| WO | 2009/138712 A2 | 11/2009 | | |
| WO | 2015/052076 A1 | 4/2015 | | |
| WO | WO-2015094118 A1 * | 6/2015 | ........... | C07D 471/04 |
| WO | WO-2015187094 A1 * | 12/2015 | ........... | C07D 401/14 |
| WO | 2017162522 A1 | 9/2017 | | |

OTHER PUBLICATIONS

Christian Harcken, et al., Journal of Medicinal Chemistry, Identification of Highly Efficacious Glucocorticoid Receptor Agonists with a Potential for Reduced Clinical Bone Side Effects, 2014, 57(4), 1583-1598.
Great Britain Search Report for Great Britain Application No. 1604970.2 searched Jan. 5, 2017.
International Search Report for PCT/EP2017/056291 dated May 11, 2017.
Belikov V. G., Pharmacevticeskaa himia [Pharmaceutical Chemistry]—Textbook. Moscow: MEDpress-inform, 2007, pp. 27-29.
Gruzdev G. S. (Ed.) Himiceska zasita rastenij [Chemical protection of plants] (3rd ed.). Moscow: Agropromizdat, 1987, Chapter 8 pp. 297-298.

* cited by examiner

*Primary Examiner* — Alton N Pryor
(74) *Attorney, Agent, or Firm* — BakerHostetler; Toni-Junell Herbert

(57) ABSTRACT

The present invention relates to herbicidally active pyridino-/pyrimidino-pyridine derivatives. The invention further provides processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

17 Claims, No Drawings

HERBICIDES

CROSS-REFERENCE TO RELATED APPLICATIONS

This application is a 371 National Stage application of International Application No. PCT/EP2017/056291, filed Mar. 16, 2017, which claims priority to Great Britain Patent Application No. 1604970.2 filed Mar. 23, 2016, the entire contents of which applications are hereby incorporated by reference.

The present invention relates to herbicidally active pyridino-/pyrimidino-pyridine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

Certain pyrido-pyridine and pyrimidino-pyridine derivatives are known from JP2014-208631, where they are stated to have activity as insecticidal agents, and in particular miticidal agents.

The present invention is based on the finding that pyridino-pyridine, and pyrimidino-pyridine, derivatives of Formula (I) as defined herein, exhibit surprisingly good herbicidal activity. Thus, according to the present invention there is provided a compound of Formula (I)

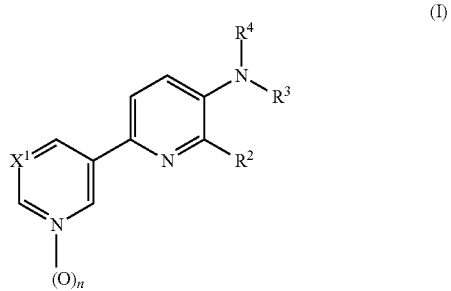

(I)

or a salt or N-oxide thereof, wherein, $X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)O$C_1$-$C_6$alkyl, —S(O)$_p$$C_1$-$C_6$alkyl, $NR^6R^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)O$C_1$-$C_6$alkyl, —S(O)$_p$($C_1$-$C_6$alkyl), $C_1$-$C_6$alkoxy and $C_1$-$C_6$haloalkoxy;

$R^3$ is —C(O)$R^9$;

$R^4$ is selected from the group consisting of hydrogen, $C_1$-$C_6$alkyl, $C_1$-$C_6$haloalkyl, $C_3$-$C_6$alkenyl, $C_3$-$C_6$alkynyl, $C_r$alkoxy$C_s$alkyl, —$C_r$alkoxy$C_s$haloalkyl, $C_r$alkoxy$C_s$thioalkyl, —C(O)$R^9$ and —$(CR^aR^b)_qR^5$;

each $R^a$ is independently hydrogen or $C_1$-$C_2$ alkyl;
each $R^b$ is independently hydrogen or $C_1$-$C_2$ alkyl;
$R^c$ is hydrogen or $C_1$-$C_4$alkyl;
$R^5$ is —C(O)O$C_1$-$C_6$alkyl, —$C_3$-$C_6$cycloalkyl, cyano, —$NR^6R^7$, —C(O)$NR^aR^b$, —S(O)$_p$($R^{11}$)$_n$, -aryl or -heteroaryl wherein said aryl and heteroaryl are optionally substituted by 1 to 3 independent $R^8$;

$R^6$ and $R^7$ are independently selected from the group consisting of hydrogen and $C_1$-$C_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and S(O)$_p$($C_1$-$C_6$alkyl);

each $R^9$ is independently selected from the group consisting of hydrogen, $C_1$-$C_6$alkyl, $C_r$alkoxy$C_s$alkyl, $C_1$-$C_6$haloalkyl, $C_r$alkoxy$C_s$haloalkyl, $C_2$-$C_6$alkenyl, $C_2$-$C_6$alkynyl, and —$(CR^aR^b)_qR^{10}$;

or $R^4$ and $R^9$ together with the atoms to which they are joined form a 5-7 membered ring system containing from 1 to 3 heteroatoms, wherein at least one heteratom is N, and any additional heteroatom is independently selected from S, O and N;

$R^{10}$ is —C(O)O$R^c$, —OC(O)$R^c$, —$C_3$-$C_6$cycloalkyl, or an -aryl, -aryloxy, -heteroaryl, -heteroaryloxy or -heterocyclyl ring, wherein said ring is optionally substituted by 1 to 3 independent $R^8$;

each n is independently 0 or 1;
p is 0, 1, or 2;
each q is independently 0, 1, 2, 3, 4, 5 or 6;
r is 1, 2, 3, 4, or 5, s is 1, 2, 3, 4, or 5, and the sum of r+s is less than or equal to 6; and
$R^{11}$ is $C_1$-$C_6$alkyl.

Compounds of formula (I) may exist as different geometric isomers, or in different tautomeric forms. This invention covers the use of all such isomers and tautomers, and mixtures thereof in all proportions, as well as isotopic forms such as deuterated compounds.

It may be the case that compounds of formula (I) may contain one or more asymmetric centers and may thus give rise to optical isomers and diastereomers. While shown without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$ alkyl groups (except where already defined more narrowly), but are preferably $C_1$-$C_4$ alkyl or $C_1$-$C_3$ alkyl groups, and, more preferably, are $C_1$-$C_2$ alkyl groups (such as methyl).

Alkenyl and alkynyl moieties can be in the form of straight or branched chains, and the alkenyl moieties, where appropriate, can be of either the (E)- or (Z)-configuration. Alkenyl and alkynyl moieties can contain one or more double and/or triple bonds in any combination; but preferably contain only one double bond (for alkenyl) or only one triple bond (for alkynyl).

The alkenyl or alkynyl moieties are typically $C_2$-$C_4$ alkenyl or $C_2$-$C_4$ alkynyl, more specifically ethenyl (vinyl), prop-2-enyl, prop-3-enyl (allyl), ethynyl, prop-3-ynyl (propargyl), or prop-1-ynyl. Preferably, the term cycloalkyl refers to cyclopropyl, cyclobutyl, cyclopentyl or cyclohexyl.

In the context of the present specification the term "aryl" preferably means phenyl.

Heteroaryl groups and heteroaryl rings (either alone or as part of a larger group, such as heteroaryl-alkyl-) are ring systems containing at least one heteroatom and can be in mono- or bi-cyclic form. Preferably, single rings will contain 1, 2 or 3 ring heteroatoms selected independently from nitrogen, oxygen and sulfur. Typically "heteroaryl" is as used in the context of this invention includes furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, and triazinyl rings, which may or may not be substituted as described herein.

The term "heterocyclyl" as used herein, encompasses ring systems containing at least one heteroatom and that are typically in monocyclic form. Preferably, heterocyclyl groups will contain up to two heteroatoms which will preferably be chosen from nitrogen, oxygen and sulfur. Where a heterocycle contains sulfur as a heteroatom it may be in oxidized form i.e. in the form —S(O)$_p$— where p is an integer of 0, 1 or 2 as defined herein. Such heterocyclyl groups are preferably 3- to 8-membered, and more preferably 3- to 6-membered rings. Examples of heterocyclic groups include oxetanyl, thietanyl, and azetidinyl groups. Such heterocylylic rings may or may not be substituted as described herein.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$ alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$ alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$ alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Compounds of formula (I) may form, and/or be used as, agronomically acceptable salts with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used in salt formation, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

Compounds of formula (I) may also form (and/or be used as) agronomically acceptable salts with various organic and/or inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when the compound of formula (I) contains a basic moiety.

Where appropriate compounds of formula (I) may also be in the form of/used as an N-oxide.

Compounds of formula (I) may also be in the form of/used as hydrates which may be formed during the salt formation.

Preferred values of $X^1$, $R^1$, $R^2$, $R^3$, $R^4$, $R^5$, $R^6$, $R^7$, $R^8$, $R^9$, $R^{10}$, $R^{11}$, $R^a$, $R^b$, $R^c$, n, p, q, r, and s are as set out below, and a compound of formula (I) according to the invention may comprise any combination of said values. The skilled person will appreciate that values for any specified set of embodiments may combined with values for any other set of embodiments where such combinations are not mutually exclusive.

The skilled man will appreciate that the values or r and s in the definitions $C_r$alkoxy$C_s$alkyl, $C_r$alkoxy$C_s$thioalkyl, and $C_r$alkoxy$C_s$haloalkyl are such that the length of the carbon chain within the substituent does not exceed 6. Preferred values of r are 1, 2, or 3. Preferred values for s are 1, 2, or 3. In various embodiments r is 1, s is 1; or, r is 1, s is 2; or r is 1, s is 3; or r is 2, s is 1; r is 2, s is 2; or r is 2, s is 3; or r is 3, s is 1; or r is 3, s is 2, r is 3, s is 3. Particularly preferred substituents thus include methoxymethyl, methoxybutyl, and ethoxymethyl, as well as methylthiomethyl and ethyl thiomethyl.

In one particular embodiment of the present invention, $X^1$ is N.

In another embodiment of the present invention, $X^1$ is $CR^1$. $R^1$ is preferably halogen or cyano, more preferably fluoro, chloro or cyano.

Most preferably $X^1$ is N or CF.

Preferably $R^2$ is halogen, cyano, $C_1$-$C_6$alkyl or $C_1$-$C_6$haloalkyl. More preferably $R^2$ is cyano, methyl or trifluoromethyl, Even more preferably $R^2$ is methyl or trifluoromethyl. Most preferably $R^2$ is trifluoromethyl.

Examples of preferred $R^3$ groups for use in the invention may be derived from the preferences for $R^9$ and the definitions therein. Particularly preferred $R^3$ groups are as defined within Table 1 below. Preferably $R^4$ is selected from the group consisting of hydrogen, $C_1$-$C_4$alkyl, $C_3$-$C_6$alkenyl, $C_r$alkoxy$C_s$alkyl, $C_r$alkylthio$C_s$alkyl, $C_3$-$C_6$alkynyl, $C_1$-$C_3$haloalkyl, $C_r$alkoxy$C_s$haloalkyl, —C(O)$R^9$, and $(CR^aR^b)_qR^5$. In such embodiments where $R^4$ is —C(O)$R^9$, it is preferred that $R^9$ is $C_1$-$C_3$alkyl, $C_2$-$C_4$alkenyl, or —$(CR^aR^b)_qR^1$. More preferably when $R^4$ is —C(O)$R^9$, $R^9$ is hydrogen, -methyl, ethyl, propyl, butenyl, or —(CH$_2$)$_2$C(O)OR$^c$.

Where $R^4$ is $(CR^aR^b)_qR^5$, in one set of embodiments, q is 1, 2, or 3; $R^a$ and $R^b$ are independently hydrogen, methyl or ethyl (preferably hydrogen), and $R^5$ is —C(O)NR$^a$R$^b$, —NR$^6$R$^7$, cyano, or —$C_3$-$C_6$cycloalkyl (e.g. cyclopropyl), -aryl (e.g. phenyl) or -heteroaryl (in particular a 5- or 6-membered heteroaryl, such as for example, thiazolyl, pyridyl, pyrimidinyl, pyridazinyl, pyrazinyl, or triazinyl ring), wherein said aryl and heteroaryl are optionally substituted by 1 to 3 independent $R^8$.

In such embodiments where $R^5$ is —C(O)NR$^a$R$^b$, $R^a$ and $R^b$ are preferably independently hydrogen, methyl or ethyl (more preferably methyl).

Where $R^5$ is an optionally substituted heteroaryl ring, it is particularly preferred that said ring is a pyridyl or thiazolyl ring.

In an alternative embodiment of the present invention, $R^4$ and $R^9$ together with the atoms to which they are joined form a 5-7 membered ring system containing from 1 to 3 heteroatoms, wherein at least one heteroatom is N, and any additional heteroatom is independently selected from S, O and N. Preferably said ring system is a 5- or 6-membered N-linked heterocyclic ring system, and more preferably it is a pyrrolidinone, pyrrolidinedione or piperidinone ring. The skilled man will appreciate that the $R^9$ in these embodiments derives from $R^3$.

Preferably each $R^a$ is independently hydrogen, methyl or ethyl, more preferably hydrogen or methyl.

Preferably each $R^b$ is independently hydrogen, methyl or ethyl, more preferably hydrogen or methyl.

Preferably each q is independently 0, 1, 2 or 3. The skilled man will appreciate that if q is 0 when $R^4$ is $(CR^aR^b)_qR^5$, then $R^4$ is equivalent to $R^5$. Similarly if q is 0 when $R^9$ is $(CR^aR^b)_qR^{10}$, then $R^9$ is equivalent to $R^{10}$.

Preferably each $R^c$ is hydrogen, methyl or ethyl.

In one particular embodiment $R^6$ and $R^7$ are both hydrogen. In another embodiment $R^6$ is hydrogen and $R^1$ is $C_1$-$C_6$alkyl (e.g., methyl or ethyl). In another embodiment, $R^6$ and $R^7$ are both $C_1$-$C_6$alkyl, in particular both methyl or both ethyl.

Where an aryl, aryloxy, heteroaryl, heteroaryloxy, or heterocyclic ring system is substituted by 1 to 3 independent $R^8$ as described herein, it is preferred that such ring system is substituted by 1 or 2 independent $R^8$, more preferably by 1 $R^8$. Preferably each $R^8$ is independently selected from halogen or $C_1$-$C_3$ alkyl, $C_1$-$C_3$haloalkyl. More preferably each $R^8$ is independently fluoro, chloro or methyl.

Preferably $R^9$ is $C_1$-$C_6$alkyl [preferably methyl, ethyl, propyl (in particular iso-propyl) or butyl (in particular tert-butyl)], $C_1$-$C_3$haloalkyl, $C_1$-$C_3$alkoxy$C_1$-$C_3$alkyl or $(CR^aR^b)_qR^1$.

$R^{10}$ is preferably —C(O)OR$^c$, —OC(O)R$^c$, cyclopropyl, cyclobutyl, cyclopentyl, cyclohexyl, or a ring system selected from phenyl, phenoxy, pyridinyl, pyrimidinyl, thiazolyl, and thiophenyl, wherein said ring system is optionally substituted by 1-3 independent $R^8$.

Table 1 below provides 115 specific examples of herbicidal compounds of Formula (I) for use according to the invention.

TABLE 1

Specific examples of compounds of Formula (I)

| Entry No | $X^1$ | $R^2$ | $R^3$ | $R^4$ |
|---|---|---|---|---|
| C1 | C-F | $CH_3$ | $C(O)CH(CH_3)_2$ | $C(O)CH(CH_3)_2$ |
| C2 | N | $CH_3$ | $C(O)CH(CH_3)_2$ | H |
| C3 | C-F | $CH_3$ | $C(O)CH(CH_3)_2$ | H |
| C4 | C-F | $CF_3$ | $C(O)CH(CH_3)_2$ | $CH_3$ |
| C5 | C-F | $CF_3$ | $C(O)CH_3$ | $C(O)CH_3$ |
| C6 | N | $CF_3$ | $C(O)CH_3$ | $C(O)CH_3$ |
| C7 | N | $CF_3$ | $C(O)CH_3$ | H |
| C8 | N | $CF_3$ | $C(O)CH(CH_3)_2$ | H |
| C9 | C-F | $CF_3$ | $C(O)CH_3$ | H |
| C10 | C-F | $CF_3$ | $C(O)CH(CH_3)_2$ | H |
| C11 | C-CN | $CF_3$ | $C(O)CH(CH_3)_2$ | H |
| C12 | C-Cl | $CF_3$ | $C(O)CH(CH_3)_2$ | H |
| C13 | C-F | $CF_3$ | $C(O)CH_2CH_3$ | H |
| C14 | C-F | $CF_3$ | $C(O)Ph$ | H |
| C15 | C-F | $CF_3$ | $C(O)CH_2CH_3$ | $CH_3$ |
| C16 | C-F | $CF_3$ | $C(O)CH(CH_3)_2$ | $CH_2CH=CH_2$ |
| C17 | N | $CF_3$ | $C(O)Ph$ | H |
| C18 | N | $CF_3$ | $C(O)CH_2CH_3$ | H |
| C19 | C-F | $CF_3$ | $C(O)CH_2cyclohexyl$ | H |
| C20 | C-F | $CF_3$ | $C(O)cyclohexyl$ | H |
| C21 | C-F | $CF_3$ | $C(O)cyclobutyl$ | H |
| C22 | C-F | $CF_3$ | $C(O)CH_2CH_2CH_3$ | H |
| C23 | C-F | $CF_3$ | $C(O)CH=CHCH_3$ (E) | H |
| C24 | C-F | $CF_3$ | $C(O)CH_2CH_2OCH_3$ | H |
| C25 | C-F | $CF_3$ | $C(O)CH_2cyclopentyl$ | H |
| C26 | C-F | $CF_3$ | $C(O)CHCl_2$ | H |
| C27 | C-F | $CF_3$ | $C(O)CH_2OCH_3$ | H |
| C28 | C-F | $CF_3$ | $C(O)CH_2Ophenyl$ | H |
| C29 | C-F | $CF_3$ | $C(O)CCl_3$ | H |
| C30 | C-F | $CF_3$ | $C(O)p$-toluene | H |
| C31 | C-F | $CF_3$ | $C(O)$-2,6-di-F-Ph | H |
| C33 | C-F | $CF_3$ | $C(O)$-2,4,5-tri-F-Ph | H |
| C34 | C-F | $CF_3$ | $C(O)t$-Bu | H |
| C35 | C-F | $CF_3$ | $C(O)CH_2Cl$ | H |
| C36 | C-F | $CF_3$ | $C(O)C(CH_3)_2OC(O)CH_3$ | H |
| C37 | C-F | $CF_3$ | $C(O)CH=C(CH_3)_2$ | H |
| C38 | C-F | $CF_3$ | $C(O)CH=C(CH_3)_2$ | $C(O)CH=C(CH_3)_2$ |
| C39 | C-F | $CF_3$ | $C(O)CH_2CH_3$ | $CH_2CH=CH_2$ |
| C42 | C-F | $CF_3$ | $C(O)CH_2CO_2CH_2CH_3$ | H |
| C44 | C-F | $CF_3$ | $C(O)CH_2CH_3$ | $C(O)CH_2CH_3$ |
| C45 | C-F | $CF_3$ | $C(O)$-pyridin-2-yl | H |
| C46 | C-F | $CF_3$ | $C(O)$-2-F-Ph | H |
| C47 | C-F | $CF_3$ | $C(O)$-thiophen-2-yl | H |
| C49 | C-F | $CF_3$ | $C(O)CH_2CH_2CH_3$ | H |
| C50 | C-F | $CF_3$ | $C(O)$-pyridin-3-yl | H |
| C51 | C-F | $CF_3$ | $C(O)$-3-$CH_3$-thiophen-2-yl | H |
| C52 | C-F | $CF_3$ | $C(O)$-5-$CH_3$-thiophen-2-yl | H |
| C53 | C-F | $CF_3$ | $C(O)CH_2CH_2cyclopentyl$ | H |
| C54 | C-F | $CF_3$ | 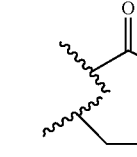 | |
| C55 | C-F | $CF_3$ | 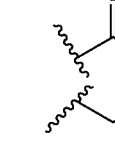 | |
| C56 | C-F | $CF_3$ | $C(O)CH_2CF_3$ | H |
| C57 | C-F | $CF_3$ | $C(O)CH_2CH_3$ | $CH_2CN$ |
| C58 | C-F | $CF_3$ | $C(O)CH(CH_3)_2$ | $CH_2CN$ |
| C59 | C-F | $CF_3$ | $C(O)cyclopropyl$ | H |
| C60 | N | $CF_3$ | $C(O)CCl_3$ | H |
| C61 | C-F | $CF_3$ | $C(O)CH(CH_3)_2$ | $CH_2CCH$ |
| C62 | C-F | $CF_3$ | $C(O)CH_2CH_3$ | $CH_2CH_2CHF_2$ |
| C63 | C-F | $CF_3$ | $C(O)CH_2OCH_3$ | $CH_2CH=CH_2$ |
| C65 | N | $CF_3$ | $C(O)CHCl_2$ | H |
| C66 | C-F | $CF_3$ | $C(O)CH_2cyclopropyl$ | H |
| C67 | C-F | $CF_3$ | 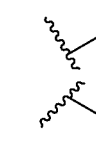 | |
| C68 | C-F | $CF_3$ | $C(O)CCl_3$ | $CH_3$ |
| C69 | C-F | $CF_3$ | $C(O)CH(CH_3)_2$ | $(CH_2)_3N(CH_2CH_3)_2$ |

TABLE 1-continued

Specific examples of compounds of Formula (I)

| Entry No | $X^1$ | $R^2$ | $R^3$ | $R^4$ |
|---|---|---|---|---|
| C70 | C-F | $CF_3$ | $C(O)CH_2CH_3$ | 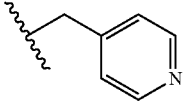 [SMILES: *Cc1ccncc1] |
| C71 | C-F | $CF_3$ | $C(O)CH_2CH_3$ | $CH_2C(O)N(CH_3)_2$ |
| C72 | C-F | $CF_3$ | $C(O)CH_2CH_3$ | $CH_2OCH_2CF_3$ |
| C73 | C-F | $CF_3$ | $C(O)CH_2CH_3$ | $CH_2CH=C(CH_3)_2$ |
| C74 | C-F | $CF_3$ | $C(O)Ph$ | $(CH_2)_3N(CH_2CH_3)_2$ |
| C75 | C-F | $CF_3$ | $C(O)Ph$ | $CH_2CH(CH_3)_2$ |
| C76 | C-F | $CF_3$ | $C(O)Ph$ | $CH_2OCH_2C(CH_3)_3$ |
| C77 | C-F | $CF_3$ | $C(O)Ph$ | 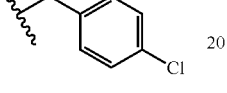 |
| C78 | C-F | $CF_3$ | $C(O)Ph$ | 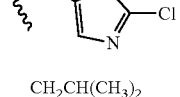 |
| C79 | C-F | $CF_3$ | $C(O)CH_2OCH_3$ | $CH_2CH(CH_3)_2$ |
| C80 | C-F | $CF_3$ | $C(O)CH_2OCH_3$ | $CH_2$cyclopropyl |
| C81 | C-F | $CF_3$ | $C(O)CH_2OCH_3$ | $CH_2OCH_2C(CH_3)_3$ |
| C82 | C-F | $CF_3$ | $C(O)CH_2OCH_3$ | 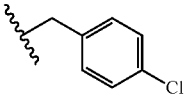 [SMILES: *Cc1ccc(Cl)cc1] |
| C83 | C-F | $CF_3$ | $C(O)CH_2OCH_3$ | 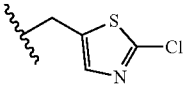 [SMILES: *Cc1cnc(Cl)s1] |
| C84 | C-F | $CF_3$ | $C(O)CH_2OCH_3$ | $CH_2C(O)N(CH_3)_2$ |
| C85 | C-F | $CF_3$ | $C(O)CH(CH_3)_2$ | $CH_2CH_2OCH_3$ |
| C86 | C-F | $CF_3$ | $C(O)CH(CH_3)_2$ | $CH_2CH(CH_3)_2$ |
| C87 | C-F | $CF_3$ | $C(O)CH(CH_3)_2$ | $CH_2$cyclopropyl |
| C88 | C-F | $CF_3$ | $C(O)CH(CH_3)_2$ | $CH_2CH_2SCH_3$ |
| C89 | C-F | $CF_3$ | $C(O)CH(CH_3)_2$ | $CH_2OCH_2C(CH_3)_3$ |
| C90 | C-F | $CF_3$ | $C(O)CH(CH_3)_2$ | $CH(CH_3)_2$ |
| C91 | C-F | $CF_3$ | $C(O)CH(CH_3)_2$ | 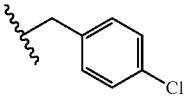 [SMILES: *Cc1ccc(Cl)cc1] |
| C92 | C-F | $CF_3$ | $C(O)CH(CH_3)_2$ | 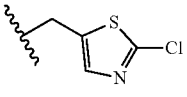 [SMILES: *Cc1cnc(Cl)s1] |
| C93 | C-F | $CF_3$ | $C(O)CH(CH_3)_2$ | $CH_2CH=C(CH_3)_2$ |
| C94 | C-F | $CF_3$ | $C(O)CH_2CH_3$ | $CH_2CCH$ |
| C95 | C-F | $CF_3$ | $C(O)CH_2CH_3$ | $(CH_2)_3N(CH_2CH_3)_2$ |
| C96 | C-F | $CF_3$ | $C(O)CH_2CH_3$ | $CH_2CH_2OCH_3$ |
| C97 | C-F | $CF_3$ | $C(O)CH_2CH_3$ | $CH_2CH(CH_3)_2$ |
| C98 | C-F | $CF_3$ | $C(O)CH_2CH_3$ | $CH_2CH_2SCH_3$ |
| C99 | C-F | $CF_3$ | $C(O)CH_2CH_3$ | $CH_2OCH_2C(CH_3)_3$ |
| C100 | C-F | $CF_3$ | $C(O)CH_2CH_3$ | $CH(CH_3)_2$ |
| C101 | C-F | $CF_3$ | $C(O)CH_2CH_3$ | 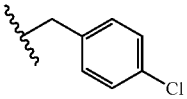 |
| C102 | C-F | $CF_3$ | $C(O)CH_2CH_3$ | 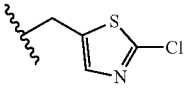 [SMILES: *Cc1cnc(Cl)s1] |
| C103 | C-F | $CF_3$ | $C(O)Ph$ | $CH_2$cyclopropyl |
| C104 | C-F | $CF_3$ | $C(O)Ph$ | $CH_2CH_2SCH_3$ |
| C105 | C-F | $CF_3$ | $C(O)Ph$ | $CH_2C(O)N(CH_3)_2$ |
| C106 | C-F | $CF_3$ | $C(O)CH_2OCH_3$ | $CH_2CH=C(CH_3)_2$ |
| C107 | C-F | $CF_3$ | $C(O)CH(CH_3)_2$ | $CH_2C(O)N(CH_3)_2$ |
| C108 | C-F | $CF_3$ | $C(O)CH_2CH_3$ | $CH_2$cyclopropyl |
| C109 | N | $CF_3$ | $C(O)$cyclopropyl | H |
| C110 | N | $CF_3$ | 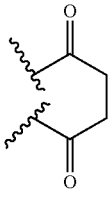 | |
| C111 | C-F | $CF_3$ | $C(O)$cyclopentyl | H |
| C112 | C-F | $CF_3$ | $C(O)H$ | H |
| C113 | C-F | $CF_3$ | $C(O)CH_2CH_2CO_2H$ | H |
| C114 | C-F | CN | $C(O)CH_2OCH_3$ | H |
| C115 | C-F | CN | $C(O)CH_2CH_3$ | H |
| C116 | N | CN | $C(O)CH_2CH_3$ | H |
| C117 | C-F | $CF_3$ | 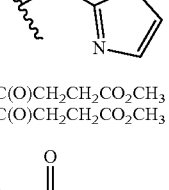 | H |
| C118 | C-F | $CF_3$ | $C(O)CH_2CH_2CO_2CH_3$ | H |
| C119 | C-F | $CF_3$ | $C(O)CH_2CH_2CO_2CH_3$ | $C(O)CH_2CH_2CO_2CH_3$ |
| C120 | C-F | $CF_3$ | 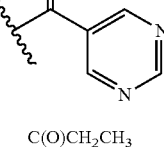 | H |
| C121 | C-F | $CF_3$ | $C(O)CH_2CH_3$ | $C(O)CH_2CH_3$ |

Compounds of Formula (I) may be prepared according to the following schemes, in which the substituents $X^1$, $R^1$, $R^2$, $R^3$, $R^4$, $R^5$, $R^6$, $R^7$, $R^8$, $R^9$, $R^{10}$, $R^{11}$, $R^a$, $R^b$, $R^c$, n, p, q, r, and s have (unless otherwise stated explicitly) the definitions described hereinbefore, using techniques known to the person skilled in the art of organic chemistry. General methods for the production of compounds of formula (I) are described below. The starting materials used for the preparation of the compounds of the invention may be purchased from the usual commercial suppliers or may be prepared by known methods. The starting materials as well as the intermediates may be purified before use in the next step by state of the art methodologies such as chromatography, crystallization, distillation and filtration.

Typical abbreviations used throughout are as follows:
Ac=acetyl
app=apparent
BINAP=2,2'-bis(diphenylphosphino)-1,1'-binaphthyl
br.=broad
$^t$Bu=tert-butyl t-BuOH=tert-butanol
d=doublet
dd=double doublet
Dba=dibenzylideneacetone
DCM=dichloromethane
DMF=N, N-dimethylformamide
DMSO=dimethylsulfoxide
DPPA=diphenylphosphoryl azide
Et₃N=triethylamine
Et₂O=diethyl ether
EtOAc=ethyl acetate
EtOH=ethanol
m=multiplet
mCPBA=meta-chloro-perbenzoic acid
Me=methyl
MeOH=methanol
Ms=mesylate
Ph=phenyl
q=quartet
RT=room temperature
s=singlet
t=triplet
Tf=triflate
TFA=trifluoroacetic acid
THF=tetrahydrofuran
TMS=tetramethylsilane
tr=retention time Processes for preparation of compounds of the present invention, which optionally can be in the form of an agrochemically acceptable salt, are now described, and form further aspects of the present invention.

Formula Ia

Compounds of Formula Ia are compounds of Formula I where $R^3$ is $COR^9$, compounds of Formula Ib are compounds of Formula I where both $R^3$ and $R^4$ are $COR^9$.

Formula I

Formula Ic

A compound of Formula Ic, which is a compound of Formula I where n=1, may be prepared from a compound of Formula I where n=0 via reaction with a suitable oxidant in a suitable solvent. Suitable oxidants may include 3-chloroperbenzoic acid (see for example UCB Pharma WO2012032334). Suitable solvents may include DCM.

Formula A + Formula B → Formula Ia

A compound of Formula Ia may be prepared from a compound of Formula A via an amide formation reaction with a compound of Formula B in the presence of a suitable base (where $LG^1$ is a suitable activated leaving group such as F, Cl or pentafluorophenol) optionally (when $LG^1$ is OH or OR) in the presence of a suitable amide coupling reagent and in a suitable solvent. Suitable bases include pyridine or triethylamine. Suitable amide coupling reagents include 1-propanephosphonic acid cyclic anhydride (see for example Vertex Pharmaceuticals Inc, WO2010/048564). Suitable solvents include DCM, DCE, THF or Me-THF. Compounds of formula B are commercially available or may be prepared by methods well known in the literature.

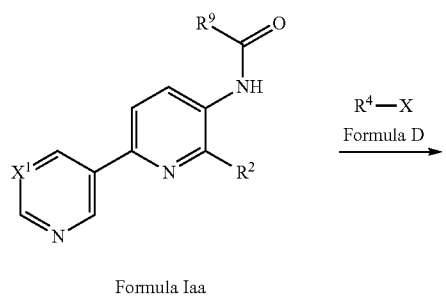

Formula Iaa

Formula Ia

In an alternative approach, a compound of Formula Ia may be prepared from a compound of Formula Iaa (a compound of formula I where $R^4$ is hydrogen) via an alkylation reaction with a compound of Formula D in the presence of a suitable base and in a suitable solvent. Suitable bases include sodium hydride (see for example Bioorg. Med. Chem. Lett. (2010) 4911). Suitable solvents include THF or DMF. Compounds of Formula D are commercially available or may be prepared by methods well known in the literature.

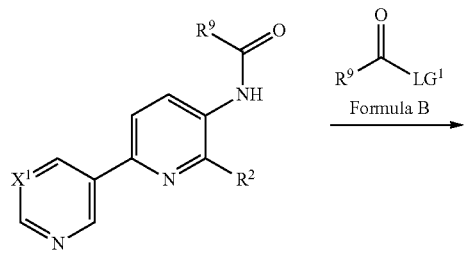

Formula Iaa

Formula Ib

A compound of Formula Ib may be prepared from a compound of Formula Iaa via an amide formation reaction with a compound of Formula B, in the presence of a suitable base (when $LG^1$ is a suitable activated leaving group such as F, Cl or pentafluorophenol) and in a suitable solvent. Suitable solvents may include DCM or DCE. Compounds of formula B are commercially available or may be prepared by methods well known in the literature.

Formula E

Formula I

In an alternative approach, a compound of Formula I may be prepared from a compound of Formula E (where $Y^2$ is a suitable halogen, such as Cl, Br or I or a suitable pseudo-halogen, such as OTf) via a cross-coupling reaction with a compound of Formula F, optionally in the presence of a suitable catalyst/ligand system, optionally in the presence of a suitable base and in a suitable solvent. Suitable catalyst/ligand systems include CuI/N,N-dimethyl-1,2-diaminocyclohexane (see for example C. Enguehard-Gueiffer et al Synthesis (2015) 3983) or CuI/N-methyl-(methylamino)ethylamine (see for example Tempero Pharmaceuticals Inc WO2013/019682). Suitable bases include potassium phosphate and suitable solvents may include toluene or 1,4-dioxane. Compounds of Formula F are commercially available or may be prepared by methods well known in the literature.

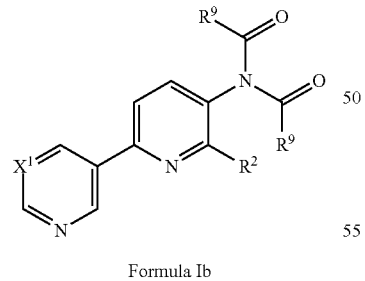

Formula G

Formula E

A compound of Formula E may be prepared from a compound of Formula G (where $Y^1$ is a suitable halogen, such as Cl or Br) via a cross-coupling reaction with a compound of Formula H (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ (see for example Vertex Pharmaceuticals Ltd. WO2011087776), Pd$_2$Cl$_2$(PPh$_3$)$_2$ (see for example Abbott Laboratories US2012245124) or [1,1'-bis(diphenylphosphino)ferrocene]dichloropalladium(II) (see for example Dow Agro Sciences US2013005574). Suitable bases may include K$_2$CO$_3$ or CsF. Suitable solvents may include ethylene glycol dimethyl ether, acetonitrile, DMF, ethanol, 1,4-dioxane and/or water. Compounds of Formula G and of Formula H are commercially available or can be prepared by methods well known in the literature.

reaction with a compound of Formula K, optionally in the presence of a suitable catalyst/ligand system and optionally in the presence of a suitable base and in a suitable solvent. Suitable catalyst/ligand systems include CuI/N,N-dimethyl-1,2-diaminocyclohexane (see for example C. Enguehard-Gueiffer et al Synthesis (2015) 3983) or CuI/N-methyl-(methylamino)ethylamine (see for example Tempero Pharmaceuticals Inc WO2013/019682). Suitable bases include potassium phosphate and suitable solvents may include toluene or 1,4-dioxane. Compounds of Formula K and of Formula L are commercially available or may be prepared by methods well known in the literature.

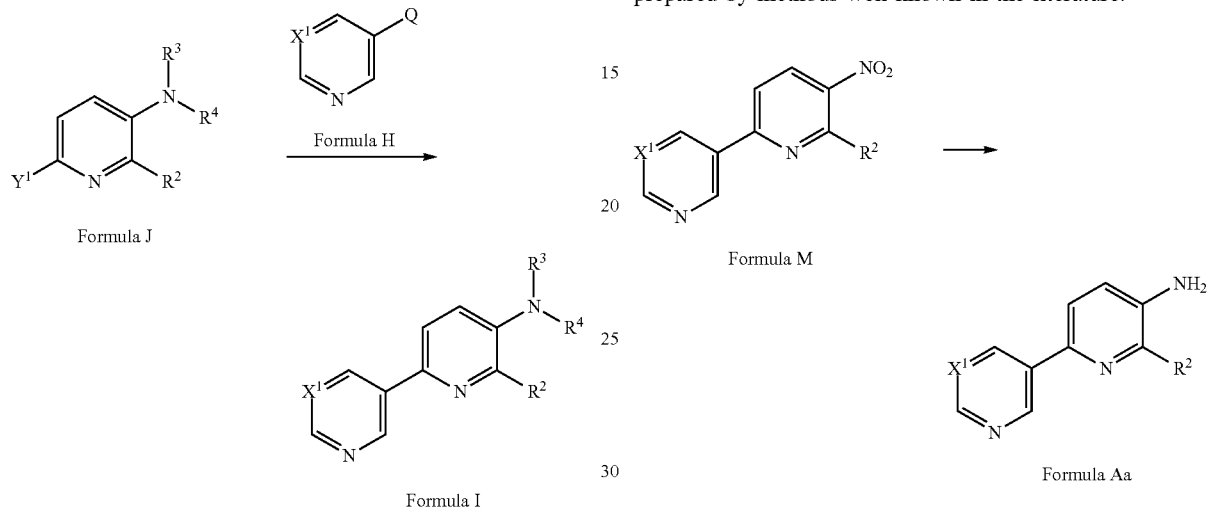

Formula J

Formula H

Formula M

Formula I

Formula Aa

In a yet further alternative approach, a compound of Formula I may be prepared from a compound of Formula J (where Y$^1$ is a suitable halogen, such as Cl, Br or I or a suitable pseudohalogen, such as OTf) via a cross-coupling reaction with a compound of Formula H (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ (see for example Vertex Pharmaceuticals Ltd. WO2011087776 or S. M. Bromidge et al J. Med. Chem. (2000) 1123), Pd$_2$Cl$_2$(PPh$_3$)$_2$ (see for example Abbott Laboratories US2012245124), [1,1'-bis(diphenylphosphino)ferrocene]dichloropalladium(I) (see for example Dow Agro Sciences US2013005574). Suitable bases may include K$_2$CO$_3$ or CsF. Suitable solvents may include ethylene glycol dimethyl ether, acetonitrile, DMF, ethanol, 1,4-dioxane and/or water. Compounds of Formula H are commercially available or can be prepared by methods well known in the literature.

A compound of Formula Aa (a compound of Formula A where R$^4$ is hydrogen) may be prepared from a compound of Formula M via a reduction reaction optionally in the presence of a suitable catalyst and/or using a suitable reducing agent in a suitable solvent. Suitable catalysts include palladium on charcoal (see for example Z. Gao et al Bioorg. Med. Chem. Lett. (2013) 6269), Raney nickel (see for example Millenium Pharmaceuticals Ltd WO2010/065134). Suitable reducing agents include hydrogen gas, Fe/HCl (see for example A. Gangee et al J. Med. Chem. (1998) 4533), SnCl$_2$ (see for example Pharmacia and Upjohn Company WO2004/099201). Suitable solvents include ethanol, methanol, ethyl acetate or water.

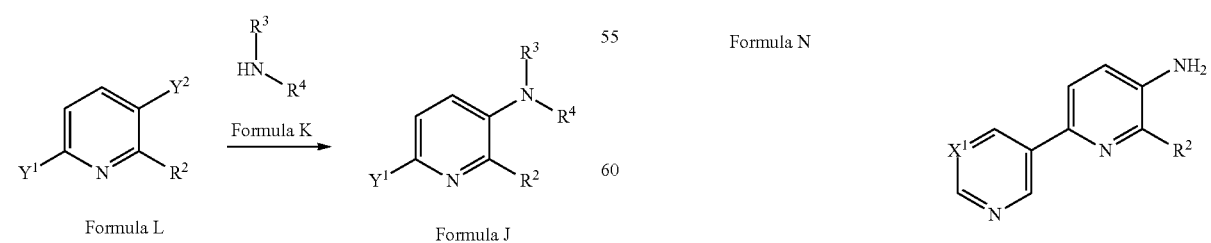

Formula L

Formula K

Formula J

Formula N

Curtius rearrangement

Formula Aa

A compound of Formula J may be prepared from a compound of Formula L (where Y$^1$ is a suitable halogen, such as Br or I or a suitable pseudohalogen, such as OTf via In an alternative approach, a compound of Formula Aa may be prepared from a compound of Formula N via a Curtius rearrangement using a suitable reagent in a suitable solvent. Suitable reagents include DPPA (see for example Takeda Pharmaceutical Company Ltd WO2008/156757) and suitable solvents include DMF or toluene.

example F. Giordanetto et al Bioorg. Med. Chem. Lett (2014), 2963), LiOH (see for example AstraZeneca AB, WO2006/073361) or KOH (see for example Kowa Co. Ltd EP1627875). Suitable solvents include $H_2O$, THF, MeOH or EtOH or mixtures thereof.

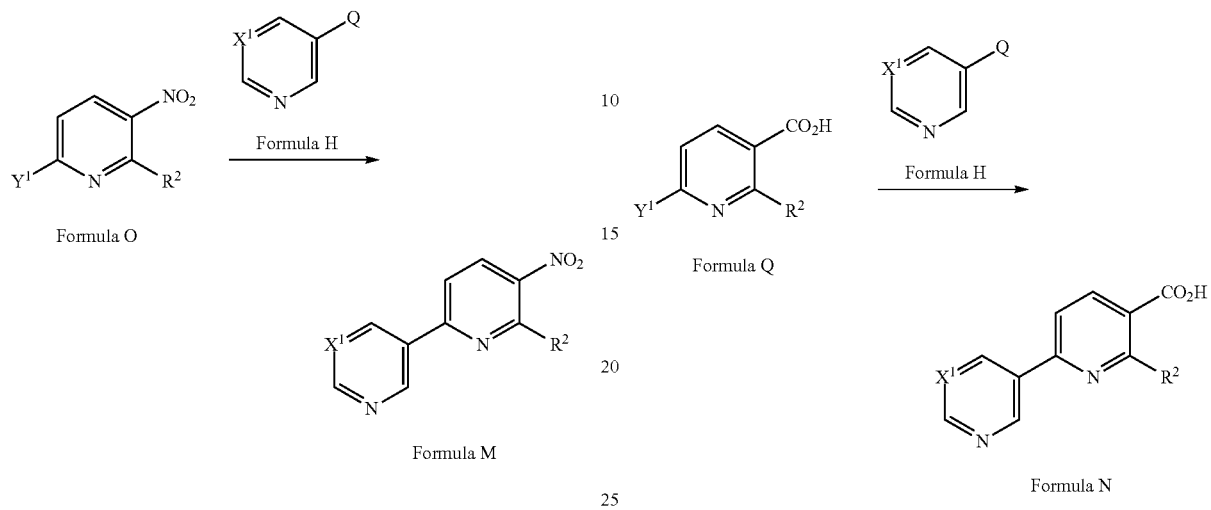

A compound of Formula M may be prepared from a compound of Formula O (where $Y^1$ is a suitable halogen, such as Cl, Br or I or suitable pseudohalogen, such as OTf) via a cross-coupling reaction with a compound of Formula H (where Q is a suitable coupling group, such as —$B(OH)_2$ or —$B(OR)_2$ or —$SnR_3$) in the presence of a suitable catalyst, optionally in the presence of a suitable base and in a suitable solvent. Suitable catalysts may include $Pd(PPh_3)_4$ (see for example A. P. Johnson et al, ACS Med. Chem. Lett. (2011) 729) or [1,1'-bis(diphenylphosphino)ferrocene]dichloropalladium(II) (see for example Laboratorios Almirall, WO2009/021696). Suitable bases may include $K_2CO_3$, $Na_2CO_3$, $Cs_2CO_3$, $K_3PO_4$ or CsF. Suitable solvents may include ethylene glycol dimethyl ether, acetonitrile, DMF, ethanol, 1,4-dioxane, tetrahydrofuran and/or water. Compounds of Formula H and of Formula O are commercially available or can be prepared by methods well known in the literature.

In an alternative approach, a compound of Formula N may be prepared from a compound of Formula Q (where $Y^1$ is a suitable halogen, such as Cl or Br) via a cross-coupling reaction with a compound of Formula H (where Q is a suitable coupling group, such as —$B(OH)_2$ or —$B(OR)_2$ or —$SnR_3$) in the presence of a suitable catalyst, optionally in the presence of a suitable base and in a suitable solvent. Suitable catalysts may include $Pd(PPh_3)_4$ (see for example Pfizer Limited WO2009/153720) or [1,1'-bis(diphenylphosphino)ferrocene]dichloropalladium(II) (see for example AstraZeneca AB, WO2009/075160). Suitable bases may include $K_2CO_3$, $Na_2CO_3$, $Cs_2CO_3$, $K_3PO_4$ or CsF. Suitable solvents may include ethylene glycol dimethyl ether, acetonitrile, DMF, ethanol, 1,4-dioxane, tetrahydrofuran and/or water. Compounds of Formula H are commercially available or can be prepared by methods well known in the literature.

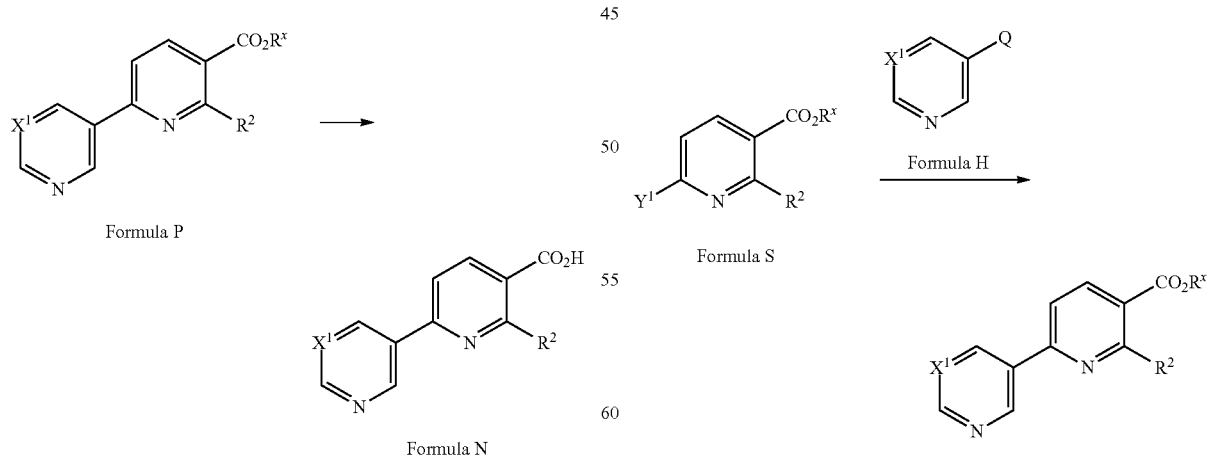

A compound of Formula N may be prepared from a compound of Formula P (where $R^x$ is $C_{1-6}$ alkyl) via a hydrolysis reaction in the presence of a suitable reagent in a suitable solvent. Suitable reagents include NaOH (see for A compound of Formula R may be prepared from a compound of Formula S (where $Y^1$ is a suitable halogen, such as Cl or Br) via a cross-coupling reaction with a compound of Formula H (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ (see for example Pfizer Limited WO2009/153720) or [1,1'-bis(diphenylphosphino)ferrocene]dichloropalladium(I) (see for example Cytokinetics Incorporated WO2008/016643). Suitable bases may include K$_2$CO$_3$, Na$_2$CO$_3$, Cs$_2$CO$_3$, K$_3$PO$_4$ or CsF. Suitable solvents may include ethylene glycol dimethyl ether, acetonitrile, DMF, ethanol, 1,4-dioxane, tetrahydrofuran and/or water. Compounds of Formula H are commercially available or can be prepared by methods well known in the literature.

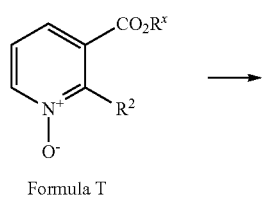

Formula T

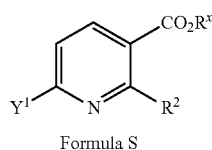

Formula S

A compound of Formula S (where Y$^1$ is a suitable halogen, such as Br or Cl) may be prepared from a compound of Formula T via a halogenation reaction using a suitable reagent, optionally in a suitable solvent. Suitable reagents may include POCl$_3$ (see for example Takeda Pharmaceutical Co. Ltd. US2011/152273). Suitable solvents may include DCM or DCE.

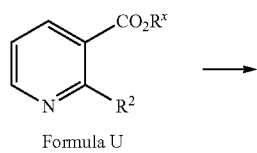

Formula U

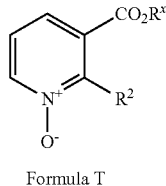

Formula T

A compound of Formula T may be prepared from a compound of Formula U via an oxidation reaction using a suitable oxidising reagent in a suitable solvent. Suitable oxidants may include 3-chloroperbenzoic acid (see for example Trius Therapeutics Inc. US2012/023875) or urea hydrogen peroxide complex/trifluoroacetic anhydride (see Takeda Pharmaceutical Co. Ltd. US2011/152273). Suitable solvents include DCM or acetonitrile. Compounds of Formula U are commercially available or can be prepared by methods well known in the literature.

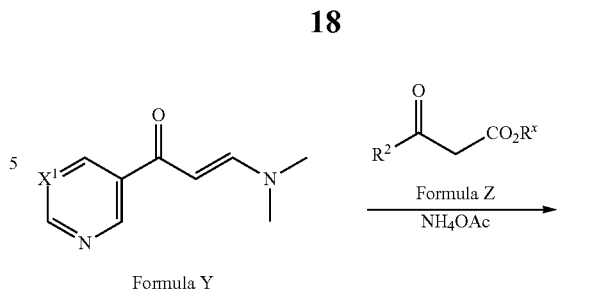

In a yet further alternative approach, compounds of Formula R may be prepared from compounds of Formula Y by reaction with compounds of Formula Z in the presence of ammonium acetate (see for example F. Hoffmann-La Roche WO2008/034579). Compounds of Formula Z are commercially available or can be prepared by methods well known in the literature.

Compounds of Formula Y may be prepared from compounds of Formula AA by reaction with dimethyl formamide dimethylacetal (see for example F. Hoffmann-La Roche WO2008/034579). Compounds of Formula AA are commercially available or can be prepared by methods well known in the literature.

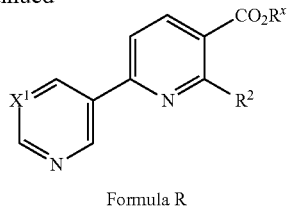

Formula R

In a yet further alternative approach, a compound of Formula R may be prepared from a compound of Formula AB via a reduction using a suitable reducing agent optionally in a suitable solvent. Suitable reducing agents include indium/ammonium chloride (see for example J. S. Yadav et al Tet. Lett (2000), 2663) or zinc/ammonium chloride. Suitable solvents may include MeOH, THF or water or combinations thereof.

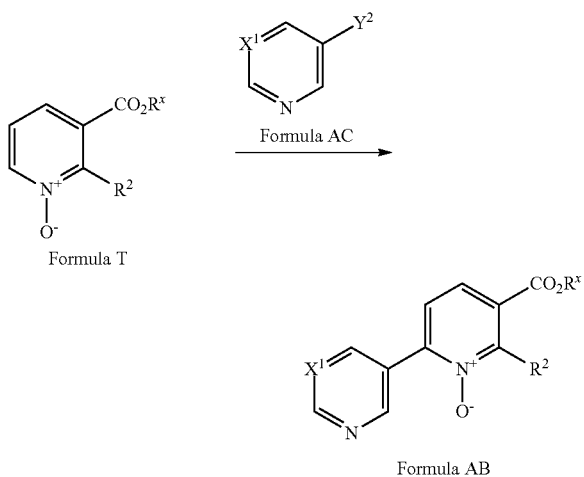

Formula T

Formula AC

Formula AB

A compound of Formula AB made be prepared from a compound of Formula T via a cross-coupling reaction with a compound of Formula AC (where $Y^2$ is a suitable halogen, such as Cl, Br or I or suitable pseudohalogen, such as OTf) in the presence of a suitable catalyst, optionally in the presence of a suitable base and in a suitable solvent. Suitable catalysts include $Pd(OAc)_2$/tri(tert-butyl)phosphonium tetrafluoroborate (see for example F. Glorius et al JACS (2013) 12204). A suitable base is $K_2CO_3$. A suitable solvent is toluene. Compounds of Formula AC are commercially available or can be prepared by methods well known in the literature.

The compounds of Formula (I) as described herein may be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound as described herein and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

Such herbicidal compositions generally comprise from 0.1 to 99% by weight, especially from 0.1 to 95% by weight of compounds of Formula (I) and from 1 to 99.9% by weight of a formulation adjuvant, which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Herbicidal compositions as described herein may further comprise at least one additional pesticide. For example, the compounds of formula (I) can also be used in combination with other herbicides or plant growth regulators. In a preferred embodiment the additional pesticide is a herbicide and/or herbicide safener. Examples of such mixtures are, in which 'I' represents a compound of Formula (I), I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfiuralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacetmethyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of formula (I) and/or compositions of the present invention may also be combined with herbicidal compounds disclosed in WO06/024820 and/or WO07/096576.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual (supra).

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) as described herein can also be used in combination with one or more safeners. Likewise, mixtures of a compound of Formula (I) as described herein with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl) amino]benzenesulfonamide.

The safeners of the compound of Formula (I) may also be in the form of esters or salts, as mentioned e.g. in The Pesticide Manual (supra). The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

As described above, compounds of formula (I) and/or compositions comprising such compounds may be used in methods of controlling unwanted plant growth, and in particular in controlling unwanted plant growth in crops of useful plants. Thus, the present invention further provides a method of selectively controlling weeds at a locus comprising crop plants and weeds, wherein the method comprises application to the locus, of a weed-controlling amount of a compound of formula (I), or a composition as described herein. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, as well as those where the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled include both monocotyledonous (e.g. grassy) species, for example: *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*; and dicotyledonous species, for example: *Abutilon, Amaranthus, Ambrosia, Chenopodium, Chrysanthemum, Conyza, Galium, Ipomoea, Kochia, Nasturtium, Polygonum, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Preferably the weeds to be controlled and/or growth-inhibited, include monocotyledonous weeds, more preferably grassy monocotyledonous weeds, in particular those from the following genus: *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crusgalli* (English name "common barnyard grass", ECHCG), *Echinochloa oryzoides, Echinochloa colona* or *colonum, Eleusine indica, Eriochloa villosa* (English name "woolly cup-grass"), *Leptochloa chinensis, Leptochloa panicoides,*

*Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum dichotomiflorum* (PANDI), *Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"), and/or *Sorghum vulgare*; and/or volunteer corn (volunteer maize) weeds.

In one embodiment, grassy monocotyledonous weeds to be controlled comprise weeds from the genus: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria,* and/or *Sorghum*, and/or volunteer corn (volunteer maize) weeds.

In a further embodiment, the grassy monocotyledonous weeds are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment the grassy monocotyledonous weeds, are "cool-season" (cool climate) grassy weeds; in which case they typically comprise weeds from the genus *Agrostis, Alopecurus, Apera, Avena, Bromus, Lolium* and/or *Poa*.

Various aspects and embodiments of the present invention will now be illustrated in more detail by way of example. It will be appreciated that modification of detail may be made without departing from the scope of the invention.

PREPARATION EXAMPLES

Those skilled in the art will appreciate that depending on the nature of the substituents $X^1$, $R^1$, $R^2$, $R^3$, $R^4$, $R^5$, $R^6$, $R^7$, $R^8$, $R^9$, $R^{10}$, $R^{11}$, $R^a$, $R^b$, $R^c$, n, p, q, r, and s, compounds of Formula I may exist in different interconvertible rotameric forms as described in, for example S. A. Richards and J. C. Hollerton, Essential Practical NMR for Organic Chemistry, John Wiley and sons (2010). For clarity, only the spectroscopic data for the major rotameric form is quoted.

General Methods

[Pd(IPr*)(cin)Cl] refers to the catalyst below—see *Chem. Eur. J.* 2012, 18, 4517

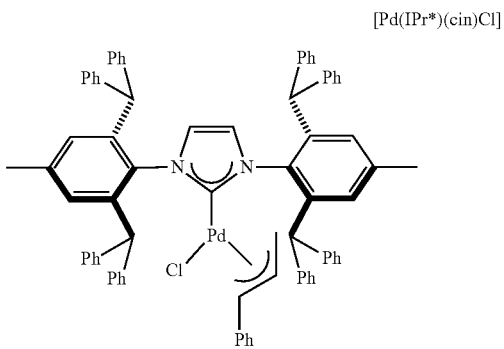

Xantphos palladacycle 4th generation refers to the catalyst below—see *Org. Lett.* 2014, 16, 4296 and WO13184198.

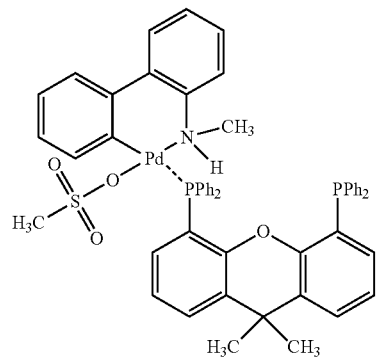

JackiePhos Pd G3 refers to the catalyst below—see *J. Am. Chem. Soc.,* 2009, 131, 16720.

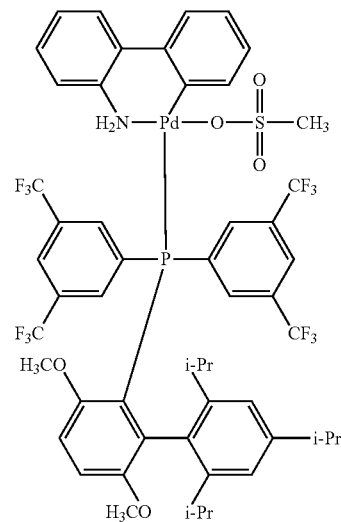

tBuBrettPhos Pd G3 refers to the catalyst below—see *Org. Lett.*, 2013, 15, 1394

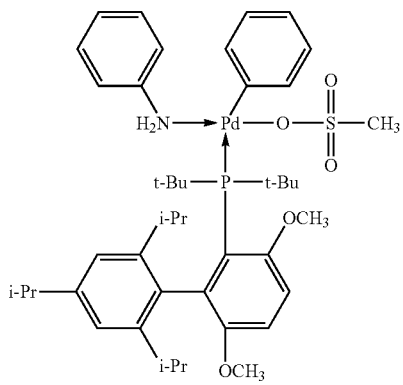

Example P1: Synthesis of N-[6-(5-fluoro-3-pyridyl)-2-(trifluoromethyl)-3-pyridyl]-2-methyl-propanamide (Compound C10)

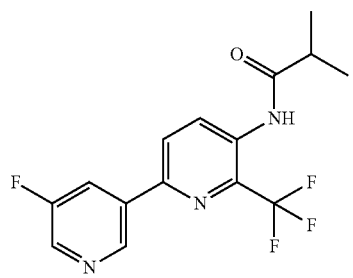 [SMILES: CC(C)C(=O)Nc1ccc(-c2cncc(F)c2)nc1C(F)(F)F]

Step 1: Synthesis of ethyl 1-oxido-2-(trifluoromethyl)pyridin-1-ium-3-carboxylate

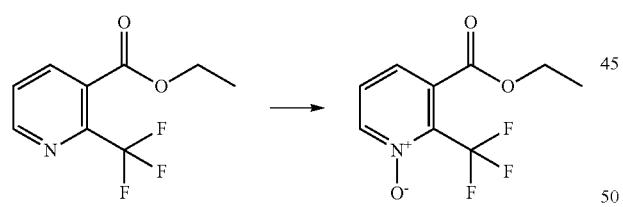

To a stirred suspension of freshly ground urea hydrogen peroxide addition compound (0.099 g, 1.05 mmol) in DCM (10 mL) at 0° C. was added ethyl 2-(trifluoromethyl)pyridine-3-carboxylate (0.1 g, 0.46 mmol) followed by slow addition (ca. 5 minutes) of a solution of trifluoroacetic anhydride (0.13 mL, 0.91 mmol) in DCM (5 mL). The reaction was allowed to warm to ambient and left stirring overnight. The reaction was washed with 2M aq. sodium carbonate solution (5 mL) and 2M aq sodium metabisulphite solution (2×10 mL) and the solvent was removed in vacuo. The crude product was purified via flash column chromatography on silica gel using an EtOAc/Hexane gradient as eluent to give the desired product (76 mg, 73%) as a thick colourless oil.

$^1$H NMR (400 MHz, CDCl$_3$) δ 8.28 (1H, d), 7.44 (1H, dd), 7.21 (1H, d), 4.43 (2H, q), 1.44 (3H, t)

Step 2: Synthesis of ethyl 6-chloro-2-(trifluoromethyl)pyridine-3-carboxylate

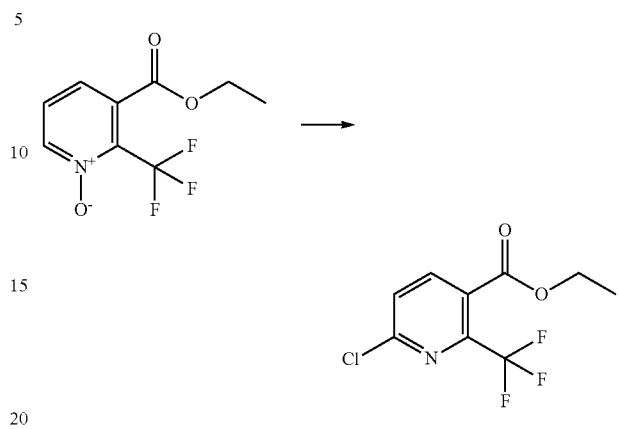

A mixture of ethyl 1-oxido-2-(trifluoromethyl)pyridin-1-ium-3-carboxylate (0.2 g, 0.85 mmol) and POCl$_3$ (2 mL, 21.24 mmol) was heated to 80° C. for 6 hours and then cooled to ambient. The reaction was quenched with 2M aq Na$_2$CO$_3$ solution and then extracted with Et$_2$O (3×15 mL). The combined organic extracts were dried over Na$_2$SO$_4$ and pre-absorbed onto silica gel for purification via flash column chromatography on silica using an EtOAc/isohexane gradient as eluent to give the desired product (0.14 g, 61%) as a colourless oil.

$^1$H NMR (400 MHz, CDCl$_3$) δ 8.09 (d, 1H), 7.60 (d, 1H), 4.43 (q, 2H), 1.43 (t, 3H).

Step 3: Synthesis of 6-chloro-2-trifluoromethyl)pyridine-3-carboxylic acid

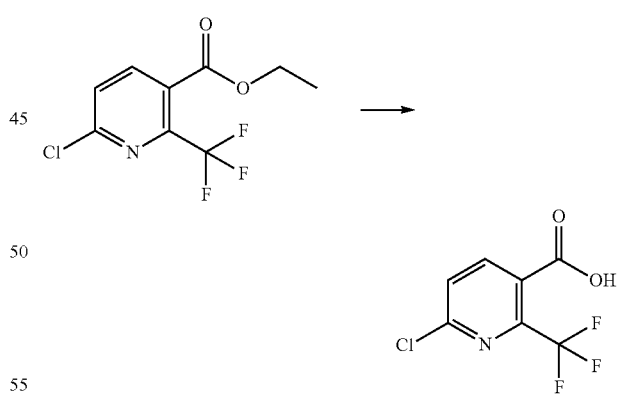

To a solution of ethyl 6-chloro-2-(trifluoromethyl)pyridine-3-carboxylate (190 mg, 0.75 mmol) in THF (4 mL) and H$_2$O (2 mL) was added LiOH.H$_2$O (72 mg, 1.72 mmol) and the reaction stirred at room temperature for 3 h. The reaction was concentrated under reduced pressure and 2N HCl was added slowly to reach pH 3-4, then extracted with EtOAc (2×10 mL). The combined organic extracts were dried over MgSO$_4$ and concentrated to dryness under reduced pressure to give the desired product (170 mg, quant) as a white solid.

$^1$H NMR (400 MHz, CDCl$_3$) δ 8.12 (1H, d), 7.62 (1H, d)

Step 4: Synthesis of tert-butyl N-[6-chloro-2-(trifluoromethyl)-3-pyridyl]carbamate

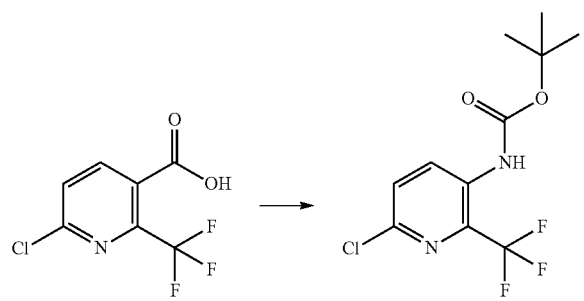 [SMILES: O=C(O)c1ccc(Cl)nc1C(F)(F)F ; CC(C)(C)OC(=O)Nc1ccc(Cl)nc1C(F)(F)F]

To a stirred solution of 6-chloro-2-(trifluoromethyl)pyridine-3-carboxylic acid (3.0 g, 13.3 mmol) in t-butanol (25 mL) was added triethylamine (2.41 mL, 17.29 mmol) and diphenylphosphoryl azide (DPPA) (3.73 mL, 17.29 mmol). The reaction was heated at 90° C. for 2 hrs and then was allowed to cool to room temperature overnight. The reaction mixture was diluted with ethyl acetate and washed with water (×2), then brine (×1), dried over MgSO$_4$ and evaporated to dryness under reduced pressure. The crude product was adsorbed onto silica and purified by flash chromatography on silica using a gradient from 5-50% ethyl acetate in isohexane as eluent to give the desired product (3.24 g, 82%) as a colourless oil.

$^1$H NMR (400 MHz, CDCl$_3$) δ 8.64 (d, 1H), 7.48 (d, 1H), 6.89 (br.s, 1H), 1.52 (s, 9H)

Step 5: Synthesis of tert-butyl N-[6-(5-fluoro-3-pyridyl)-2-(trifluoromethyl)-3-pyridyl]carbamate

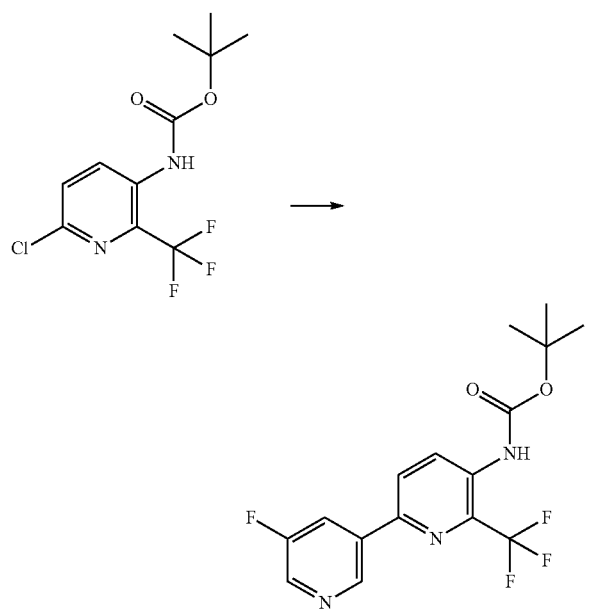

To a stirred suspension of (5-fluoro-3-pyridyl)boronic acid (1.70 g, 12 mmol), Xantphos palladacycle 4th generation (0.2 g, 0.21 mmol) and tert-butyl N-[6-chloro-2-(trifluoromethyl)-3-pyridyl]carbamate (2.50 g, 8.4 mmol) in a mixture of ethanol (6.8 mL) and toluene (25 mL) was added K$_2$CO$_3$ (8.4 mL of a 2M in water, 17 mmol). The reaction mixture was heated at reflux for 3 hrs. The reaction mixture was cooled to room temperature and concentrated to dryness. The residue was adsorbed onto silica and purified by flash chromatography on silica using a gradient from 5-100% EtOAc/isohexane as eluent to give the desired compound (2.57 g, 85%).

$^1$H NMR (400 MHz, CDCl$_3$) δ 9.02 (dd, 1H), 8.79 (d, 1H), 8.52 (d, 1H), 8.12 (m, 1H), 7.94 (d, 1H), 7.01 (br.s, 1H), 1.56 (s, 9H)

Step 6: Synthesis of 6-(5-fluoro-3-pyridyl)-2-(trifluoromethyl)pyridin-3-amine

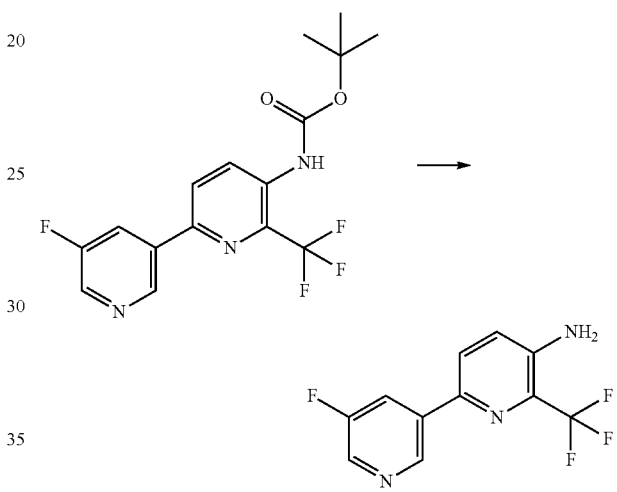

Trifluoroacetic acid (1.4 mL, 18 mmol) was added to tert-butyl N-[6-(5-fluoro-3-pyridyl)-2-(trifluoromethyl)-3-pyridyl]carbamate (685 mg, 1.92 mmol) in DCM (7 mL) and the reaction mixture was heated at reflux for 3 h before being allowed to cool to room temperature. The reaction mixture was partitioned between 2M NaOH (so pH of aqueous was greater than 12) and DCM. The aqueous layer was extracted twice with DCM and the combined organic extracts were dried over MgSO$_4$ and dry loaded on to celite. Purification by flash chromatography on silica using a gradient of 0-30% EtOAc in isohexane as eluent gave the desired compound (472 mg, 96%) as a white solid.

$^1$H NMR (400 MHz, CDCl$_3$) δ 8.93 (m, 1H), 8.45 (d, 1H), 8.12-8.00 (m, 1H), 7.75 (d 1H), 7.21 (d, 1H), 4.38 (br.s, 2H)

Step 7: Synthesis of N-[6-(5-fluoro-3-pyridyl)-2-(trifluoromethyl)-3-pyridyl]-2-methyl-propanamide

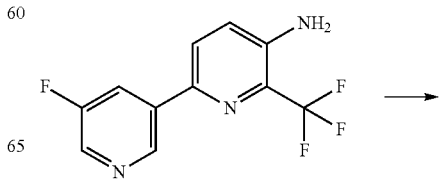

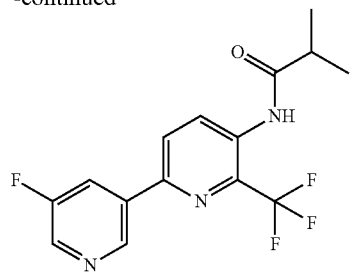

To a stirred solution of 6-(5-fluoro-3-pyridyl)-2-(trifluoromethyl)pyridin-3-amine (423 mg, 1.64 mmol) and pyridine (0.54 mL, 6.58 mmol) in DCM (20 mL) was added dropwise 2,2-dimethylpropanoyl chloride (3.2894 mmol, 0.405 mL). The reaction was stirred at room temperature overnight. The reaction was then concentrated on to silica and purified by flash chromatography on silica using an EtOAc/isohexane gradient as eluent to give the desired compound (0.41 g, 76%) as a white solid.

$^1$H NMR (400 MHz, CDCl$_3$) δ 9.07 (br.s, 1H), 8.78 (d, 1H), 8.52 (1H, br. s), 8.12 (m, 1H), 7.92 (d, 1H), 7.67 (br.s, 1H), 2.58 (m, 1H), 1.31 (d, 6H)

Example P2: Synthesis of N-[6-(5-fluoro-3-pyridyl)-2-(trifluoromethyl)-3-pyridyl]acetamide (Compound C9)

Step 1: Synthesis of N-[6-(5-fluoro-3-pyridyl)-2-(trifluoromethyl)-3-pyridyl]acetamide

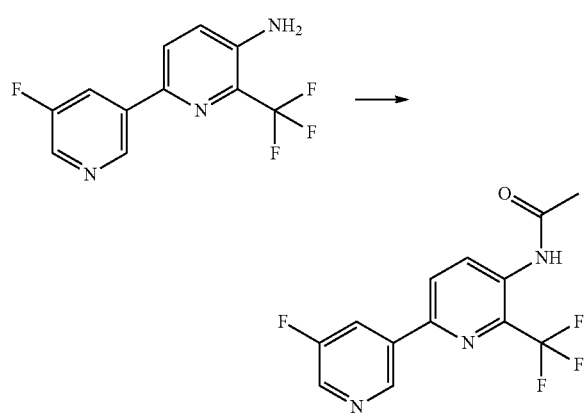

To a stirred solution of 6-(5-fluoro-3-pyridyl)-2-(trifluoromethyl)pyridin-3-amine (0.05 g, 0.194 mmol) in DCM (5 mL) was added pyridine (0.064 mL, 0.78 mmol) and acetic anhydride (0.038 mL, 0.39 mmol). The resultant pale yellow solution was left to stand at RT for 72 hours. The reaction was concentrated in vacuo and purified via flash chromatography on silica using an EtOAc/isohexane gradient as eluent to give the desired product (16 mg, 27%).

$^1$H NMR (400 MHz, CDCl$_3$) δ 9.03 (d, 1H), 8.83 (d, 1H), 8.54 (d, 1H), 8.14 (m, 1H), 7.95 (d, 1H), 7.58 (br.s, 1H), 2.30 (s, 3H)

Example P3: Synthesis of N-[6-(5-fluoro-3-pyridyl)-2-(trifluoromethyl)-3-pyridyl]-N,2-dimethyl-propanamide (compound C4)

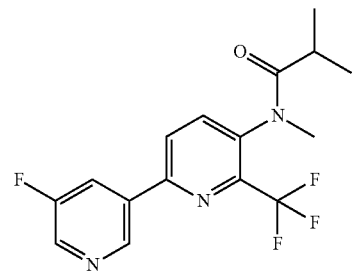 [SMILES: CC(C)C(=O)N(C)c1ccc(-c2cncc(F)c2)nc1C(F)(F)F]

Step 1: Synthesis of N-[6-(5-fluoro-3-pyridyl)-2-trifluoromethyl)-3-pyridyl]-N,2-dimethyl-propanamide To a stirred solution of N-[6-(5-fluoro-3-pyridyl)-2-(trifluoromethyl)-3-pyridyl]-2-methyl-propanamide (0.135 g, 0.4125 mmol) in DMF (9 mL) at 0° C. (ice bath) was added sodium hydride (as a 60% dispersion in mineral oil) (0.017 g, 0.4331 mmol) in a single portion. After 5 minutes the mixture was removed from the ice bath and stirred at ambient for a further 5 minutes. The reaction was then re-cooled to 0° C. (ice bath) and iodomethane (0.027 mL 0.4331 mmol) was added dropwise. After 10 minutes the mixture was allowed to warm to ambient and stirred for a further 30 minutes. The mixture was quenched with 2M HCl (500 µL) and concentrated in vacuo. The resulting residue was purified via flash column chromatography on silica gel using an EtOAc/isohexane gradient as eluent to give the desired compound (9 mg, 6%).

¹H NMR (400 MHz, CD₃OD, major rotamer) δ 9.18 (1H, s), 8.57 (1H, d), 8.17 (1H, m), 8.12 (1H, d), 7.77 (1H, d), 3.18 (3H, s), 2.21 (1H, m), 1.12 (3H, d), 0.97 (3H, d)

Example P4: Synthesis of N-acetyl-N-[6-(5-fluoro-3-pyridyl)-2-(trifluoromethyl)-3-pyridyl]acetamide (compound C5)

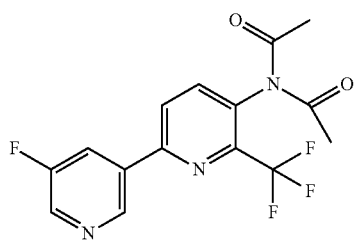 [SMILES: CC(=O)N(C(C)=O)c1ccc(-c2cncc(F)c2)nc1C(F)(F)F]

Step 1: Synthesis of N-acetyl-N-[6-(5-fluoro-3-pyridyl)-2-(trifluoromethyl)-3-pyridyl]acetamide

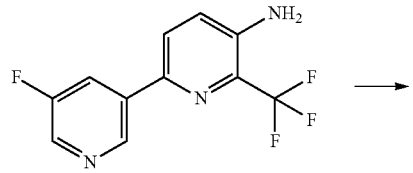

To a stirred solution of 6-(5-fluoro-3-pyridyl)-2-(trifluoromethyl)pyridin-3-amine (0.2 g, 0.778 mmol) in DCM (20 mL) was added pyridine (0.25 mL) followed by dropwise addition of acetyl chloride (0.067 mL, 0.93 mmol). The resultant pale yellow solution was left to stand at room temperature overnight. The solvent was removed in vacuo and the sample purified via flash column chromatography on silica gel using an EtOAc/isohexane gradient as eluent. The crude material was further purified by mass-directed reverse phase HPLC to give the desired compound (20.3 mg, 8%)

¹H NMR (400 MHz, CDCl₃) δ 9.08 (s, 1H), 8.61 (d, 1H), 8.18 (m, 1H), 8.08 (d, 1H), 7.72 (d, 1H), 2.33 (s, 6H)

Example P5: Synthesis of N-[6-(5-chloro-3-pyridyl)-2-(trifluoromethyl)-3-pyridyl]-N,2-dimethyl-propanamide (compound C12)

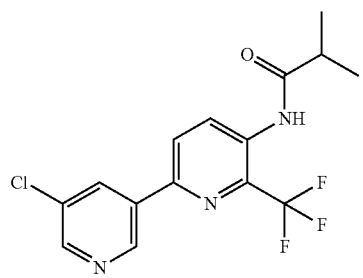 [SMILES: CC(C)C(=O)Nc1ccc(-c2cncc(Cl)c2)nc1C(F)(F)F]

Step 1: Synthesis of 6-chloro-2-(trifluoromethyl)pyridin-3-amine

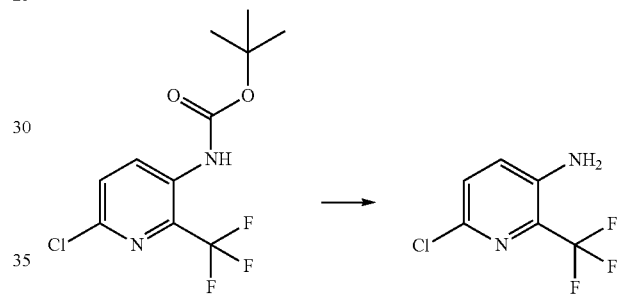

To a stirred solution of tert-butyl N-[6-chloro-2-(trifluoromethyl)-3-pyridyl]carbamate (2.5 g, 8.4 mmol) in DCM (8 mL) was added TFA (6.6 mL, 84 mmol). The reagents were stirred overnight at room temperature. The reaction was basified with saturated aq sodium bicarbonate solution and then extracted with DCM (2×10 mL). The combined organic extracts were dried over MgSO₄ and concentrated to give the desired compound (1.50 g, 91%) as a waxy white solid.

¹H NMR (400 MHz, CDCl₃) δ 7.25 (d, 1H), 7.02 (d, 1H), 4.27 (br.s, 2H)

Step 2: Synthesis of N-[6-chloro-2-(trifluoromethyl)-3-pyridyl]-2-methyl-propanamide

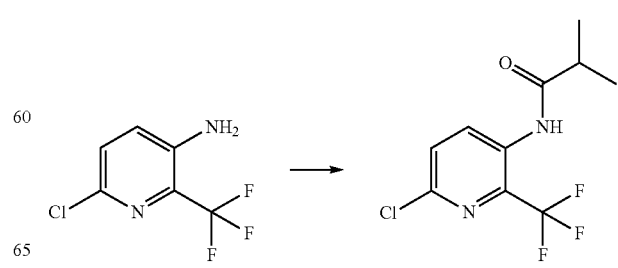

To a stirred solution of 6-chloro-2-(trifluoromethyl)pyridin-3-amine (351 mg, 1.79 mmol) in DCM (3 mL) and pyridine (0.58 mL, 7.14 mmol) was added 2-methylpropanoyl chloride (0.374 mL, 3.57 mmol). The reaction mixture was allowed to stir at room temperature overnight. The reaction mixture was concentrated and purified by flash chromatography on silica using a gradient from 5-100% EtOAc in isohexane as eluent to give the desired compound (234 mg, 49%) as a white solid.

$^1$H NMR (400 MHz, CDCl$_3$) δ 8.73 (d, 1H), 7.58 (br.s, 1H), 7.51 (d, 1H), 2.67-2.54 (m, 1H), 1.29 and 1.21 (2×d, 6H)

Step 3: Synthesis of N-[6-(5-chloro-3-pyridyl)-2-(trifluoromethyl)-3-pyridyl]-N,2-dimethyl-propanamide

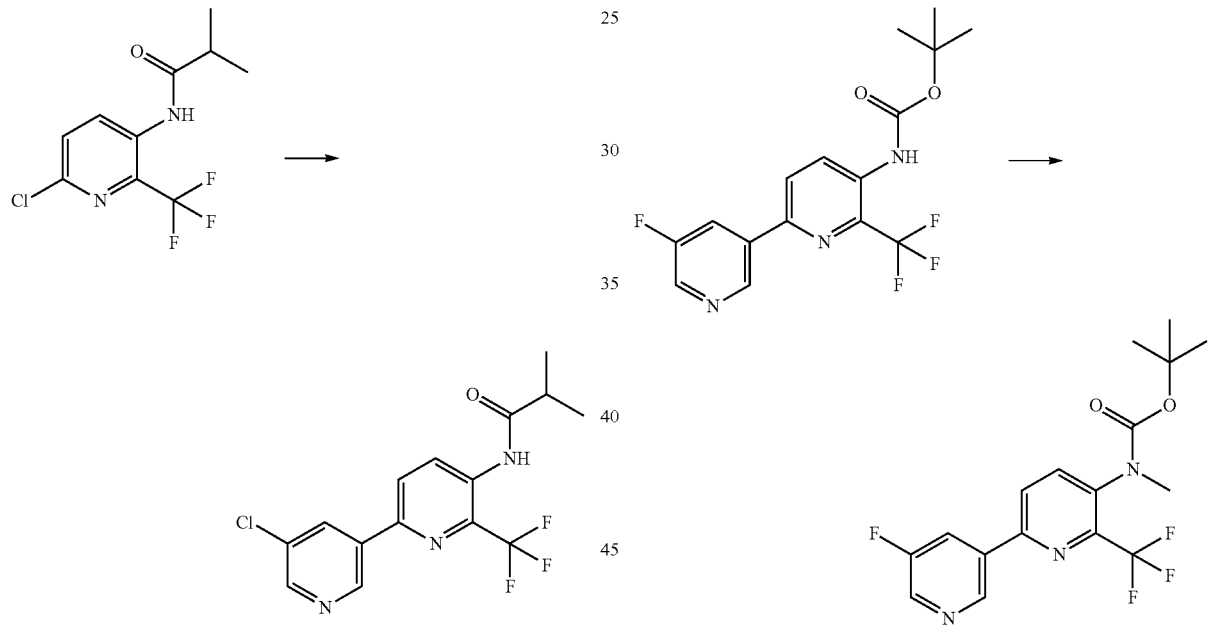

A microwave vial was charged with N-[6-chloro-2-(trifluoromethyl)-3-pyridyl]-2-methyl-propanamide (117 mg, 0.44 mmol), (5-chloro-3-pyridyl)boronic acid (138 mg, 0.88 mmol), caesium carbonate (429 mg, 1.32 mmol), [1,1'-bis(diphenylphosphino)ferrocene]dichloropalladium(II) (32 mg, 0.044 mmol), 1,4-dioxane (3 mL) and H$_2$O (0.3 mL). The vial was capped and the contents degassed by evacuating and purging with nitrogen (×3). The reaction mixture was heated under microwave irradiation at 120° C. for 30 mins. The reaction mixture was concentrated and purified by flash chromatography on silica using a gradient from 5-100% EtOAc in isohexane as eluent to give the desired compound (100 mg, 66%) as a white solid.

$^1$H NMR (400 MHz, CDCl$_3$) δ 9.08 (s, 1H), 8.89 (d, 1H), 8.62 (s, 1H), 8.38 (s, 1H), 7.96 (d, 1H), 7.68 (br s, 1H), 2.69-2.59 (m, 1H), 1.32 (d, 6H)

Example P6: Synthesis of N-[6-(5-fluoro-3-pyridyl)-2-(trifluoromethyl)-3-pyridyl]-N-methyl-propanamide (compound C15)

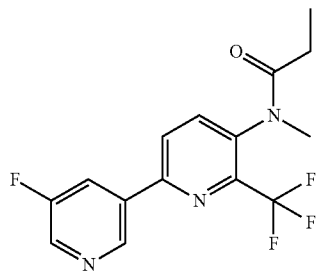 [SMILES: CCC(=O)N(C)c1ccc(-c2cncc(F)c2)nc1C(F)(F)F]

Step 1: Synthesis of tert-butyl N-[6-(5-fluoro-3-pyridyl)-2-(trifluoromethyl)-3-pyridyl]-N-methyl-carbamate

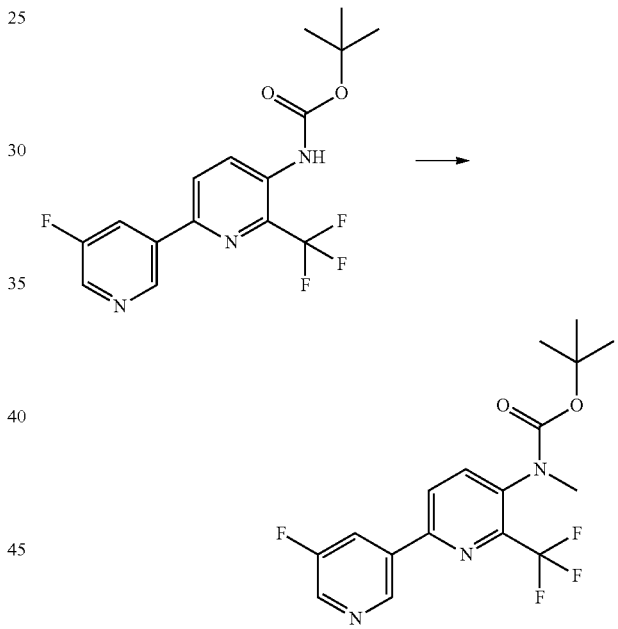

To a stirred solution of tert-butyl N-[6-pyrimidin-5-yl-2-(trifluoromethyl)-3-pyridyl]carbamate (422 mg, 1.24 mmol) in DMF (4.2 mL) at 5° C. under an N$_2$ atmosphere was added sodium hydride (as a 60% dispersion in mineral oil) (0.059 g, 1.49 mmol) in a single portion. The reaction mixture was allowed to warm to room temperature and stir for 1 hr then iodomethane (0.115 mL, 1.86 mmol) was added and the reaction mixture stirred for a further 2 hrs. The reaction mixture was diluted with water and extracted with EtOAc (3×10 mL). The combined organic extracts were washed with brine, dried over MgSO$_4$ and concentrated to give a yellow gum. The crude product was purified by flash chromatography on silica using a gradient from 5-100% EtOAc in isohexane as eluent to give the desired compound (354 mg, 81%) as an orange gum.

$^1$H NMR (400 MHz, CDCl$_3$, major rotamer) δ 9.07 (s, 1H), 8.57 (d, 1H), 8.20 (br.d, 1H), 8.01 (d, 1H), 7.76 (d, 1H), 3.22 (s, 3H), 1.33 (s, 9H)

Step 2: Synthesis of 6-(5-fluoro-3-pyridyl)-N-methyl-2-(trifluoromethyl)pyridin-3-amine

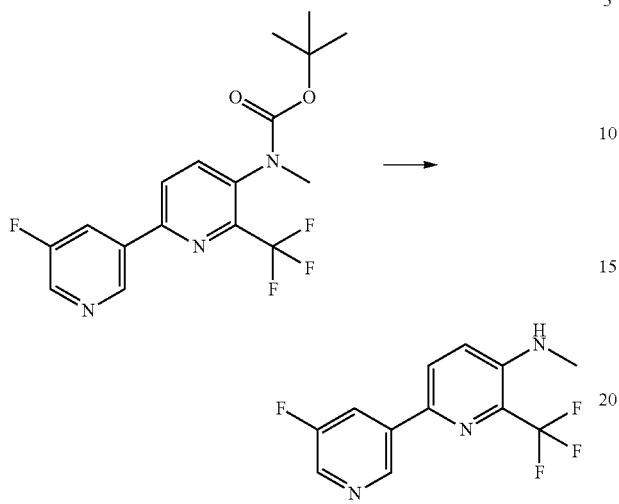

To a stirred solution of tert-butyl N-methyl-N-[6-pyrimidin-5-yl-2-(trifluoromethyl)-3-pyridyl]carbamate (453 mg, 1.28 mmol) in DCM (10 mL) was added portionwise, trifluoroacetic acid (0.49 mL, 6.39 mmol). The reaction mixture was stirred at room temperature for 72 h. The reaction mixture was diluted with DCM and saturated sodium bicarbonate solution was added portionwise. The two layers were separated and the aqueous extracted again with DCM (×2). The organics were combined, washed with brine, dried over MgSO₄ and concentrated. The crude product was purified by flash chromatography on silica using a gradient from 0-10% MeOH in DCM as eluent to give the desired compound (317 mg, 98%) as a yellow solid.

¹H NMR (400 MHz, CDCl₃) δ 8.93 (s, 1H), 8.42 (d, 1H), 8.05 (m, 1H), 7.82 (d, 1H), 7.17 (d, 1H), 4.72 (br.s, 1H), 2.98 (app. d, 3H)

Step 3: Synthesis of N-[6-(5-fluoro-3-pyridyl)-2-(trifluoromethyl)-3-pyridyl]-N-methyl-propanamide

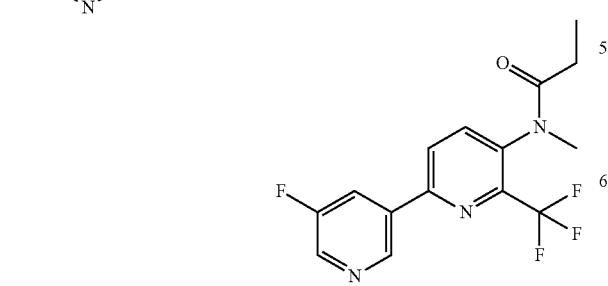

To a stirred solution of 6-pyrimidin-5-yl-2-(trifluoromethyl)pyridin-3-amine (80 mg, 0.33 mmol) in 1,4-dioxane (3 mL) was added pyridine (0.03 mL, 0.4 mmol) and then propionyl chloride (0.035 mL, 0.4 mmol). The reaction was stirred at room temperature overnight. The reaction mixture was concentrated and taken up in ethyl acetate and washed with water, saturated sodium bicarbonate solution and then water. The organic phase was dried over MgSO₄, concentrated and then purified by mass-directed reverse phase HPLC to give the desired compound (36 mg, 19%) as an oil.

¹H NMR (400 MHz, CDCl₃, major rotamer) δ 9.15 (s, 1H), 8.64 (m, 1H), 8.39 (m, 1H), 8.15 (d, 1H), 7.86 (d, 1H), 3.27 (s, 3H), 2.00 (2H, m), 1.08 (3H, t)

Example P7: Synthesis of 2-methyl-N-(2-methyl-6-pyrimidin-5-yl-3-pyridyl)propanamide (compound C2)

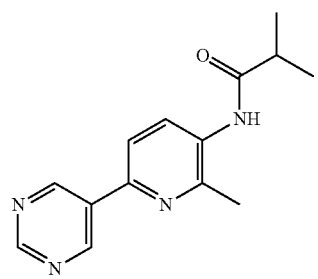 [SMILES: Cc1nc(-c2cncnc2)ccc1NC(=O)C(C)C]

Step 1: Synthesis of tert-butyl N-(6-chloro-2-methyl-3-pyridyl)carbamate

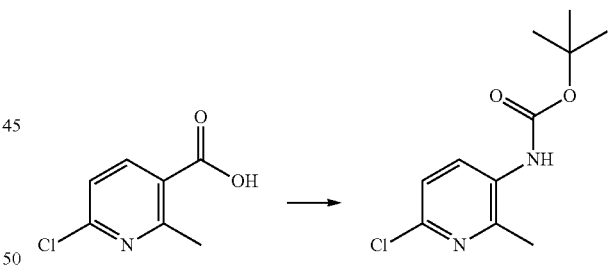

To stirred solution of 6-chloro-2-methyl-pyridine-3-carboxylic acid in tert-butanol (15 mL) was added Et₃N (1.85 mL, 13.3 mmol) and DPPA (2.86 mL, 3.3 mmol) and the reaction heated at 90° C. for 2 hours. The reaction was allowed to cool to room temperature overnight, diluted with water (50 mL) and extracted with EtOAc (3×30 mL). The combined organic extracts were washed with water (15 mL), brine (15 mL), dried over MgSO₄ and evaporated to dryness under reduced pressure. The residue was purified by flash chromatography over SiO₂ using a gradient of 5-50% EtOAc/isohexane as eluent to give the desired product (1.75 g, 71%) as a white solid.

¹H NMR (400 MHz, CDCl₃) δ 8.18 (br. d, 1H), 7.16 (d, 1H), 6.26 (br.d, 1H), 2.48 (s, 3H), 1.52 (s, 9H).

Step 2: Synthesis of 6-chloro-2-methyl-pyridin-3-amine

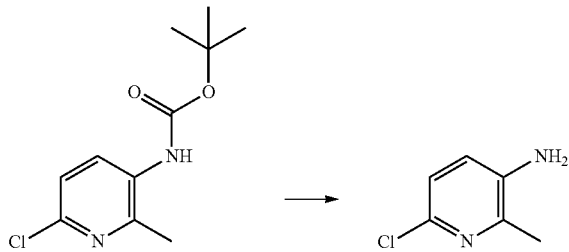

To a stirred solution of tert-butyl N-(6-chloro-2-methyl-3-pyridyl)carbamate (500 mg, 2.06 mmol) in DCM (8 mL) was added trifluoroacetic acid (1.63 mL, 20.6 mmol). The reaction was heated at reflux for 2 hours, cooled to RT and quenched with saturated aqueous $NaHCO_3$ solution (20 mL). The reaction mixture was extracted with DCM (3×20 mL) and the combined organic extracts dried over $MgSO_4$ and evaporated to dryness under reduced pressure to give the desired product (320 mg, quant) as a waxy solid.

$^1$H NMR (400 MHz, $CDCl_3$) δ 6.89 (d, 1H), 6.81 (d, 1H), 3.59 (br.s, 2H), 2.29 (s, 3H).

Step 3: Synthesis of N-(6-chloro-2-methyl-3-pyridyl)-2-methyl-propanamide

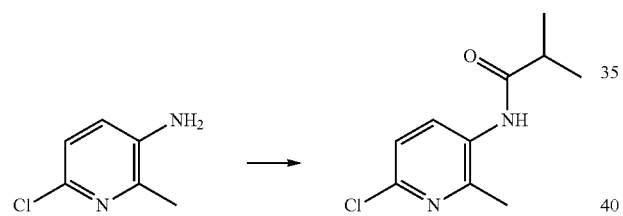

To a stirred solution of 6-chloro-2-methyl-pyridin-3-amine (320 mg, 2.24 mmol) in DCM (3 mL) was added pyridine (0.726 mL, 8.98 mmol) and 2-methyl propionyl chloride (0.47 mL, 4.49 mmol). The reaction was stirred at room temperature overnight, then evaporated to dryness under reduced pressure and the residue purified by flash chromatography over $SiO_2$ using an EtOAc/isohexane gradient as eluent to give the desired product (259 mg, 54%) as a white solid.

$^1$H NMR (400 MHz, $CDCl_3$) δ 8.27 (d, 1H), 7.19 (d, 1H, 6.93 (br.s, 1H), 2.61-2.54 (m, 1H), 2.49 (s, 3H), 1.29 (d, 6H).

Step 4: Synthesis of 2-methyl-N-(2-methyl-6-pyrimidin-5-yl-3-pyridyl)propanamide

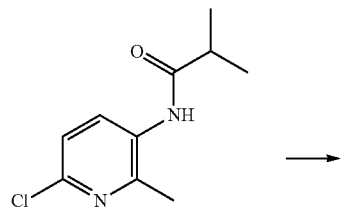

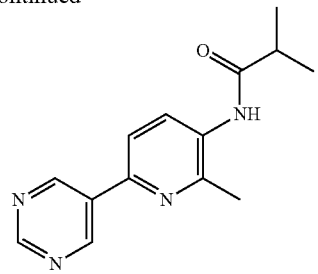

To a solution of N-(6-chloro-2-methyl-3-pyridyl)-2-methyl-propanamide (130 mg, 0.611 mmol) in EtOH (10 mL) was added pyrimidin-5-yl boronic acid (114 mg, 0.92 mmol), $K_2CO_3$ (188 mg, 1.34 mmol) and [Pd(IPr*)(cin)Cl] (36 mg, 0.03 mmol). The reaction was heated at reflux for 2 hours, allowed to cool to room temperature and evaporated to dryness under reduced pressure. The residue was purified by flash chromatography over $SiO_2$ using an EtOAc/isohexane gradient as eluent to give the desired product (146 mg, 93%) as an off-white solid.

$^1$H NMR (400 MHz, $CDCl_3$) δ 9.30 (s, 2H), 9.22 (s, 1H), 8.50 (d, 1H), 7.63 (d, 1H), 7.08 (br.s, 1H), 2.68-2.58 (m, 1H), 2.62 (s, 3H), 1.32 (d, 6H).

Example P8: Synthesis of N-[6-(5-fluoro-3-pyridyl)-2-(trifluoromethyl)-3-pyridyl]pyridine-3-carboxamide (compound C50)

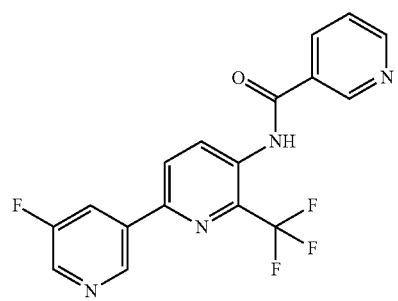 [SMILES: O=C(Nc1ccc(-c2cncc(F)c2)nc1C(F)(F)F)c1cccnc1]

Step 1: Synthesis of 3-chloro-6-(5-fluoro-3-pyridyl)-2-(trifluoromethyl)pyridine

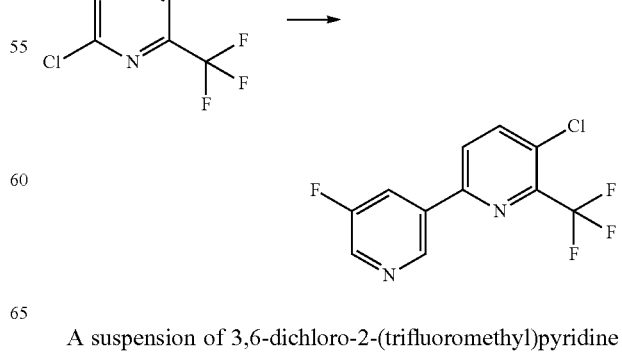

A suspension of 3,6-dichloro-2-(trifluoromethyl)pyridine (2.0 g, 9.26 mmol) and (5-fluoro-3-pyridyl) boronic acid (1.44 g, 10.19 mmol) in a mixture of EtOH (5.4 mL), toluene (20 mL) and water (9.25 mL) was sparged with $N_2$ for 30 minutes at RT. $K_2CO_3$ (2.56 g, 18.52 mmol) and Xantphos Pd G4 (222 mg, 0.232 mmol) was added and the reaction heated to 80° C. for 2.5 hours. The reaction was allowed to cool to RT, diluted with EtOAc (100 mL) and washed with water (100 mL). The aqueous phase was extracted with further EtOAc (2×100 mL). The combined organic extracts were dried over $MgSO_4$ and evaporated to dryness under reduced pressure. The crude material was purified by flash chromatography on silica gel using an EtOAc/isohexane gradient as eluent to give the desired product (2.16 g, 84%) as a pale orange oil which solidified on standing.

$^1$H NMR (400 MHz, $CDCl_3$) δ 9.03 (s, 1H), 8.58 (s, 1H), 8.15 (d, 1H), 7.98 (d, 1H), 7.92 (d, 1H).

Step 2: Synthesis of N-[6-(5-fluoro-3-pyridyl)-2-(trifluoromethyl)-3-pyridyl]pyridine-3-carboxamide (compound C50)

A microwave vial was charged with 3-chloro-6-(5-fluoro-3-pyridyl)-2-(trifluoromethyl)pyridine (50 mg, 0.18 mmol), tBuBrettPhos Pd G3 (6 mg, 0.0072 mmol), $K_3PO_4$ (54 mg, 0.25 mmol), pyridine-3-carboxamide (26 mg, 0.22 mmol) and $^t$BuOH (1 mL) and heated for 1 hour at 130° C. under microwave irradiation. The reaction was diluted with EtOAc (20 mL) and washed with water (20 mL). The aqueous layer was extracted with further EtOAc (2×20 mL) and then the combined organic extracts were dried over $MgSO_4$ and evaporated to dryness under reduced pressure to give an orange oil. The crude product was purified by flash chromatography on silica gel using an EtOAc/isohexane gradient as eluent to give the desired compound (30 mg, 46%) as a colourless solid.

$^1$H NMR (400 MHz, $CDCl_3$) δ 9.16 (s, 1H), 9.10-9.00 (m, 2H), 8.91-8.87 (m, 1H), 8.56 (d, 1H), 8.48 (br. s, 1H), 8.25-8.20 (m, 1H), 8.20-8.13 (m, 1H), 8.07 (d, 1H), 7.56-7.50 (m, 1H).

Example P9: Synthesis of 1-[6-(5-fluoro-3-pyridyl)-2-(trifluoromethyl)-3-pyridyl]piperidin-2-one (compound C54)

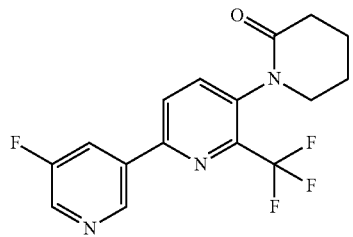 [SMILES: O=C1CCCCN1c1ccc(-c2cncc(F)c2)nc1C(F)(F)F]

Step 1: Synthesis of 1-[6-(5-fluoro-3-pyridyl)-2-(trifluoromethyl)-3-pyridyl]piperidin-2-one (compound C54)

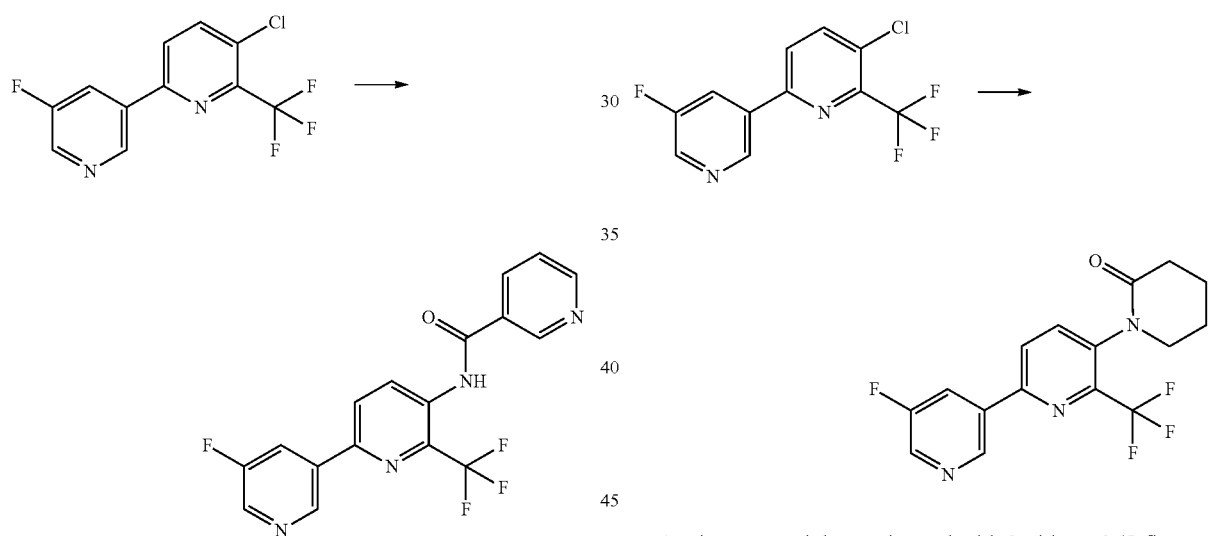

A microwave vial was charged with 3-chloro-6-(5-fluoro-3-pyridyl)-2-(trifluoromethyl)pyridine (150 mg, 0.54 mmol), JackiePhos Pd G3 (25 mg, 0.022 mmol), $Cs_2CO_3$ (353 mg, 1.08 mmol) piperidin-2-one (134 mg, 1.36 mmol) and toluene (1.5 mL) and heated for 1 hour at 150° C. under microwave irradiation. The reaction mixture was diluted in EtOAc (20 mL) and washed with water (20 mL). The aqueous layer was extracted with further EtOAc (2×20 mL) and the combined organic extracts were dried over $MgSO_4$ and evaporated to dryness under reduced pressure. The crude product was purified by flash chromatography on silica gel using an EtOAc/isohexane gradient as eluent. The resultant pale brown solid was triturated with water and filtered through a plug of celite, washing with further water. The plug was then eluted with DCM and the eluant dried over $MgSO_4$ and evaporated to dryness under reduced pressure to give the desired product (25 mg, 14%) as a pale orange solid.

$^1$H NMR (400 MHz, $CDCl_3$) δ 9.03 (s, 1H), 8.57 (s, 1H), 8.17 (d, 1H), 8.04 (d, 1H), 7.80 (d, 1H), 3.66-3.53 (m, 2H), 2.17-2.53 (m, 2H), 2.11-1.90 (m, 4H).

Example P10: Synthesis of 1-[6-(5-fluoro-3-pyridyl)-2-(trifluoromethyl)-3-pyridyl]pyrrolidine-2,5-dione (compound C67)

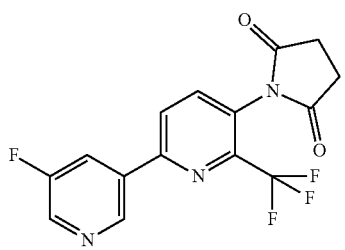 [SMILES: O=C1CCC(=O)N1c1ccc(-c2cncc(F)c2)nc1C(F)(F)F]

Step 1: Synthesis of Synthesis of 1-[6-(5-fluoro-3-pyridyl)-2-(trifluoromethyl)-3-pyridyl]pyrrolidine-2,5-dione (compound C67)

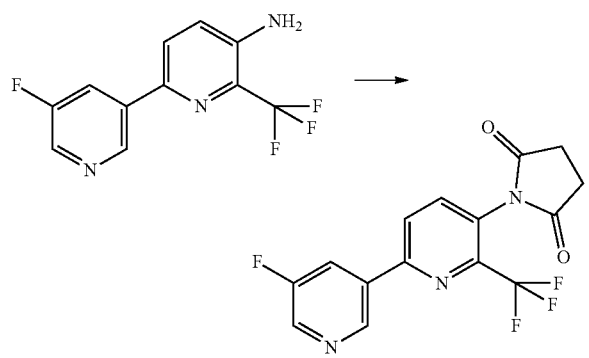

To a stirred solution of 6-(5-fluoro-3-pyridyl)-2-(trifluoromethyl)pyridin-3-amine (1.0 g, 3.9 mmol) in DCM (250 mL) was added $Et_3N$ (1.3 mL, 9.2 mmol) and dropwise succinyl chloride (1.3 mL, 11.0 mmol). The reaction was stirred at RT for 4 hours and then evaporated to dryness under reduced pressure. The crude material was purified initially by flash chromatography on silica gel using a MeOH/DCM gradient as eluent and subsequently by mass-directed reverse phase HPLC to give the desired product (395 mg, 30%) as a tan solid.

$^1$H NMR (400 MHz, $CDCl_3$) 9.46 (s, 2H), 9.28 (s, 1H), 8.05 (d, 1H), 7.78 (d, 1H), 3.15-2.87 (m, 4H).

Example P11: Synthesis of N-[2-cyano-6-(5-fluoro-3-pyridyl)-3-pyridyl]-2-methoxy-acetamide (compound C114)

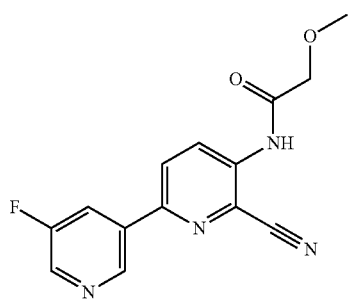 [SMILES: COCC(=O)Nc1ccc(-c2cncc(F)c2)nc1C#N]

Step 1: Synthesis of 3-amino-6-(5-fluoro-3-pyridyl)pyridine-2-carbonitrile

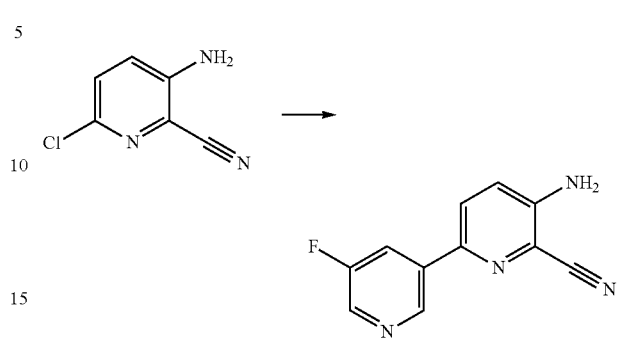

A mixture of 3-amino-6-chloro-pyridine-2-carbonitrile (330 mg, 2.15 mmol), 5-fluoropyridine-3-boronic acid (394 mg, 2.69 mmol), potassium carbonate (633 mg, 4.73 mmol) and [Pd(IPr*)(cin)Cl] (126 mg, 0.11 mmol) in EtOH (9.9 mL) was heated at 80° C. for 1 hour under an $N_2$ atmosphere and then allowed to cool to room temperature. The mixture was filtered through celite and concentrated in vacuo. The resultant orange-brown gum was adsorbed onto silica and purified by flash chromatography on silica using an EtOAc/isohexane gradient as eluent to give the desired product (80 mg, 17%) as a brown gum.

$^1$H NMR (400 MHz, $CD_3OD$) δ 8.95 (d, 1H), 8.43 (d, 1H), 8.18-8.09 (m, 1H), 7.93 (d, 1H), 7.35 (d, 1H)

Step 2: Synthesis of N-[2-cyano-6-(5-fluoro-3-pyridyl)-3-pyridyl]-2-methoxy-acetamide (compound C114)

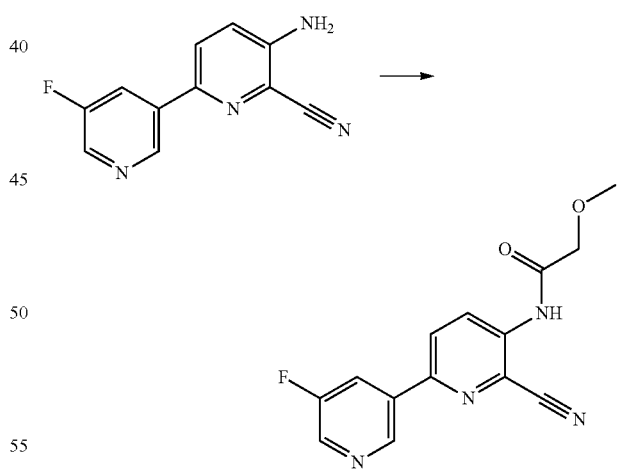

To a stirred solution of 3-amino-6-(5-fluoro-3-pyridyl)pyridine-2-carbonitrile (0.2 g, 0.93 mmol) and pyridine (0.30 mL 3.73 mmol) in DCM (3 mL) at 0° C. was added dropwise a solution of 2-methoxyacetyl chloride (0.127 g, 1.17 mmol) in DCM (2 mL). The reaction was allowed to warm to RT and stirred for a further hour. The reaction was evaporated to dryness under reduced pressure and purified twice by flash chromatography on silica gel using EtOAc/isohexane gradients as eluent to give the desired compound (126 mg, 47%).

¹H NMR (400 MHz, CDCl₃) δ 9.12 (br. s, 1H), 9.02 (s, 1H), 9.00 (d, 1H), 8.55 (d, 1H), 8.09 (m, 1H), 8.00 (d, 1H), 4.13 (s, 2H), 3.60 (s, 3H)

Example P12: Synthesis of N-acetyl-N-[6-(5-fluoro-3-pyridyl)-2-(trifluoromethyl)-3-pyridyl]propanamide (compound C121)

Step 1: Synthesis of N-acetyl-N-[6-(5-fluoro-3-pyridyl)-2-(trifluoromethyl)-3-pyridyl]propanamide (compound C121)

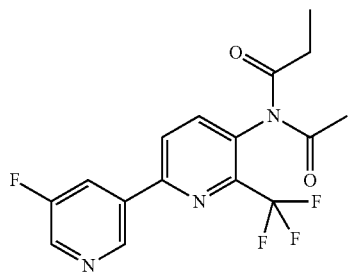 [SMILES: CCC(=O)N(C(C)=O)c1ccc(-c2cncc(F)c2)nc1C(F)(F)F]

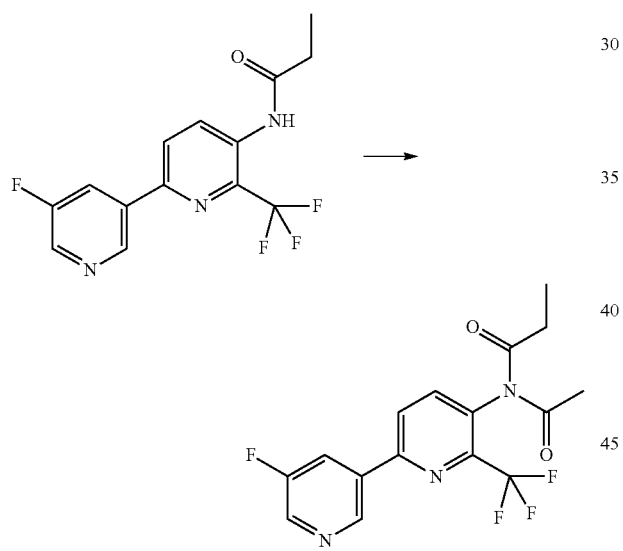

To a stirred solution of N-[6-(5-fluoro-3-pyridyl)-2-(trifluoromethyl)-3-pyridyl]propanamide (0.1 g, 0.32 mmol) in THF (15 mL) at 0° C. under an N₂ atmosphere was added NaHMDS (1 M in THF) (0.32 mL, 0.3193 mmol) and the mixture stirred for ca. 5 mins. After this time acetyl chloride (0.05 mL, 0.7024 mmol) was added and the mixture stirred at 0° C. for a further hour then allowed to warm to RT over 3 hours. 10% Sodium metabisulphite (10 mL) was added and the mixture was stirred for ca. 5 mins. The material was concentrated under reduced pressure to remove most of the THF and the mixture was diluted with DCM (50 mL) and passed through a phase-separation cartridge. The resulting solution was evaporated to dryness under reduced pressure and the crude material purified twice by flash chromatography on silica gel using EtOAc/isohexane gradients as eluent to give the desired compound (5 mg, 4%) as a colourless gum.

¹H NMR (400 MHz, CDCl₃) δ 9.08 (t, 1H), 8.60 (d, 1H), 8.21 (m, 1H), 8.11 (d, 1H), 7.77 (d, 1H), 2.52 (m, 1H), 2.40 (s, 3H), 1.14 (t, 3H).

Example P13: Synthesis of 4-[[6-(5-fluoro-3-pyridyl)-2-(trifluoromethyl)-3-pyridyl]amino]-4-oxo-butanoic acid (compound C113)

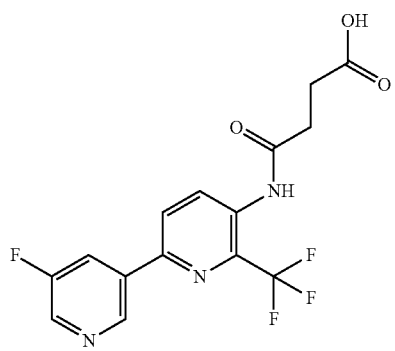 [SMILES: O=C(O)CCC(=O)Nc1ccc(-c2cncc(F)c2)nc1C(F)(F)F]

Step 1: Synthesis of 4-[[6-(5-fluoro-3-pyridyl)-2-(trifluoromethyl)-3-pyridyl]amino]4-oxo-butanoic acid (compound C113)

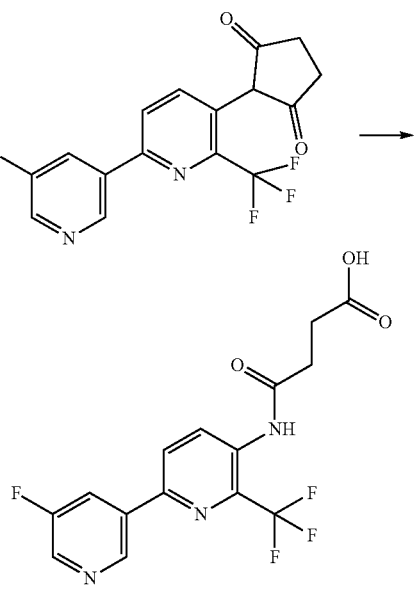

To a stirred solution of 1-[6-(5-fluoro-3-pyridyl)-2-(trifluoromethyl)-3-pyridyl]pyrrolidine-2,5-dione (0.1 g, 0.29 mmol) in THF (2 mL) was added NaOH (2M in H₂O) (0.5 mL) and the mixture stirred at RT for 5 hours. The reaction mixture was evaporated to dryness under reduced pressure and stored at −20° C. overnight. The residue was purified by mass-directed reverse phase HPLC to give the desired product (16 mg, 15%) as a colourless solid.

¹H NMR (400 MHz, CD₃OD) 9.14 (dd, 1H), 8.55 (d, 1H), 8.32-8.24 (m, 3H), 2.75 (m, 2H), 2.70 (m, 2H).

Example P14: Synthesis of N-[6-(5-fluoro-3-pyridyl)-2-(trifluoromethyl)-3-pyridyl]pyrimidine-5-carboxamide (compound C120)

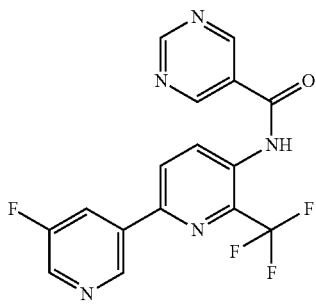

Step 1: Synthesis of N-[6-(5-fluoro-3-pyridyl)-2-(trifluoromethyl)-3-pyridyl]pyrimidine-5-carboxamide (compound C120)

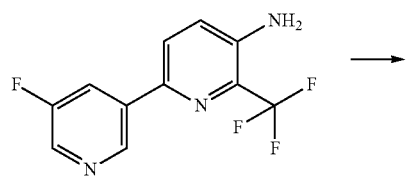 →

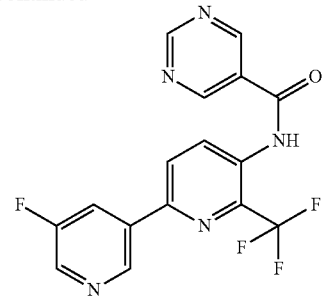 [SMILES: O=C(Nc1ccc(-c2cncc(F)c2)nc1C(F)(F)F)c1cncnc1]

To a solution of 6-(5-fluoro-3-pyridyl)-2-(trifluoromethyl)pyridin-3-amine (80 mg, 0.31 mmol) and pyrimidine-5-carboxylic acid (116 mg, 0.93 mmol) in toluene (3.1 mL) was added sequentially N,N-diisopropylethylamine (0.27 mL, 1.56 mmol) and then 1-propanephosphonic anhydride (50% solution in EtOAc) (790 mg, 1.24 mmol). The reaction was heated at reflux for 18 hours, cooled to RT and the poured into sat. aq. NaHCO$_3$ solution (20 mL). The reaction was extracted with DCM (2×10 mL), the combined organic extracts were evaporated to dryness under reduced pressure and the residue purified by mass-directed reverse phase HPLC to give the desired product (90 mg, 80%) as a white solid).

$^1$H NMR (400 MHz, CDCl$_3$) δ 9.48 (s, 1H), 9.27 (s, 2H), 9.09 (t, 1H), 9.00 (d, 1H), 8.59 (d, 1H), 8.33 (br. s, 1H), 8.25-8.17 (m, 1H), 8.10 (d, 1H).

Further examples of the invention were made in an analogous manner using the methods described above in Examples P1 to P14, with respect to compounds C2, C4, C5, C9, C10, C12, C15, C50, C54, C67, C114, C121, C113 and C120. Table 2 below, shows the structure of these compounds and the physical characterising data obtained using one or more of methods A to C as outlined below.

TABLE 2

Characterising data for Compounds of formula (I) made by the methods described above

| Cmpd ID | Structure | $^1$H NMR Data (400 MHz, CDCl$_3$ unless stated) | Mass/ Da | Mass Spec | m/z Method |
|---|---|---|---|---|---|
| C1 | | 9.02 (s, 1H), 8.52 (d, 1H), 8.18-8.12 (m, 1H), 7.71 (d, 1H), 7.49 (d, 1H), 3.10-2.98 (m, 2H), 2.48 (s, 3H), 1.19 (d, 12H) | 343.2 | — | — |
| C2 | 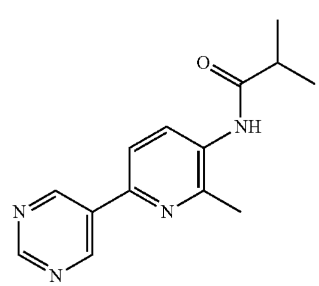 [SMILES: Cc1nc(-c2cncnc2)ccc1NC(=O)C(C)C] | 9.30 (s, 2H), 9.22 (s, 1H), 8.50 (d, 1H), 7.63 (d, 1H), 7.08 (br.s, 1H), 2.68-2.58 (m, 1H), 2.62 (s, 3H), 1.32 (d, 6H) | 256.1 | — | — |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C3 | 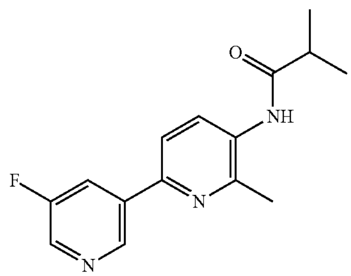 [SMILES: Cc1nc(-c2cncc(F)c2)ccc1NC(=O)C(C)C] | 8.99 (s, 1H), 8.49-8.42 (m, 2H), 8.10-8.04 (m, 1H), 7.63 (d, 1H), 7.14 (br.s, 1H), 2.69-2.59 (m, 1H), 2.60 (s, 3H), 1.31 (d, 6H) | 273.1 | — | — |
| C4 | 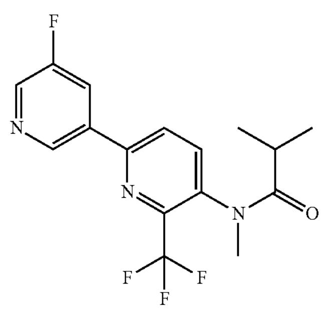 [SMILES: CC(C)C(=O)N(C)c1ccc(-c2cncc(F)c2)nc1C(F)(F)F] | (CD₃OD, major rotamer) 9.18 (1H, s), 8.57 (1 H.d), 8.17 (1H, m), 8.12 (1H, d), 7.77 (1H, d), 3.18 (3H, s), 2.21 (1H, m), 1.12 (3H, d), 0.97 (3H, d) | 341.1 | [MH]+ 342; tr 0.91 mins | B |
| C5 | 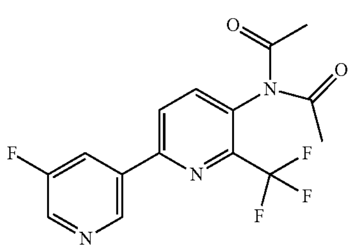 [SMILES: CC(=O)N(C(C)=O)c1ccc(-c2cncc(F)c2)nc1C(F)(F)F] | 9.08 (s, 1H), 8.61 (d, 1H), 8.18 (m, 1H), 8.08 (d, 1H), 7.72 (d, 1H), 2.33 (s, 6H); | 341.1 | — | — |
| C6 | 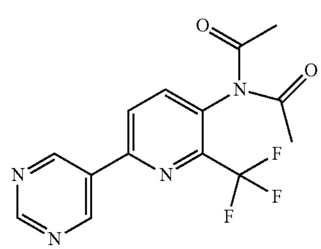 [SMILES: CC(=O)N(C(C)=O)c1ccc(-c2cncnc2)nc1C(F)(F)F] | 9.42 (s, 2H), 9.32 (s, 1H), 8.10 (d, 1H), 7.78 (d, 1H), 2.34 (s, 6H); | 324.1 | — | — |
| C7 | 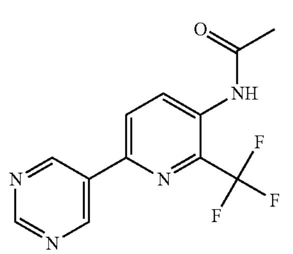 [SMILES: CC(=O)Nc1ccc(-c2cncnc2)nc1C(F)(F)F] | 9.35 (s, 2H), 9.30 (s, 1H), 8.91 (d, 1H), 7.95 (d, 1H), 7.60 (br.s, 1H), 2.32 (s, 3H) | 282.1 | — | — |

TABLE 2-continued

Characterising data for Compounds of formula (I) made by the methods described above

| Cmpd ID | Structure | $^1$H NMR Data (400 MHz, CDCl$_3$ unless stated) | Mass/ Da | Mass Spec | m/z Method |
|---|---|---|---|---|---|
| C8 | 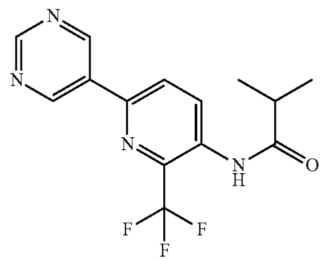 [SMILES: CC(C)C(=O)Nc1ccc(-c2cncnc2)nc1C(F)(F)F] | 9.34 (s, 2H), 9.24 (s, 1H), 8.92 (d, 1H), 7.95 (d, 1H), 7.70 (br.s, 1H), 2.59 (m, 1H), 1.32 (d, 6H) | 310.1 | — | — |
| C9 | 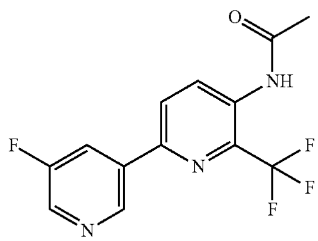 [SMILES: CC(=O)Nc1ccc(-c2cncc(F)c2)nc1C(F)(F)F] | 9.03 (d, 1H), 8.83 (d, 1H), 8.54 (d, 1H), 8.14 (m, 1H), 7.95 (d, 1H), 7.58 (br.s, 1H), 2.30 (s, 3H); | 299.1 | — | — |
| C10 | 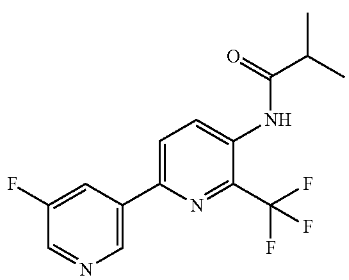 [SMILES: CC(C)C(=O)Nc1ccc(-c2cncc(F)c2)nc1C(F)(F)F] | 9.07 (br.s, 1H), 8.78 (d, 1H), 8.52 (1H, br. s), 8.12 (m, 1H), 7.92 (d, 1H), 7.67 (br.s, 1H), 2.58 (m, 1H), 1.31 (d, 6H) | 327.1 | — | — |
| C11 | 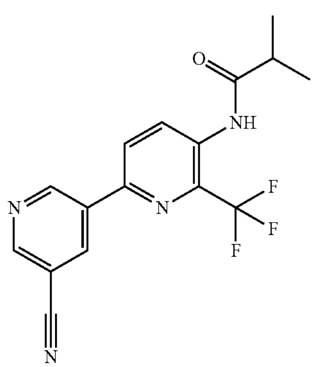 [SMILES: CC(C)C(=O)Nc1ccc(-c2cncc(C#N)c2)nc1C(F)(F)F] | 9.39 (s, 1H), 8.97 (d, 1H), 8.92 (d, 1H), 8.66 (d, 1H), 8.00 (d, 1H), 7.71 (br.s, 1H), 2.69-2.59 (m, 1H), 1.31 (d, 6H) | 334.1 | — | — |
| C12 | 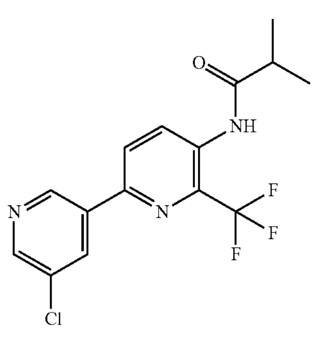 [SMILES: CC(C)C(=O)Nc1ccc(-c2cncc(Cl)c2)nc1C(F)(F)F] | 9.08 (d, 1H), 8.89 (d, 1H), 8.62 (d, 1H), 8.38 (d, 1H), 7.96 (d, 1H), 7.68 (br.s, 1H), 2.69-2.59 (m, 1H), 1.32 (d, 6H) | 343.1 | — | — |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C13 | 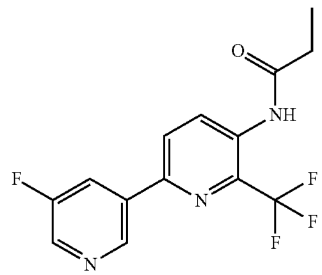 [SMILES: CCC(=O)Nc1ccc(-c2cncc(F)c2)nc1C(F)(F)F] | 9.10 (s, 1H), 8.90 (d, 1H), 8.55 (d, 1H), 8.15 (d, 1H), 8.00 (d, 1H), 7.61 (br.s, 1H), 2.51 (q, 2H), 1.30 (t, 3H) | 313.1 | — | — |
| C14 | 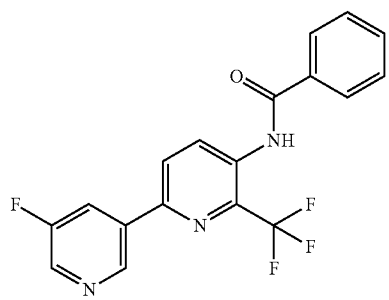 [SMILES: O=C(Nc1ccc(-c2cncc(F)c2)nc1C(F)(F)F)c1ccccc1] | 9.15 (m, 2H), 8.55 (d, 1H), 8.50 (s, 1H), 8.15 (d, 1H), 8.05 (d, 1H), 7.90 (m, 2H), 7.65-7.52 (m, 3H) | 361.1 | — | — |
| C15 | 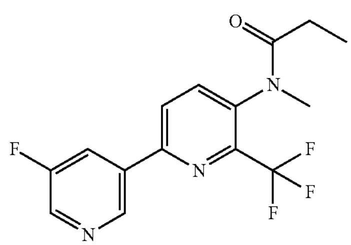 [SMILES: CCC(=O)N(C)c1ccc(-c2cncc(F)c2)nc1C(F)(F)F] | (major rotamer) 9.15 (s, 1H), 8.64 (m, 1H), 8.39 (m, 1H), 8.15 (d, 1H), 7.86 (d, 1H), 3.27 (s, 3H), 2.00 (2H, m), 1.08 (3H, t) | 327.1 | [MH]+ 328; tr 1.95 min | A |
| C16 | 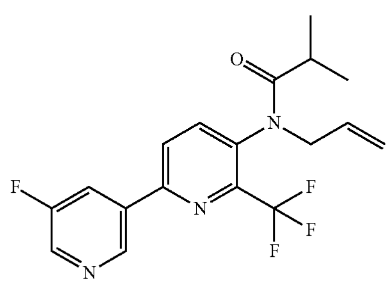 [SMILES: C=CCN(C(=O)C(C)C)c1ccc(-c2cncc(F)c2)nc1C(F)(F)F] | (CD₃OD, major rotamer) 9.21 (s, 1H), 8.83 (d, 1H), 8.40 (m, 2H), 8.06 (d, 1H), 5.93 (m, 1H), 5.23 (d, 1H), 5.15 (dd, 1H), 4.90 (m, 1H), 3.65 (dd, 1H), 2.20 (m, 1H), 1.05 (d, 3H), 1.03 (d, 3H) | 367.1 | [MH]+ 368; tr 0.74 mins | C |
| C17 | 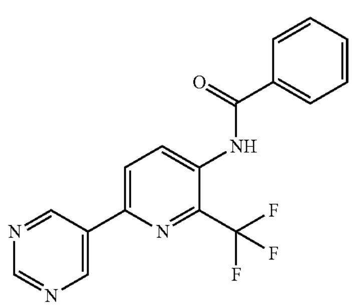 [SMILES: O=C(Nc1ccc(-c2cncnc2)nc1C(F)(F)F)c1ccccc1] | 9.45 (d, 2H), 9.30 (s, 1H), 9.15 (d, 1H), 8.47 (br. s, 1H), 8.05 (d, 1H), 7.90 (d, 2H), 7.65-7.52 (m, 3H) | 344.1 | — | — |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C18 | 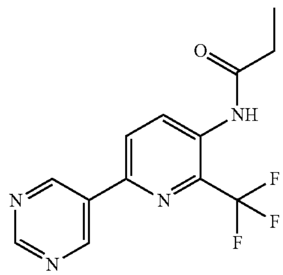 [SMILES: CCC(=O)Nc1ccc(-c2cncnc2)nc1C(F)(F)F] | 9.40 (s, 2H), 9.30 (s, 1H), 8.90 (d, 1H), 7.94 (d, 1H), 7.65 (br. s, 1H), 2.50 (q, 2H), 1.30 (t, 3H) | 296.1 | — | — |
| C19 | 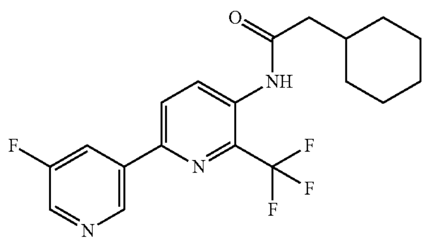 [SMILES: O=C(CC1CCCCC1)Nc1ccc(-c2cncc(F)c2)nc1C(F)(F)F] | 9.03 (s, 1H), 8.90 (d, 1H), 8.53 (d, 1H), 8.13 (m, 1H), 7.98 (d, 1H), 7.59 (br.s, 1H), 2.34 (d, 2H), 1.90 (m, 1H), 1.84-1.68 (m, 5H), 1.38-1.01 (m, 5H) | 381.1 | [MH]+ 382; tr 0.82 mins | C |
| C20 | 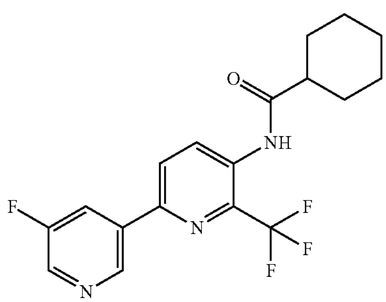 [SMILES: O=C(Nc1ccc(-c2cncc(F)c2)nc1C(F)(F)F)C1CCCCC1] | | 367.1 | [MH]+ 368; tr 0.77 mins | C |
| C21 | 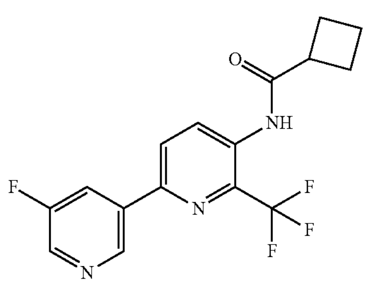 [SMILES: O=C(Nc1ccc(-c2cncc(F)c2)nc1C(F)(F)F)C1CCC1] | 9.03 (s, 1H), 8.91 (d, 1H), 8.53 (d, 1H), 8.12 (d, 1H), 7.98 (d, 1H), 7.57 (br.s, 1H), 3.28 (m, 1H), 2.46-2.31 (4H, m), 2.13-1.93 (2H, m) | 339.1 | [MH]+ 340; tr 0.65 mins | C |
| C22 | 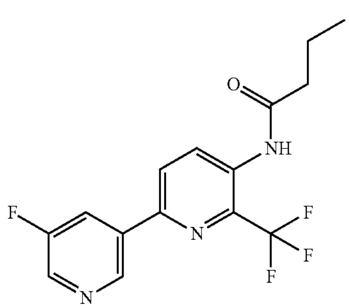 [SMILES: CCCC(=O)Nc1ccc(-c2cncc(F)c2)nc1C(F)(F)F] | 9.03 (d, 1H), 8.91 (d, 1H), 8.52 (d, 1H), 8.12 (m, 1H), 7.92 (d, 1H), 7.58 (br. s, 1H), 2.47 (t, 2H), 1.81 (m, 2H), 1.07 (t, 3H) | 327.1 | — | — |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C23 | 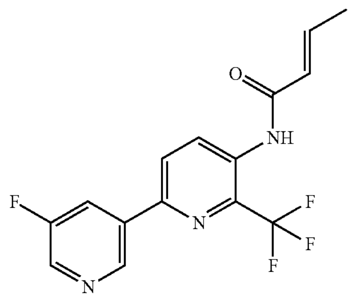 [SMILES: C/C=C/C(=O)Nc1ccc(-c2cncc(F)c2)nc1C(F)(F)F] | 9.04 (s, 1H), 8.99 (d, 1H), 8.54 (d, 1H), 8.14 (m, 1H), 8.00 (d, 1H), 7.62 (br.s, 1H), 7.09 (m, 1H), 6.05 (dd, 1H), 2.01 (dd, 3H) | 325.1 | — | — |
| C24 | 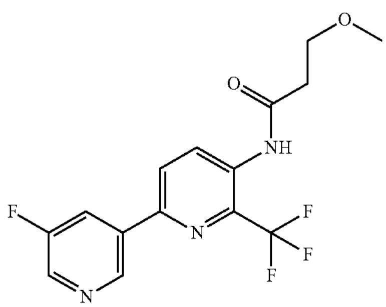 [SMILES: COCCC(=O)Nc1ccc(-c2cncc(F)c2)nc1C(F)(F)F] | 9.42 (br. s, 1H), 9.04 (s, 1H), 8.94 (d, 1H), 8.52 (d, 1H), 8.08 (m, 1H), 7.93 (d, 1H), 3.72 (t, 2H), 3.51 (s, 3H), 2.72 (t, 2H) | 343.1 | — | — |
| C25 | 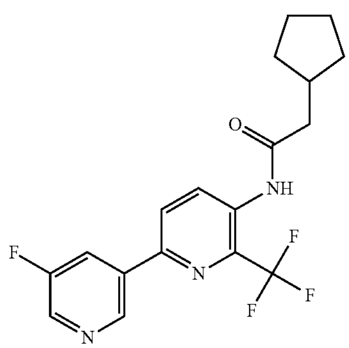 [SMILES: O=C(CC1CCCC1)Nc1ccc(-c2cncc(F)c2)nc1C(F)(F)F] | 9.03 (1H, app. dd), 8.93 (1H, d), 8.52 (1H. d), 8.11 (1H, m), 7.94 (1H, d), 7.58 (br. s, 1H), 2.48 (2H, app. t), 1.88-1.72 (3H, m), 1.68-1.55 (2H, m), 1.49-1.55 (2H, m), 1.07-1.16 (2H, m) | 367.1 | — | — |
| C26 | 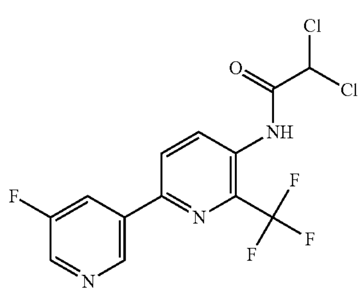 [SMILES: O=C(Nc1ccc(-c2cncc(F)c2)nc1C(F)(F)F)C(Cl)Cl] | 9.07 (s, 1H), 8.82 (m, 2H), 8.56 (d, 1H), 8.17 (dd, 1H), 8.05 (d, 1H), 6.13 (s, 1H) | 367.0 | — | — |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C27 | 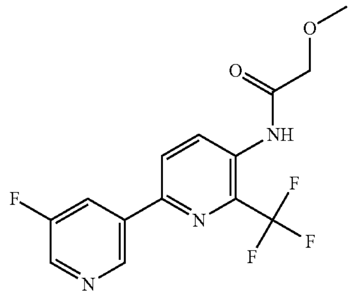 [SMILES: COCC(=O)Nc1ccc(-c2cncc(F)c2)nc1C(F)(F)F] | 9.12-8.93 (m, 3H), 8.52 (d, 1H), 8.12 (m, 1H), 7.96 (d, 1H), 4.11 (s, 2H), 3.56 (s, 3H) | 329.1 | — | — |
| C28 | 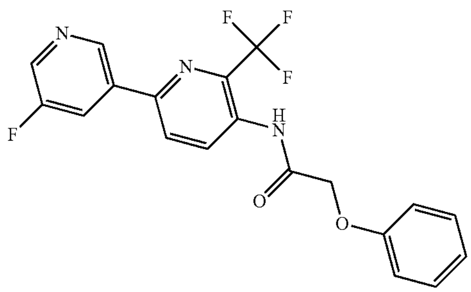 [SMILES: O=C(COc1ccccc1)Nc1ccc(-c2cncc(F)c2)nc1C(F)(F)F] | (major rotamer) 9.25 (br.s, 1H), 9.05 (d, 1H), 9.02 (s, 1H), 8.55 (d, 1H), 8.15 (m, 1H), 8.05 (d, 1H), 7.43 (m, 2H), 7.15 (m, 1H), 6.92 (m, 2H), 4.68 (s, 2H) | 391.1 | [MH]+ 392; tr 0.77 mins | C |
| C29 | 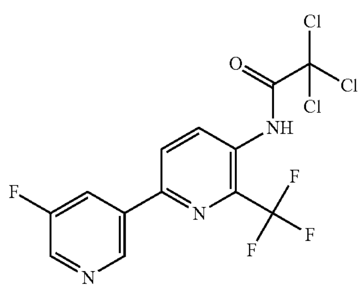 [SMILES: O=C(Nc1ccc(-c2cncc(F)c2)nc1C(F)(F)F)C(Cl)(Cl)Cl] | 9.05 (s, 1H), 9.01 (s, 1H), 8.78 (d, 1H), 8.58 (s, 1H), 8.12-8.03 (m, 2H) | 401.0 | [MH]+ 402; tr 0.74 mins | C |
| C30 | 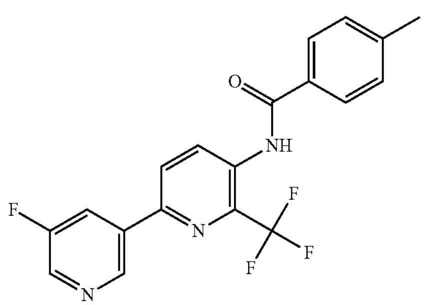 [SMILES: Cc1ccc(C(=O)Nc2ccc(-c3cncc(F)c3)nc2C(F)(F)F)cc1] | 9.11-9.06 (m, 2H), 8.55 (s, 1H), 8.42 (s, 1H), 8.15 (dd, 1H), 8.03 (d, 1H), 7.80 (d, 2H), 7.35 (d, 2H), 2.45 (s, 3H) | 375.1 | [MH]+ 376; tr 0.74 mins | C |
| C31 | 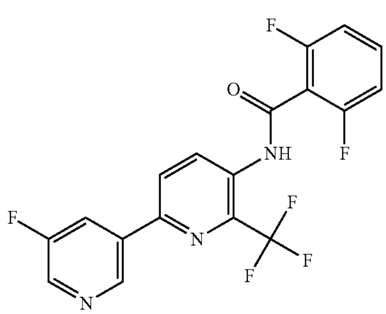 [SMILES: O=C(Nc1ccc(-c2cncc(F)c2)nc1C(F)(F)F)c1c(F)cccc1F] | | 397.1 | [MH]+ 398; tr 0.66 mins | C |

TABLE 2-continued

Characterising data for Compounds of formula (I) made by the methods described above

| Cmpd ID | Structure | $^1$H NMR Data (400 MHz, CDCl$_3$ unless stated) | Mass/ Da | Mass Spec | m/z Method |
|---|---|---|---|---|---|
| C33 | 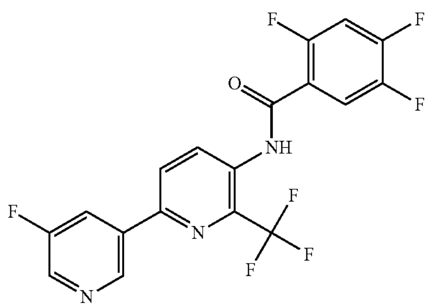 [SMILES: O=C(Nc1ccc(-c2cncc(F)c2)nc1C(F)(F)F)c1cc(F)c(F)cc1F] | 9.15 (br. d, 1H), 9.07 (s, 1H), 9.05 (d, 1H), 8.55 (d, 1H), 8.15 (dd, 1H), 8.10-8.05 (m, 2H), 7.15 (m, 1H) | 415.1 | | |
| C34 | 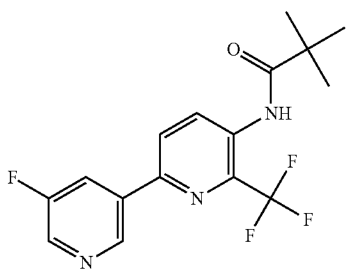 [SMILES: CC(C)(C)C(=O)Nc1ccc(-c2cncc(F)c2)nc1C(F)(F)F] | 9.05 (s, 1H), 8.80 (d, 1H), 8.55 (s, 1H), 8.15 (dd, 1H), 8.05 (m, 2H), 1.35 (s, 9H) | 341.1 | | |
| C35 | 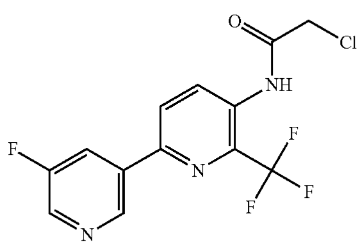 [SMILES: O=C(CCl)Nc1ccc(-c2cncc(F)c2)nc1C(F)(F)F] | 9.15 (s, 1H), 9.05 (br. s, 1H), 8.80 (d, 1H), 8.55 (s, 1H), 8.15 (dd, 1H), 8.05 (d, 1H), 4.30 (s, 2H) | 333.0 | | |
| C36 | 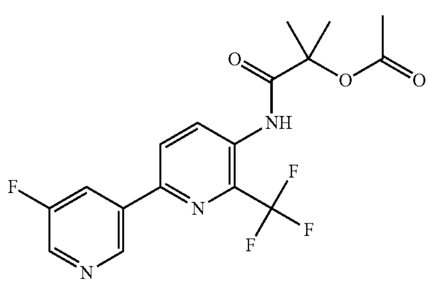 [SMILES: CC(=O)OC(C)(C)C(=O)Nc1ccc(-c2cncc(F)c2)nc1C(F)(F)F] | 9.10 (s, 1H), 8.95 (d, 1H), 8.55 (m, 2H), 8.15 (dd, 1H), 8.05 (d, 1H), 2.20 (s, 3H), 1.75 (s, 6H) | 385.1 | | |
| C37 | 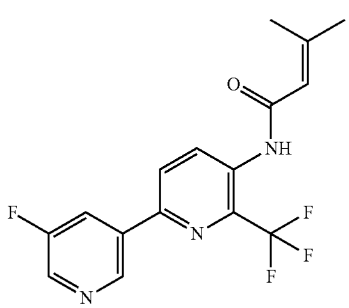 [SMILES: CC(C)=CC(=O)Nc1ccc(-c2cncc(F)c2)nc1C(F)(F)F] | 9.05 (s, 1H), 9.00 (d, 1H), 8.55 (s, 1H), 8.25 (dd, 1H), 8.05 (d, 1H), 7.55 (br. s, 1H), 5.75 (s, 1H), 2.30 (s, 3H), 2.00 (s, 3H) | 339.1 | | |

TABLE 2-continued

Characterising data for Compounds of formula (I) made by the methods described above

| Cmpd ID | Structure | $^1$H NMR Data (400 MHz, CDCl$_3$ unless stated) | Mass/ Da | Mass Spec | m/z Method |
|---|---|---|---|---|---|
| C38 | 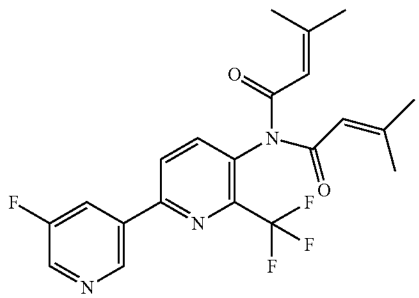 [SMILES: CC(C)=CC(=O)N(C(=O)C=C(C)C)c1ccc(-c2cncc(F)c2)nc1C(F)(F)F] | 9.15 (s, 1H), 8.65 (s, 1H), 8.35 (d, 1H), 8.10 (d, 1H), 7.80 (d, 1H), 6.00 (s, 2H), 2.15 (s, 6H), 1.90 (s, 6H) | 421.1 | | |
| C39 | 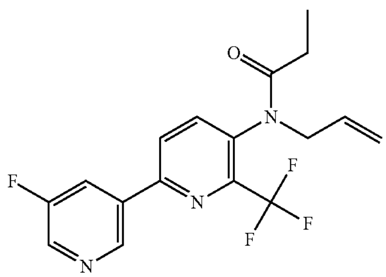 [SMILES: C=CCN(C(=O)CC)c1ccc(-c2cncc(F)c2)nc1C(F)(F)F] | | 353.1 | [MH]+ 354; tr 0.70 mins | C |
| C42 | 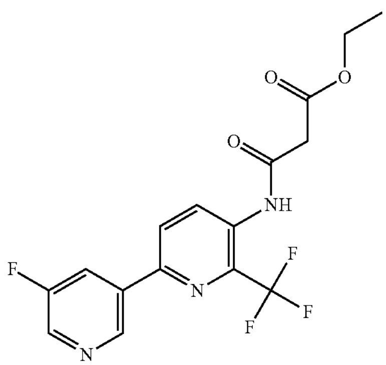 [SMILES: CCOC(=O)CC(=O)Nc1ccc(-c2cncc(F)c2)nc1C(F)(F)F] | 11.20 (s, 1H), 9.05 (s, 1H), 8.90 (d, 1H), 8.55 (d, 1H), 8.15 (dd, 1H), 8.05 (d, 1H), 4.40 (q, 2H), 3.55 (s, 2H), 1.35 (t, 3H) | 371.1 | | |
| C44 | 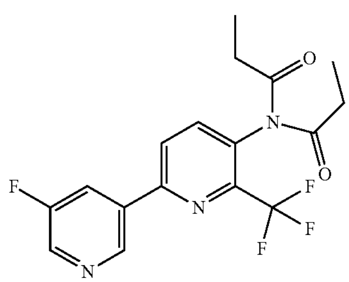 [SMILES: CCC(=O)N(C(=O)CC)c1ccc(-c2cncc(F)c2)nc1C(F)(F)F] | 9.08 (s, 1H), 8.59 (d, 1H), 8.24-8.19 (m, 1H), 8.11 (d, 1H), 7.78 (d, 1H), 2.50 (q, 4H), 1.15 (t, 6H) | 369.1 | | |
| C45 | 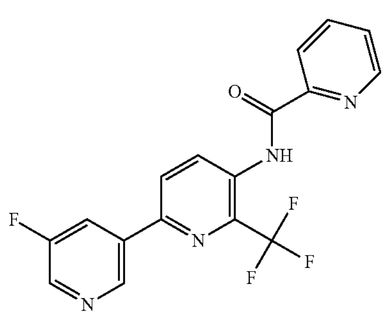 [SMILES: O=C(Nc1ccc(-c2cncc(F)c2)nc1C(F)(F)F)c1ccccn1] | (CD$_3$OD) 9.20 (s, 1H), 9.15 (s, 1H), 8.80 (d, 1H), 8.60 (d, 1H), 8.40 (m. 3H), 8.30 (d, 1H), 7.65 (m, 1H) | 362.1 | | |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C46 | 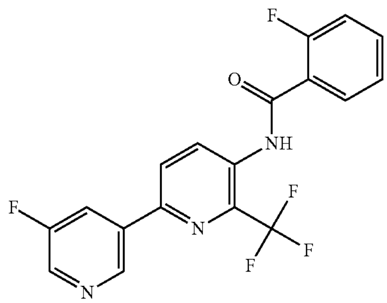 [SMILES: O=C(Nc1ccc(-c2cncc(F)c2)nc1C(F)(F)F)c1ccccc1F] | 9.25 (br, 1H), 9.10 (m, 2H), 8.55 (br. s, 1H), 8.25 (t, 1H), 8.15 (dd, 1H), 8.05 (d, 1H), 7.70 (m, 1H), 7.40 (t, 1H), 7.25 (t, 1H) | 379.1 | | |
| C47 | 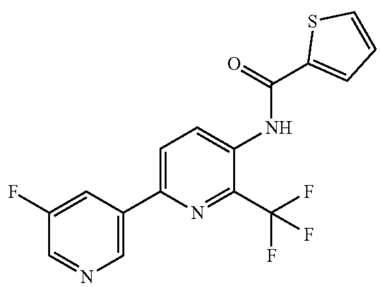 [SMILES: O=C(Nc1ccc(-c2cncc(F)c2)nc1C(F)(F)F)c1cccs1] | 9.05 (m, 2H), 8.55 (s, 1H), 8.3 (br. s, 1H), 8.20 (dd, 1H), 8.05 (d, 1H), 7.65 (m, 2H), 7.20 (m, 1H) | 367.0 | | |
| C49 | 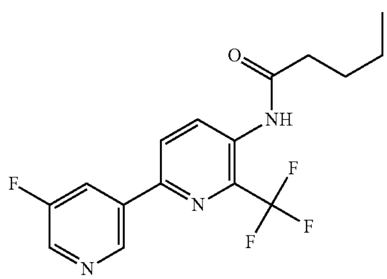 [SMILES: CCCCC(=O)Nc1ccc(-c2cncc(F)c2)nc1C(F)(F)F] | 9.10 (s, 1H), 8.95 (d, 1H), 8.55 (d, 1H), 8.15 (dd, 1H), 8.05 (d, 1H), 7.60 (br. s, 1H), 2.45 (t, 2H), 1.75 (m, 2H), 1.45 (m, 2H), 1.00 (t, 3H) | 341.1 | | |
| C50 | 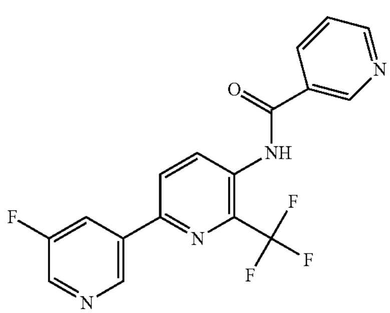 [SMILES: O=C(Nc1ccc(-c2cncc(F)c2)nc1C(F)(F)F)c1cccnc1] | 9.16 (s, 1H), 9.10-9.00 (m, 2H), 8.91-8.87 (m, 1H), 8.56 (d, 1H), 8.48 (br s, 1H), 8.25-8.20 (m, 1H), 8.20-8.13 (m, 1H), 8.07 (d, 1H), 7.56-7.50 (m, 1H). | 362.1 | | |
| C51 | 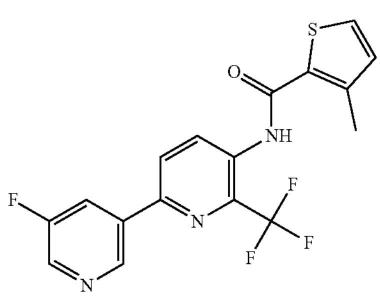 [SMILES: Cc1ccsc1C(=O)Nc1ccc(-c2cncc(F)c2)nc1C(F)(F)F] | 9.05 (m, 2H), 8.55 (s, 1H), 8.20 (m, 2H), 8.05 (d, 1H), 7.45 (d, 1H), 7.00 (d, 1H), 2.60 (s, 3H) | 381.1 | | |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C52 | 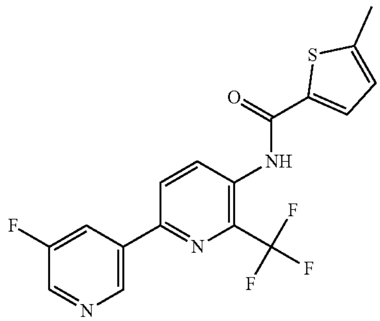 [SMILES: Cc1ccc(C(=O)Nc2ccc(-c3cncc(F)c3)nc2C(F)(F)F)s1] | 9.05 (m, 2H), 8.55 (s, 1H), 8.20 (m, 2H), 8.05 (d, 1H), 7.45 (d, 1H), 6.85 (d, 1H) 2.60 (s, 3H) | 381.1 | | |
| C53 | 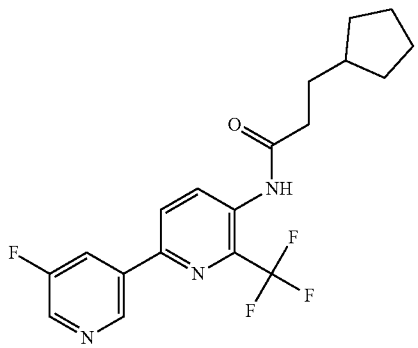 [SMILES: O=C(CCC1CCCC1)Nc1ccc(-c2cncc(F)c2)nc1C(F)(F)F] | 9.40 (br. s, 1H), 9.05 (s, 1H), 8.90 (d, 1H), 8.55 (s, 1H), 8.15 (dd, 1H), 7.90 (d, 1H), 2.50 (t, 2H), 1.90-1.75 (m, 4H), 1.70-1.50 (m, 5H), 1.15 (m, 2H) | 381.1 | | |
| C54 | 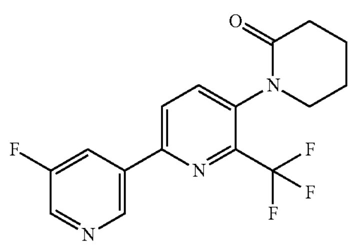 [SMILES: O=C1CCCCN1c1ccc(-c2cncc(F)c2)nc1C(F)(F)F] | 9.03 (s, 1H), 8.57 (s, 1H), 8.17 (d, 1H), 8.04 (d, 1H), 7.80 (d, 1H), 3.66-3.53 (m, 2H), 2.17-2.53 (m, 2H), 2.11-1.90 (m, 4H) | 339.1 | | |
| C55 | 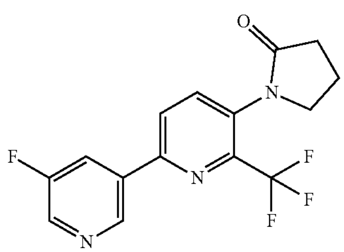 [SMILES: O=C1CCCN1c1ccc(-c2cncc(F)c2)nc1C(F)(F)F] | 9.03 (s, 1H), 8.58 (s, 1H), 8.17 (d, 1H), 8.03 (d, 1H), 7.83 (d, 1H), 3.80 (t, 2H), 2.61 (t, 2H), 2.31 (quintet, 2H). | 325.1 | | |
| C56 | 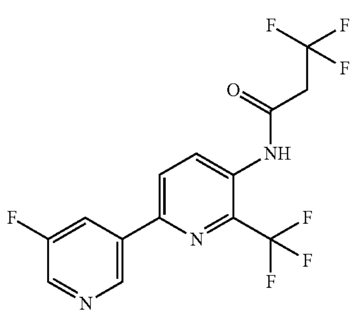 [SMILES: O=C(CC(F)(F)F)Nc1ccc(-c2cncc(F)c2)nc1C(F)(F)F] | (CD₃OD) 9.13 (br, 1H), 8.56 (br. s, 1H), 8.39-8.27 (m, 2H), 8.22 (d, 1H), 3.51 (q, 2H) | 367.1 | | |

TABLE 2-continued

Characterising data for Compounds of formula (I) made by the methods described above

| Cmpd ID | Structure | $^1$H NMR Data (400 MHz, CDCl$_3$ unless stated) | Mass/ Da | Mass Spec | m/z Method |
|---|---|---|---|---|---|
| C57 | 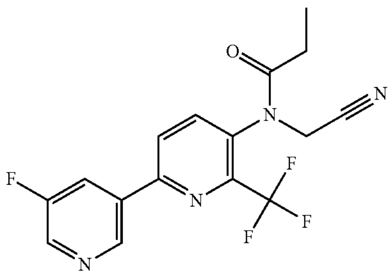 [SMILES: CCC(=O)N(CC#N)c1ccc(-c2cncc(F)c2)nc1C(F)(F)F] | (CD$_3$OD) 9.21 (s, 1H), 8.62 (d, 1H), 8.48 (d, 1H), 8.44-8.35 (m, 1H), 8.21 (d, 1H), 4.99 (d, 1H), 4.35 (d, 1H), 2.19-1.99 (m, 2H), 1.06 (t, 3H) | 352.1 | | |
| C58 | 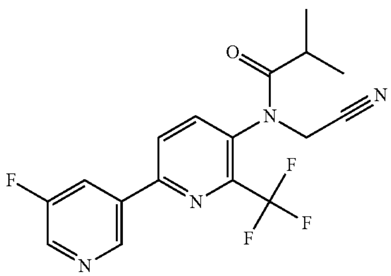 [SMILES: CC(C)C(=O)N(CC#N)c1ccc(-c2cncc(F)c2)nc1C(F)(F)F] | (CD$_3$OD) 9.12 (s, 1H), 8.62 (d, 1H), 8.29-8.13 (m, 2H), 8.08 (d, 1H), 5.35 (d, 1H), 3.88 (d, 1H), 2.33-2.19 (m, 1H), 1.18-1.01 (m, 6H) | 366.1 | | |
| C59 | 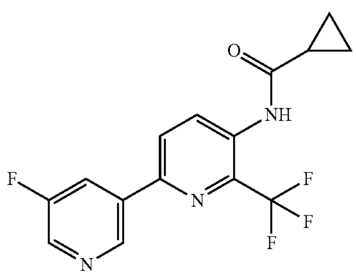 [SMILES: O=C(Nc1ccc(-c2cncc(F)c2)nc1C(F)(F)F)C1CC1] | 9.05 (s, 1H), 8.90 (d, 1H), 8.55 (s, 1H), 8.15 (d, 1H), 7.9 (s, 1H), 7.80 (bs, 1H), 1.60 (m, 1H), 1.15 (m, 2H), 0.95 (m, 2H) | 325.1 | | |
| C60 | 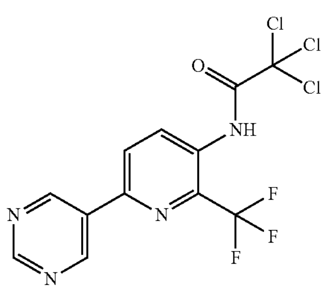 [SMILES: O=C(Nc1ccc(-c2cncnc2)nc1C(F)(F)F)C(Cl)(Cl)Cl] | 9.42 (s, 2H), 9.31 (s, 1H), 8.97 (br. s, 1H), 8.79 (d, 1H), 8.03 (d, 1H) | 384.0 | | |
| C61 | 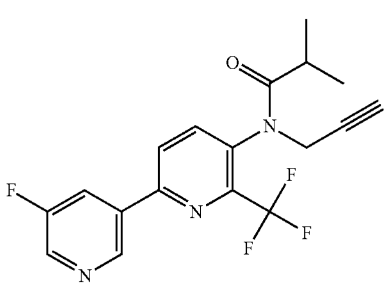 [SMILES: C#CCN(C(=O)C(C)C)c1ccc(-c2cncc(F)c2)nc1C(F)(F)F] | 9.12 (s, 1H), 8.61 (d, 1H), 8.32-8.24 (m, 1H), 8.16 (d, 1H), 8.03 (d, 1H), 5.23 (dd, 1H), 3.79 (dd, 1H), 2.31-2.27 (m, 1H), 2.27-2.16 (m, 1H), 1.08 (dd, 6H) | 365.1 | | |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C62 | 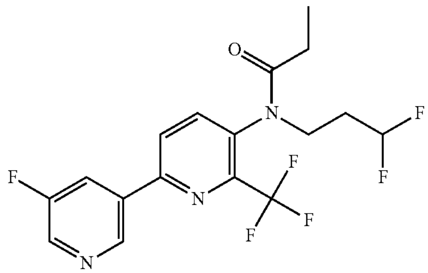 [SMILES: CCC(=O)N(CCC(F)F)c1ccc(-c2cncc(F)c2)nc1C(F)(F)F] | 9.01 (s, 1H), 8.51 (d, 1H), 8.19-8.12 (m, 1H), 7.90 (d, 1H), 7.30-7.22 (m, 1H), 6.02 (tt, 1H), 4.41 (t, 2H), 2.41-2.26 (m, 2H), 2.19 (q, 2H), 1.12 (t, 3H) | 391.1 | | |
| C63 | 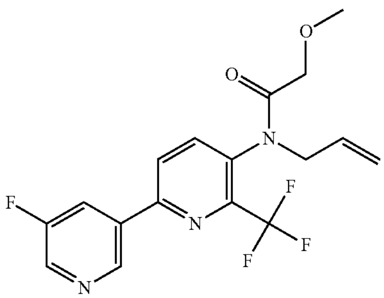 [SMILES: C=CCN(C(=O)COC)c1ccc(-c2cncc(F)c2)nc1C(F)(F)F] | | 369.1 | [MH]+ 370; tr 0.61 mins | C |
| C65 | 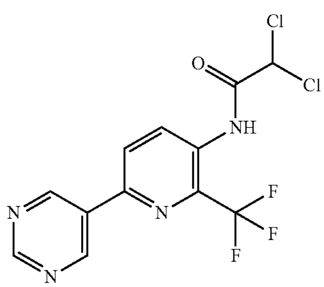 [SMILES: O=C(Nc1ccc(-c2cncnc2)nc1C(F)(F)F)C(Cl)Cl] | 9.43 (s, 2H), 9.31 (s, 1H), 8.92 (br. s, 1H), 8.81 (d, 1H), 8.02 (d, 1H), 6.17 (s, 1H) | 350.0 | | |
| C66 | 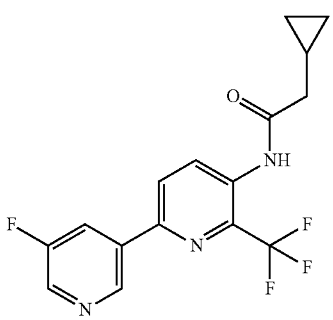 [SMILES: O=C(CC1CC1)Nc1ccc(-c2cncc(F)c2)nc1C(F)(F)F] | 9.05 (s, 1H), 9.00 (d, 1H), 8.57 (br.s, 1H), 8.53 (d, 1H), 8.16 (m, 1H), 8.00 (d, 1H), 2.45 (d, 2H), 1.08 (m, 1H), 0.83 (m, 2H), 0.38 (m, 2H) | 339.1 | | |
| C67 | 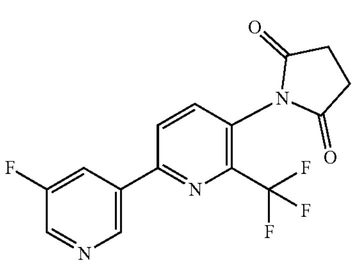 [SMILES: O=C1CCC(=O)N1c1ccc(-c2cncc(F)c2)nc1C(F)(F)F] | (CD₃OD) 9.19 (s, 1H), 8.62 (d, 1H), 8.45 (d, 1H), 8.41-8.31 (m, 1H), 8.05 (d, 1H), 2.97 (app. s, 4H) | 339.1 | | |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C68 | 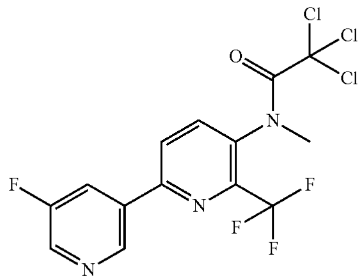 [SMILES: CN(C(=O)C(Cl)(Cl)Cl)c1ccc(-c2cncc(F)c2)nc1C(F)(F)F] | 9.07 (s, 1H), 8.60 (d, 1H), 8.20 (m, 1H), 8.10 (d, 1H), 7.88 (br. s, 1H), 3.70 (br. s, 3H) | 415.0 | | |
| C69 | 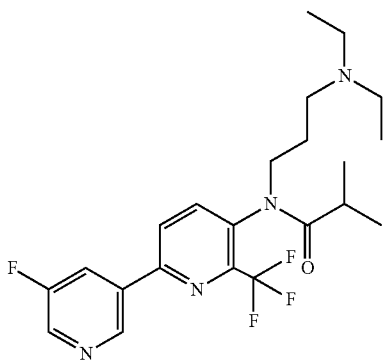 [SMILES: CCN(CC)CCCN(C(=O)C(C)C)c1ccc(-c2cncc(F)c2)nc1C(F)(F)F] | | 440.2 | [MH]+ 441; tr 1.01 mins | A |
| C70 | 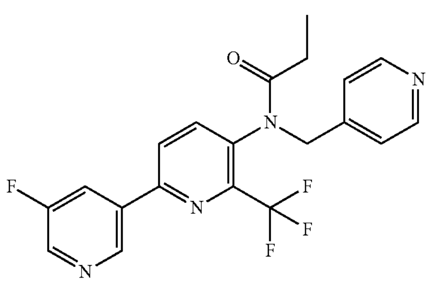 [SMILES: CCC(=O)N(Cc1ccncc1)c1ccc(-c2cncc(F)c2)nc1C(F)(F)F] | | 404.1 | [MH]+ 405; tr 0.90 mins | A |
| C71 | 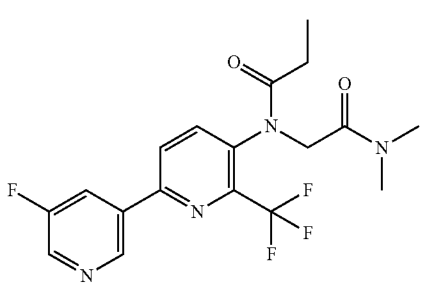 [SMILES: CCC(=O)N(CC(=O)N(C)C)c1ccc(-c2cncc(F)c2)nc1C(F)(F)F] | | 398.1 | [MH]+ 399; tr 1.07 mins | A |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C72 | 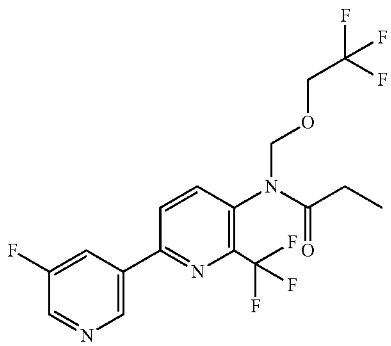 [SMILES: CCC(=O)N(COCC(F)(F)F)c1ccc(-c2cncc(F)c2)nc1C(F)(F)F] | | 425.1 | [MH]+ 426; tr 1.40 mins | A |
| C73 | 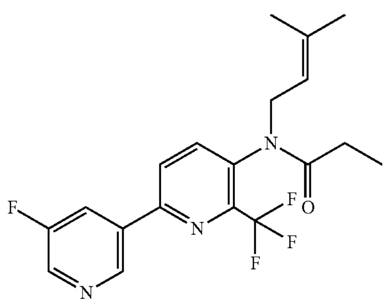 [SMILES: CCC(=O)N(CC=C(C)C)c1ccc(-c2cncc(F)c2)nc1C(F)(F)F] | | 381.1 | [MH]+ 382; tr 1.42 mins | A |
| C74 | 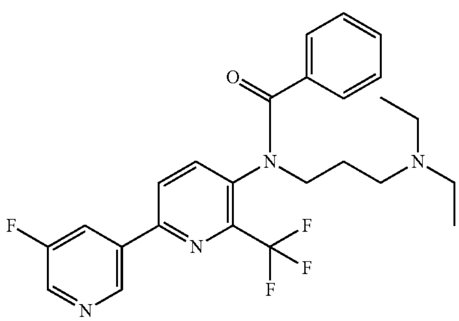 [SMILES: CCN(CC)CCCN(C(=O)c1ccccc1)c1ccc(-c2cncc(F)c2)nc1C(F)(F)F] | | 474.2 | [MH]+ 475; tr 0.99 mins | A |
| C75 | 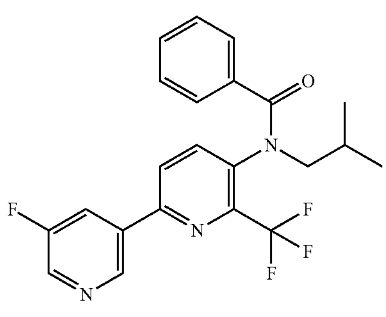 [SMILES: CC(C)CN(C(=O)c1ccccc1)c1ccc(-c2cncc(F)c2)nc1C(F)(F)F] | | 417.1 | [MH]+ 418; tr 1.49 mins | A |

TABLE 2-continued

*Characterising data for Compounds of formula (I) made by the methods described above*

| Cmpd ID | Structure | ¹H NMR Data (400 MHz, CDCl₃ unless stated) | Mass/ Da | Mass Spec | m/z Method |
|---|---|---|---|---|---|
| C76 | 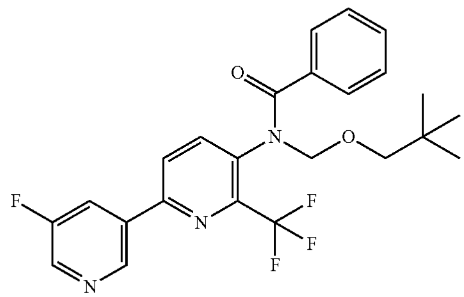 [SMILES: CC(C)(C)COCN(C(=O)c1ccccc1)c1ccc(-c2cncc(F)c2)nc1C(F)(F)F] | | 461.2 | [MH]+ 462; tr 1.67 mins | A |
| C77 | 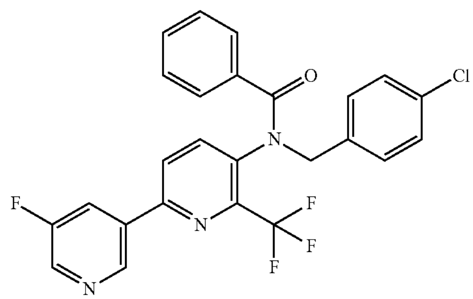 [SMILES: O=C(c1ccccc1)N(Cc1ccc(Cl)cc1)c1ccc(-c2cncc(F)c2)nc1C(F)(F)F] | | 485.1 | [MH]+ 486; tr 1.57 mins | A |
| C78 | 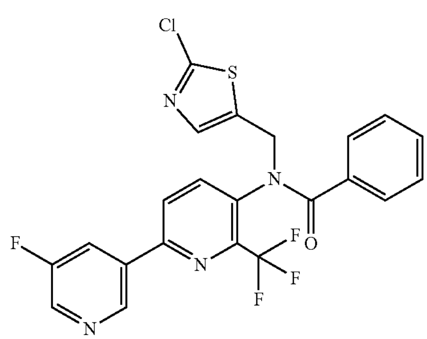 [SMILES: O=C(c1ccccc1)N(Cc1cnc(Cl)s1)c1ccc(-c2cncc(F)c2)nc1C(F)(F)F] | | 492.0 | [MH]+ 493; tr 1.45 mins | A |
| C79 | 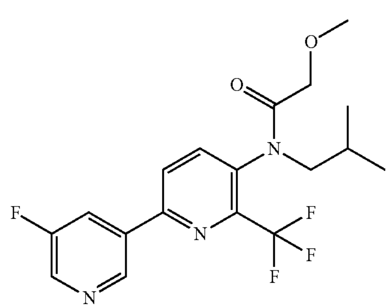 [SMILES: COCC(=O)N(CC(C)C)c1ccc(-c2cncc(F)c2)nc1C(F)(F)F] | | 385.1 | [MH]+ 386; tr 1.27 mins | A |

TABLE 2-continued

*Characterising data for Compounds of formula (I) made by the methods described above*

| Cmpd ID | Structure | ¹H NMR Data (400 MHz, CDCl₃ unless stated) | Mass/ Da | Mass Spec | m/z Method |
|---|---|---|---|---|---|
| C80 | 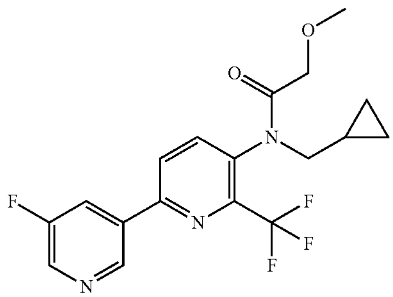 [SMILES: COCC(=O)N(CC1CC1)c1ccc(-c2cncc(F)c2)nc1C(F)(F)F] | | 383.1 | [MH]+ 384; tr 1.21 mins | A |
| C81 | 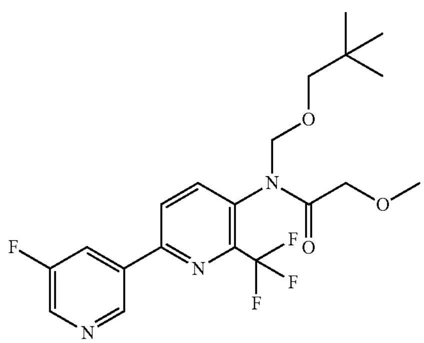 [SMILES: COCC(=O)N(COCC(C)(C)C)c1ccc(-c2cncc(F)c2)nc1C(F)(F)F] | | 429.2 | [MH]+ 430; tr 1.47 mins | A |
| C82 | 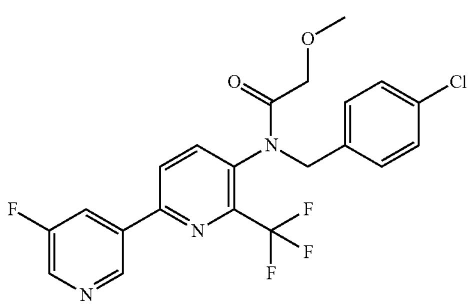 [SMILES: COCC(=O)N(Cc1ccc(Cl)cc1)c1ccc(-c2cncc(F)c2)nc1C(F)(F)F] | | 453.1 | [MH]+ 454; tr 1.40 mins | A |
| C83 | 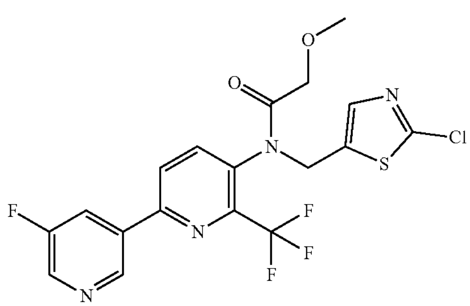 [SMILES: COCC(=O)N(Cc1cnc(Cl)s1)c1ccc(-c2cncc(F)c2)nc1C(F)(F)F] | | 460.0 | [MH]+ 461; tr 1.25 mins | A |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C84 | 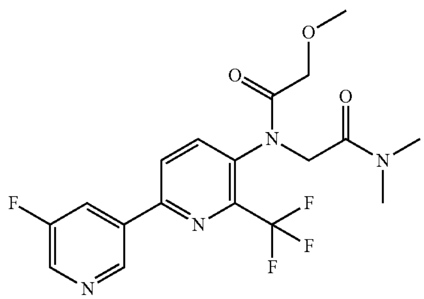 [SMILES: COCC(=O)N(CC(=O)N(C)C)c1ccc(-c2cncc(F)c2)nc1C(F)(F)F] | | 414.1 | [MH]+ 415; tr 0.97 mins | A |
| C85 | 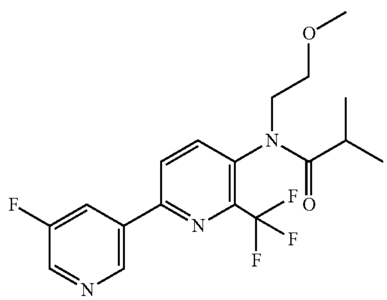 [SMILES: COCCN(C(=O)C(C)C)c1ccc(-c2cncc(F)c2)nc1C(F)(F)F] | | 385.1 | [MH]+ 386; tr 1.27 mins | A |
| C86 | 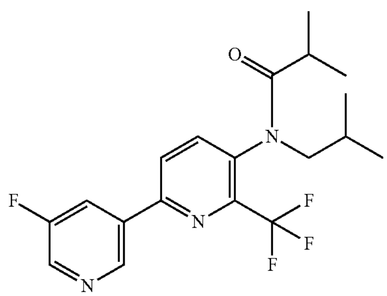 [SMILES: CC(C)CN(C(=O)C(C)C)c1ccc(-c2cncc(F)c2)nc1C(F)(F)F] | | 383.2 | [MH]+ 384; tr 1.46 mins | A |
| C87 | 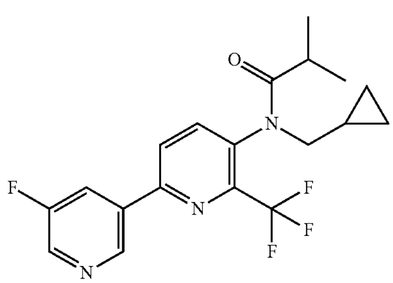 [SMILES: CC(C)C(=O)N(CC1CC1)c1ccc(-c2cncc(F)c2)nc1C(F)(F)F] | | 381.1 | [MH]+ 382; tr 1.40 mins | A |
| C88 | 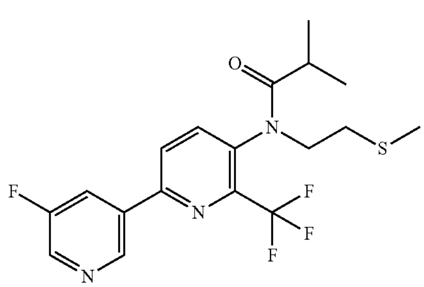 [SMILES: CSCCN(C(=O)C(C)C)c1ccc(-c2cncc(F)c2)nc1C(F)(F)F] | | 401.1 | [MH]+ 402; tr 1.39 mins | A |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C89 | 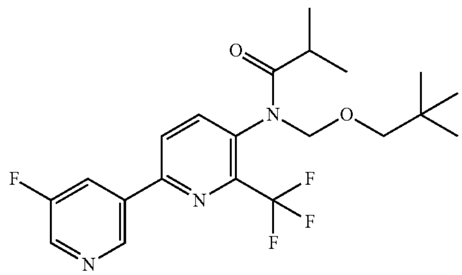 [SMILES: CC(C)C(=O)N(COCC(C)(C)C)c1ccc(-c2cncc(F)c2)nc1C(F)(F)F] | | 427.2 | [MH]+ 428; tr 1.65 mins | A |
| C90 | 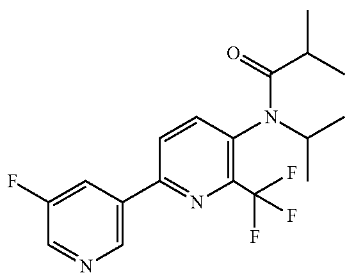 [SMILES: CC(C)C(=O)N(c1ccc(-c2cncc(F)c2)nc1C(F)(F)F)C(C)C] | | 369.1 | [MH]+ 370; tr 1.36 mins | A |
| C91 | 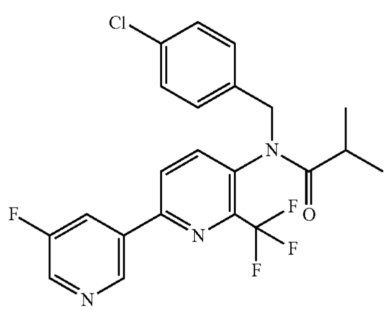 [SMILES: CC(C)C(=O)N(Cc1ccc(Cl)cc1)c1ccc(-c2cncc(F)c2)nc1C(F)(F)F] | | 451.1 | [MH]+ 452; tr 1.57 mins | A |
| C92 | 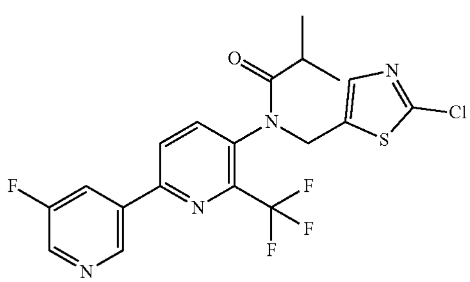 [SMILES: CC(C)C(=O)N(Cc1cnc(Cl)s1)c1ccc(-c2cncc(F)c2)nc1C(F)(F)F] | | 458.1 | [MH]+ 459; tr 1.46 mins | A |
| C93 | 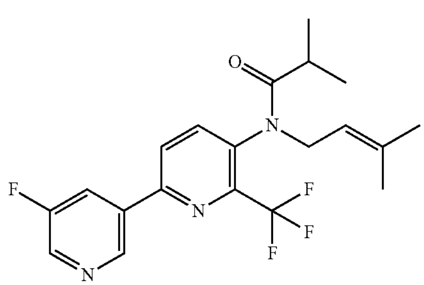 [SMILES: CC(C)=CCN(C(=O)C(C)C)c1ccc(-c2cncc(F)c2)nc1C(F)(F)F] | | 395.2 | [MH]+ 396; tr 1.48 mins | A |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C94 | 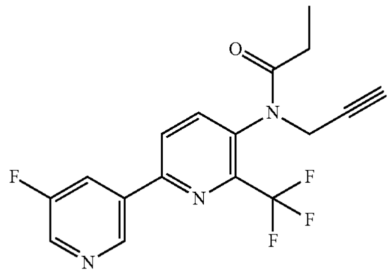 [SMILES: C#CCN(C(=O)CC)c1ccc(-c2cncc(F)c2)nc1C(F)(F)F] | | 351.1 | [MH]+ 352; tr 1.24 mins | A |
| C95 | 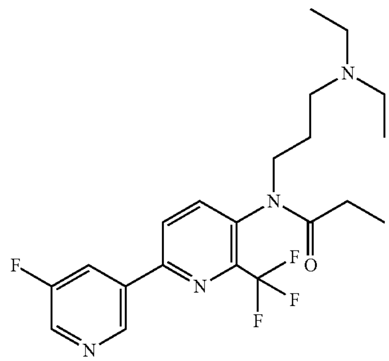 [SMILES: CCC(=O)N(CCCN(CC)CC)c1ccc(-c2cncc(F)c2)nc1C(F)(F)F] | | 426.2 | [MH]+ 427; tr 0.94 mins | A |
| C96 | 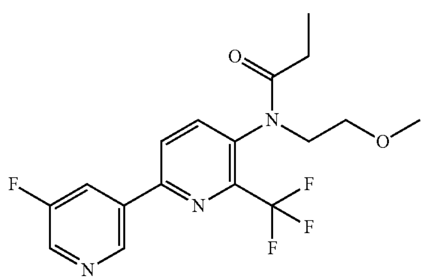 [SMILES: CCC(=O)N(CCOC)c1ccc(-c2cncc(F)c2)nc1C(F)(F)F] | | 371.1 | [MH]+ 372; tr 1.18 mins | A |
| C97 | 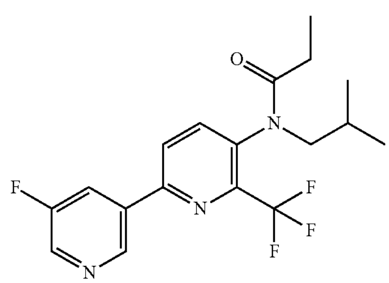 [SMILES: CCC(=O)N(CC(C)C)c1ccc(-c2cncc(F)c2)nc1C(F)(F)F] | | 369.1 | [MH]+ 370; tr 1.39 mins | A |
| C98 | 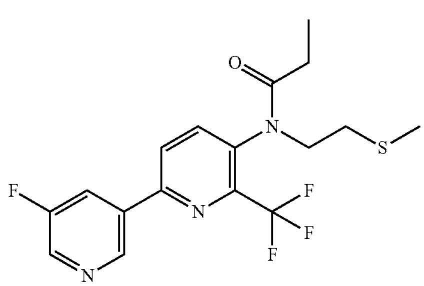 [SMILES: CCC(=O)N(CCSC)c1ccc(-c2cncc(F)c2)nc1C(F)(F)F] | | 387.1 | [MH]+ 388; tr 1.32 mins | A |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C99 | 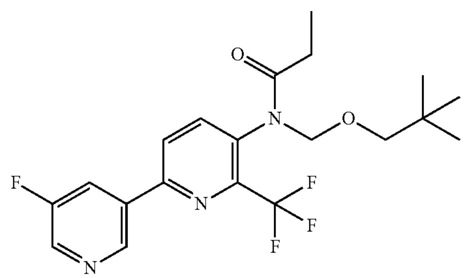 [SMILES: CCC(=O)N(COCC(C)(C)C)c1ccc(-c2cncc(F)c2)nc1C(F)(F)F] | | 413.2 | [MH]+ 414; tr 1.59 mins | A |
| C100 | 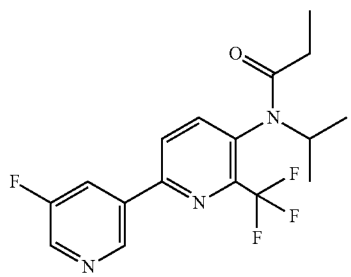 [SMILES: CCC(=O)N(c1ccc(-c2cncc(F)c2)nc1C(F)(F)F)C(C)C] | | 355.1 | [MH]+ 356; tr 1.28 mins | A |
| C101 | 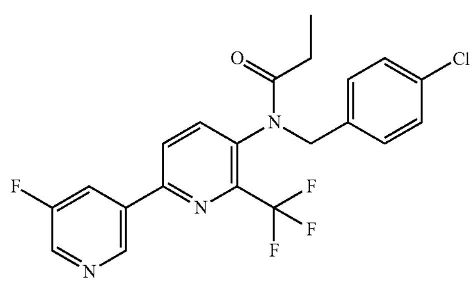 [SMILES: CCC(=O)N(Cc1ccc(Cl)cc1)c1ccc(-c2cncc(F)c2)nc1C(F)(F)F] | | 437.1 | [MH]+ 438; tr 1.51 mins | A |
| C102 | 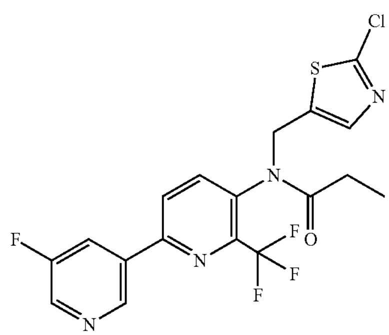 [SMILES: CCC(=O)N(Cc1cnc(Cl)s1)c1ccc(-c2cncc(F)c2)nc1C(F)(F)F] | | 444.0 | [MH]+ 445; tr 1.39 mins | A |
| C103 | 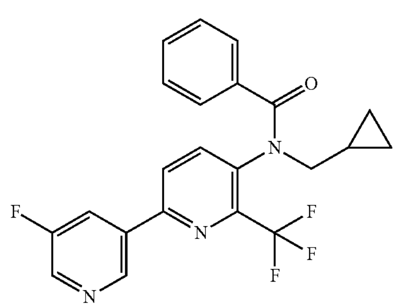 [SMILES: O=C(c1ccccc1)N(CC1CC1)c1ccc(-c2cncc(F)c2)nc1C(F)(F)F] | | 415.1 | [MH]+ 416; tr 1.41 mins | A |

TABLE 2-continued

Characterising data for Compounds of formula (I) made by the methods described above

| Cmpd ID | Structure | $^1$H NMR Data (400 MHz, CDCl$_3$ unless stated) | Mass/ Da | Mass Spec | m/z Method |
|---|---|---|---|---|---|
| C104 | 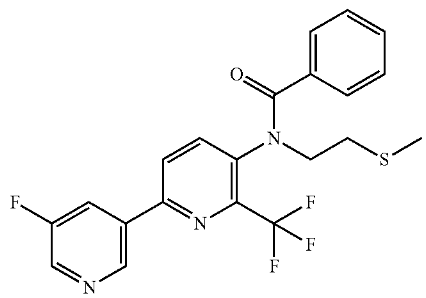 [SMILES: CSCCN(C(=O)c1ccccc1)c1ccc(-c2cncc(F)c2)nc1C(F)(F)F] | | 435.1 | [MH]+ 436; tr 1.40 mins | A |
| C105 | 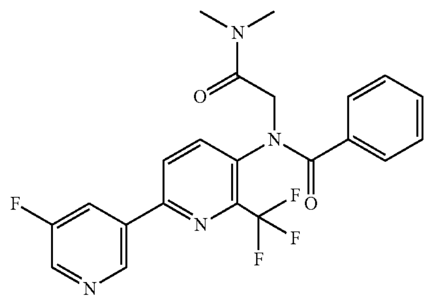 [SMILES: CN(C)C(=O)CN(C(=O)c1ccccc1)c1ccc(-c2cncc(F)c2)nc1C(F)(F)F] | | 446.1 | [MH]+ 447; tr 1.17 mins | A |
| C106 | 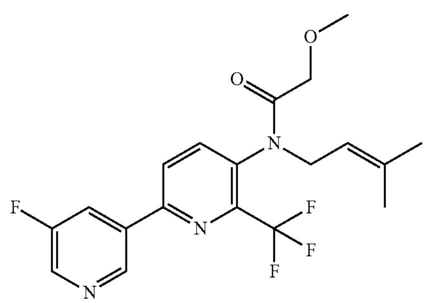 [SMILES: COCC(=O)N(CC=C(C)C)c1ccc(-c2cncc(F)c2)nc1C(F)(F)F] | | 397.1 | [MH]+ 398; tr 1.30 mins | A |
| C107 | 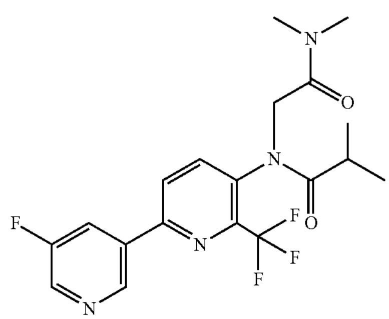 [SMILES: CC(C)C(=O)N(CC(=O)N(C)C)c1ccc(-c2cncc(F)c2)nc1C(F)(F)F] | | 412.2 | [MH]+ 413; tr 1.15 mins | A |
| C108 | 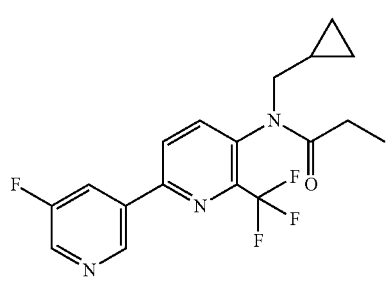 [SMILES: CCC(=O)N(CC1CC1)c1ccc(-c2cncc(F)c2)nc1C(F)(F)F] | | 367.1 | [MH]+ 368; tr 1.32 mins | A |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C109 | 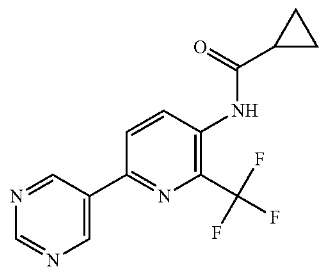 [SMILES: O=C(Nc1ccc(-c2cncnc2)nc1C(F)(F)F)C1CC1] | 9.33 (s, 2H), 9.26 (s, 1H), 8.92 (d, 1H), 7.94 (d, 1H), 7.82 (br.s, 1H), 1.58 (m, 1H), 1.18 (m, 2H), 0.94 (m, 2H) | 308.1 | | |
| C110 | 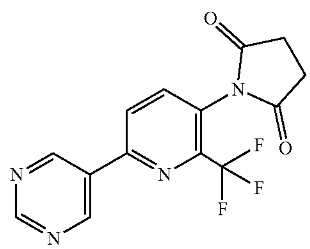 [SMILES: O=C1CCC(=O)N1c1ccc(-c2cncnc2)nc1C(F)(F)F] | 9.46 (s, 2H), 9.28 (s, 1H), 8.05 (d, 1H), 7.78 (d, 1H), 3.15-2.87 (m, 4H) | 322.1 | | |
| C111 | 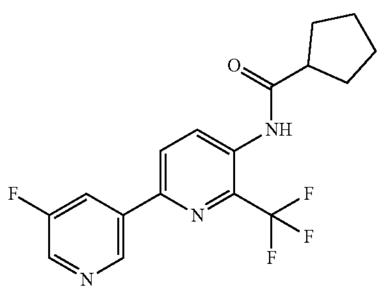 [SMILES: O=C(Nc1ccc(-c2cncc(F)c2)nc1C(F)(F)F)C1CCCC1] | 9.03 (t, 1H), 8.90 (d, 1H), 8.53 (d, 1H), 8.15-8.10 (m, 1H), 7.97 (d, 1H), 7.66 (br.s, 1H), 2.81 (t, 1H), 2.10-1.98 (m, 2H), 1.97-1.87 (m, 2H), 1.85-1.77 (m, 2H), 1.69 (br. dd, 2H) | 353.1 | | |
| C112 | 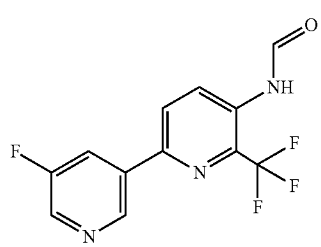 [SMILES: O=CNc1ccc(-c2cncc(F)c2)nc1C(F)(F)F] | 8.98 (s, 1H), 8.89 (d, 1H), 8.52-8.46 (m, 2H), 8.11-8.04 (m, 1H), 7.92 (d, 1H), 7.70-7.63 (m, 1H) | 285.1 | | |
| C113 | 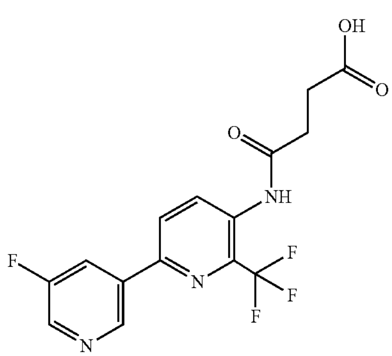 [SMILES: O=C(O)CCC(=O)Nc1ccc(-c2cncc(F)c2)nc1C(F)(F)F] | (CD₃OD) 9.14 (dd, 1H), 8.55 (d, 1H), 8.32-8.24 (m, 3H), 2.75 (m, 2H), 2.70 (m, 2H) | 357.1 | | |

TABLE 2-continued

Characterising data for Compounds of formula (I) made by the methods described above

| Cmpd ID | Structure | ¹H NMR Data (400 MHz, CDCl₃ unless stated) | Mass/ Da | Mass Spec | m/z Method |
|---|---|---|---|---|---|
| C114 | 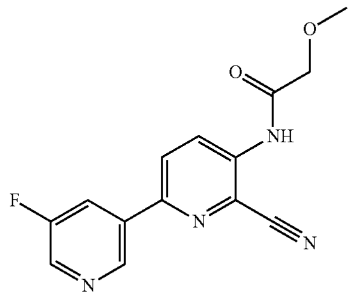 [SMILES: COCC(=O)Nc1ccc(-c2cncc(F)c2)nc1C#N] | 9.12 (br. s, 1H), 9.02 (s, 1H), 9.00 (d, 1H), 8.55 (d, 1H), 8.09 (m, 1H), 8.00 (d, 1H), 4.13 (s, 2H), 3.60 (s, 3H) | 286.1 | | |
| C115 | 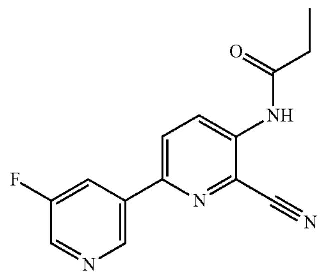 [SMILES: CCC(=O)Nc1ccc(-c2cncc(F)c2)nc1C#N] | (CD₃OD) 9.08 (s, 1H), 8.55 (d, 1H), 8.34-8.25 (m, 3H), 2.54 (q, 2H), 1.25 (t, 3H) | 270.1 | | |
| C116 | 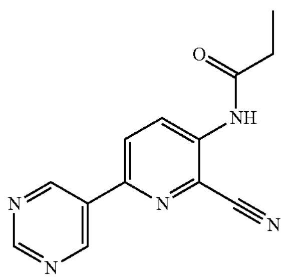 [SMILES: CCC(=O)Nc1ccc(-c2cncnc2)nc1C#N] | (CD₃OD) 9.41 (s, 2H), 9.22 (s, 1H), 8.39 (d, 1H), 8.28 (d, 1H), 2.57 (q, 2H), 1.25 (t, 3H) | 253.1 | | |
| C117 | 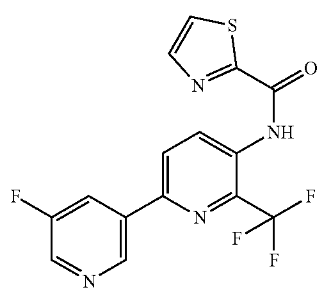 [SMILES: O=C(Nc1ccc(-c2cncc(F)c2)nc1C(F)(F)F)c1nccs1] | 9.12-9.05 (m, 2H), 8.99 (d, 1H), 8.58 (d, 1H), 8.44 (s, 1H), 8.30-8.21 (m, 2H), 8.07 (d, 1H) | 368.0 | | |
| C119 | 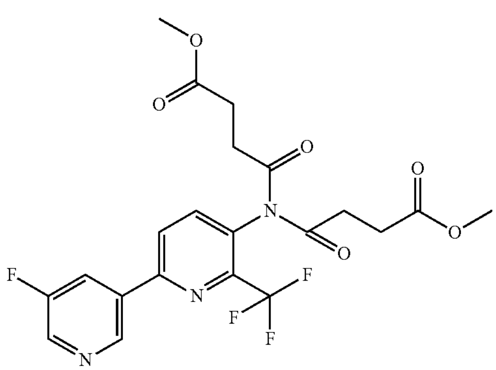 [SMILES: COC(=O)CCC(=O)N(C(=O)CCC(=O)OC)c1ccc(-c2cncc(F)c2)nc1C(F)(F)F] | 9.13 (t, 1H), 8.64 (d 1H), 8.36-8.30 (m, 1H), 8.16 (d, 1H), 7.98 (d, 1H), 3.70 (s, 6H), 2.93-2.86 (m, 4H), 2.78-2.56 (m, 4H) | 485.1 | | |

TABLE 2-continued

Characterising data for Compounds of formula (I) made by the methods described above

| Cmpd ID | Structure | $^1$H NMR Data (400 MHz, CDCl$_3$ unless stated) | Mass/Da | Mass Spec | m/z Method |
|---|---|---|---|---|---|
| C120 | 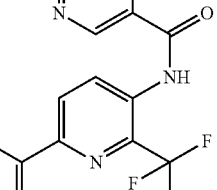 | 9.48 (s, 1H), 9.27 (s, 2H), 9.09 (t, 1H), 9.00 (d, 1H), 8.59 (d, 1H), 8.33 (br. s, 1H), 8.25-8.17 (m, 1H), 8.10 (d, 1H) | 363.1 | | |
| C121 | 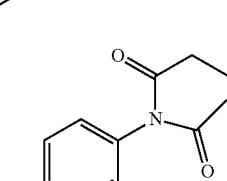 | 9.08 (t, 1H), 8.60 (d, 1H), 8.21 (m, 1H), 8.11 (d, 1H), 7.77 (d, 1H), 2.52 (m, 2H), 2.40 (s, 3H), 1.14 (t, 3H) | 355.1 | | |

Physical Characterisation

Compounds of the invention were characterised using one or more of the following methods.

NMR

NMR spectra contained herein were recorded on either a 400 MHz Bruker AVANCE III HD equipped with a Bruker SMART probe or a 500 MHz Bruker AVANCE III equipped with a Bruker Prodigy probe. Chemical shifts are expressed as ppm downfield from TMS, with an internal reference of either TMS or the residual solvent signals. The following multiplicities are used to describe the peaks: s=singlet, d=doublet, t=triplet, dd=double doublet, m=multiplet. Additionally br. is used to describe a broad signal and app. is used to describe an apparent multiplicity.

LCMS

LCMS data contained herein consists of the molecular ion [MH+] and the retention time (tr) of the peak recorded on the chromatogram. The following instruments, methods and conditions were used to obtain LCMS data:

Method A

Instrumentation: Waters Acquity UPLC-MS using a Sample Organizer with Sample Manager FTN, H-Class QSM, Column Manager, 2× Column Manager Aux, Photodiode Array (Wavelength range (nm): 210 to 400, ELSD and SQD 2 equipped with a Waters HSS T3 C18 column (column length 30 mm, internal diameter of column 2.1 mm, particle size 1.8 micron).

Ionisation Method:

Electrospray positive and negative: Capillary (kV) 3.00, Cone (V) 30.00, Source Temperature (° C.) 500, Cone Gas Flow (L/Hr.) 10, Desolvation Gas Flow (L/Hr.) 1000. Mass range (Da): positive 95 to 800, negative 115 to 800.

The analysis was conducted using a two minute run time, according to the following gradient table at 40° C.:

| Time (mins) | Solvent A (%) | Solvent B (%) | Flow (ml/mn) |
|---|---|---|---|
| 0.00 | 95.0 | 5.0 | 0.7 |
| 1.75 | 0.0 | 100 | 0.7 |
| 1.76 | 0.0 | 100 | 0.7 |
| 2.0 | 0.0 | 5.0 | 0.7 |
| 2.01 | 95.0 | 5.0 | 0.7 |
| 2.11 | 95.0 | 5.0 | 0.7 |

Solvent A: H$_2$O with 0.05% TFA
Solvent B: CH$_3$CN with 0.05% TFA

Method B (2 Min Method)

Instrumentation:

Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

LC-Method:

Phenomenex 'Kinetex C18 100A' column (50 mm×4.6 mm, particle size 2.6 micron), Flow rate: 2 mL/min at 313K (40 Celsius), Gradient (Solvent A: H$_2$O with 0.1% Formic Acid; Solvent B: Acetonitrile with 0.1% Formic Acid):

The analysis was conducted using a two minute run time, according to the following gradient table at 40° C.

| Time (mins) | Solvent A (%) | Solvent B (%) | Flow (ml/mn) |
|---|---|---|---|
| Initial | 70.0 | 30.0 | 2.000 |
| 1.20 | 10.0 | 90.0 | 2.000 |
| 1.70 | 10.0 | 90.0 | 2.000 |
| 1.80 | 70.0 | 30.0 | 2.000 |
| 2.00 | 70.0 | 30.0 | 2.000 |
| 2.20 | 70.0 | 30.0 | 2.000 |

Method C (1 Min Method)

Instrumentation:

Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

LC-Method:

Phenomenex 'Kinetex C18 100A' column (50 mm×4.6 mm, particle size 2.6 micron), Flow rate: 2 mL/min at 313K (40 Celsius), Gradient (Solvent A: $H_2O$ with 0.1% Formic Acid; Solvent B: Acetonitrile with 0.1% Formic Acid):

The analysis was conducted using a one minute run time, according to the following gradient table at 40° C.

| Time (mins) | Solvent A (%) | Solvent B (%) | Flow (ml/mn) |
|---|---|---|---|
| Initial | 60.0 | 40.0 | 2.000 |
| 0.80 | 0.0 | 100.0 | 2.000 |
| 0.95 | 0.0 | 100.0 | 2.000 |
| 1.00 | 60.0 | 40.0 | 2.000 |
| 1.10 | 60.0 | 40.0 | 2.000 |
| 1.25 | 60.0 | 40.0 | 2.000 |

BIOLOGICAL EXAMPLES

B1 Pre-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), *Zea Mays* (ZEAMX), *Abutilon theophrasti* (ABUTH), *Amaranthus retroflexus* (AMARE) and *Setaria fabenr* (SETFA). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone I water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B1a and B1b.

Tables B1a and B1b Control of Weed Species by Compound of Formula (I) after Pre-Emergence Application TABLE B1a

| | | Test 1a | | | | | |
|---|---|---|---|---|---|---|---|
| Compound ID | Rate (g/ha) | LOLPE | SETFA | ALOMY | ECHCG | AVEFA | TRAZW |
| C1 | 1000 | 1 | 5 | 0 | 5 | 2 | 1 |
| C2 | 1000 | 1 | 5 | 0 | 3 | 0 | 0 |
| C3 | 1000 | 1 | 5 | 0 | 4 | 0 | 0 |
| C4 | 1000 | 5 | 1 | 0 | 4 | 1 | 0 |
| C5 | 1000 | 1 | 5 | 1 | 4 | 3 | 0 |
| C6 | 1000 | 2 | 4 | 1 | 4 | 4 | 1 |
| C7 | 1000 | 1 | 4 | 0 | 4 | 3 | 0 |
| C8 | 1000 | 2 | 5 | 0 | 4 | 3 | 0 |
| C11 | 1000 | 1 | 4 | 0 | 1 | 0 | 0 |
| C12 | 1000 | 1 | 4 | 0 | 2 | 0 | 0 |
| C13 | 1000 | 3 | 5 | 1 | 4 | 2 | 0 |
| C14 | 1000 | 2 | 4 | 2 | 5 | 1 | 0 |
| C15 | 1000 | 1 | 5 | 0 | 5 | 0 | 0 |
| C16 | 1000 | 2 | 5 | 0 | 4 | 1 | 0 |
| C17 | 1000 | 1 | 5 | 0 | 4 | 3 | 0 |
| C19 | 1000 | 0 | 5 | 0 | 3 | 2 | 0 |
| C20 | 1000 | 0 | 5 | 0 | 4 | 2 | 0 |
| C21 | 1000 | 1 | 5 | 0 | 4 | 2 | 0 |
| C22 | 1000 | 1 | 5 | 0 | 4 | 2 | 0 |
| C23 | 1000 | 1 | 5 | 1 | 5 | 3 | 1 |
| C24 | 1000 | 1 | 5 | 1 | 4 | 4 | 0 |
| C26 | 1000 | 1 | 5 | 0 | 5 | 2 | 0 |
| C27 | 1000 | 1 | 5 | 0 | 5 | 3 | 0 |
| C28 | 1000 | 1 | 4 | 0 | 4 | 3 | 0 |
| C29 | 1000 | 1 | 5 | 0 | 5 | 4 | 0 |
| C30 | 1000 | 1 | 5 | 2 | 5 | 3 | 0 |
| C31 | 1000 | 0 | 5 | 1 | 4 | 2 | 0 |
| C33 | 1000 | 1 | 2 | 0 | 1 | 1 | 0 |
| C34 | 1000 | 0 | 5 | 0 | 2 | 0 | 0 |
| C35 | 1000 | 1 | 4 | 0 | 4 | 1 | 0 |
| C36 | 1000 | 1 | 4 | 0 | 4 | 1 | 0 |
| C37 | 1000 | 1 | 5 | 0 | 4 | 1 | 0 |
| C38 | 1000 | 0 | 5 | 0 | 4 | 0 | 0 |
| C39 | 1000 | 1 | 5 | 0 | 4 | 2 | 0 |
| C40 | 1000 | 0 | 3 | 0 | 1 | 0 | 0 |
| C42 | 1000 | 1 | 4 | 0 | 4 | 2 | 0 |
| C44 | 1000 | 1 | 4 | 0 | 5 | 2 | 0 |
| C45 | 1000 | 1 | 4 | 0 | 5 | 2 | 0 |
| C46 | 1000 | 1 | 4 | 0 | 2 | 1 | 0 |
| C47 | 1000 | 1 | 4 | 1 | 5 | 2 | 0 |
| C49 | 1000 | 1 | 5 | 1 | 5 | 2 | 0 |
| C50 | 1000 | 1 | 4 | 0 | 3 | 1 | 0 |
| C51 | 1000 | 0 | 4 | 0 | 3 | 0 | 0 |
| C52 | 1000 | 1 | 5 | 1 | 4 | 1 | 0 |
| C53 | 1000 | 1 | 4 | 1 | 5 | 3 | 0 |
| C54 | 1000 | 1 | 3 | 0 | 2 | 1 | 0 |
| C55 | 1000 | 1 | 4 | 0 | 1 | 1 | 0 |
| C56 | 1000 | 0 | 4 | 0 | 3 | 1 | 0 |
| C57 | 1000 | 0 | 4 | 0 | 3 | 1 | 0 |
| C58 | 1000 | 0 | 5 | 0 | 3 | 0 | 0 |
| C59 | 1000 | 1 | 5 | 0 | 4 | 3 | 0 |
| C60 | 1000 | 0 | 5 | 0 | 3 | 2 | 0 |
| C61 | 1000 | 0 | 5 | 0 | 3 | 1 | 0 |
| C62 | 1000 | 1 | 4 | 0 | 3 | 2 | 0 |
| C63 | 1000 | 1 | 4 | 0 | 2 | 0 | 0 |
| C65 | 1000 | 2 | 3 | 0 | 4 | 3 | 0 |
| C67 | 1000 | 0 | 2 | 0 | 1 | 0 | 0 |
| C69 | 1000 | 0 | 5 | 0 | 3 | 1 | 0 |
| C70 | 1000 | 1 | 2 | 0 | 2 | 1 | 0 |
| C71 | 1000 | 1 | 5 | 0 | 4 | 1 | 1 |
| C72 | 1000 | 0 | 4 | 0 | 1 | 0 | 0 |
| C73 | 1000 | 0 | 5 | 0 | 4 | 2 | 0 |
| C74 | 1000 | 1 | 3 | 1 | 1 | 0 | 0 |
| C76 | 1000 | 0 | 5 | 0 | 1 | 0 | 0 |
| C77 | 1000 | 0 | 1 | 0 | 0 | 0 | 0 |
| C78 | 1000 | 0 | 2 | 0 | 1 | 0 | 0 |
| C79 | 1000 | 2 | 5 | 0 | 3 | 1 | 0 |
| C80 | 1000 | 0 | 3 | 0 | 2 | 0 | 0 |
| C81 | 1000 | 2 | 5 | 0 | 3 | 1 | 0 |
| C82 | 1000 | 0 | 1 | 0 | 1 | 0 | 0 |
| C83 | 1000 | 1 | 4 | 0 | 2 | 1 | 0 |
| C84 | 1000 | 1 | 5 | 0 | 2 | 1 | 0 |
| C85 | 1000 | 0 | 2 | 0 | 2 | 0 | 0 |
| C86 | 1000 | 0 | 1 | 0 | 0 | 0 | 0 |

TABLE B1a-continued

Test 1a

| Compound ID | Rate (g/ha) | LOLPE | SETFA | ALOMY | ECHCG | AVEFA | TRAZW |
|---|---|---|---|---|---|---|---|
| C87 | 1000 | 0 | 5 | 0 | 2 | 0 | 0 |
| C88 | 1000 | 0 | 2 | 0 | 1 | 0 | 0 |
| C89 | 1000 | 0 | 4 | 0 | 3 | 1 | 0 |
| C90 | 1000 | 0 | 2 | 0 | 2 | 0 | 0 |
| C94 | 1000 | 1 | 5 | 0 | 2 | 1 | 0 |
| C95 | 1000 | 1 | 4 | 0 | 3 | 1 | 0 |
| C96 | 1000 | 0 | 5 | 1 | 3 | 1 | 0 |
| C97 | 1000 | 0 | 3 | 0 | 1 | 0 | 0 |
| C98 | 1000 | 1 | 3 | 0 | 1 | 0 | 0 |
| C99 | 1000 | 1 | 5 | 0 | 2 | 1 | 0 |
| C100 | 1000 | 1 | 5 | 0 | 3 | 1 | 0 |
| C101 | 1000 | 0 | 1 | 0 | 1 | 1 | 0 |
| C102 | 1000 | 0 | 4 | 0 | 2 | 1 | 0 |
| C103 | 1000 | 0 | 1 | 0 | 0 | 0 | 0 |
| C104 | 250 | 0 | 3 | 0 | 0 | 0 | 0 |
| C106 | 1000 | 1 | 4 | 0 | 3 | 2 | 0 |
| C107 | 1000 | 0 | 5 | 0 | 3 | 1 | 0 |
| C108 | 1000 | 1 | 5 | 0 | 2 | 1 | 0 |
| C109 | 1000 | 1 | 4 | 0 | 4 | 2 | 0 |
| C110 | 1000 | 1 | 4 | 0 | 4 | 3 | 0 |
| C111 | 1000 | 1 | 5 | 1 | 4 | 2 | 0 |
| C112 | 1000 | 1 | 4 | 1 | 3 | 2 | 0 |
| C113 | 1000 | 1 | 5 | 0 | 5 | 2 | 0 |
| C114 | 1000 | 0 | 5 | 0 | 4 | 1 | 0 |
| C115 | 1000 | 1 | 5 | 0 | 5 | 0 | 0 |
| C116 | 1000 | 0 | 5 | 0 | 3 | 1 | NT |
| C117 | 250 | 0 | 2 | 0 | 1 | 0 | 0 |
| C119 | 1000 | 1 | 5 | 0 | 5 | 2 | 0 |
| C120 | 1000 | 1 | 5 | 0 | 4 | 3 | 0 |
| C121 | 250 | 1 | 5 | 0 | 3 | 2 | 0 |

TABLE B1b

Test 1b

| Compound ID | Rate (g/ha) | LOLPE | AMARE | SETFA | ECHCG | ZEAMX | ABUTH |
|---|---|---|---|---|---|---|---|
| C9 | 1000 | 2 | 2 | 4 | 3 | 5 | 1 |
| C10 | 1000 | 2 | 0 | 4 | 4 | 5 | 1 |

B2 Post-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), *Zea Mays* (ZEAMX), *Abutilon theophrasti* (ABUTH), *Amaranthus retroflexus* (AMARE) and *Setaria fabenri* (SETFA). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone I water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B2a and B2b.

Tables B2a and B2b Control of Weed Species by Compound of Formula (I) after Post-Emergence Application

TABLE B2a

Test 2a

| Compound ID | Rate (g/ha) | LOLPE | SETFA | ALOMY | ECHCG | AVEFA | TRAZW |
|---|---|---|---|---|---|---|---|
| C1 | 1000 | 4 | 5 | 1 | 5 | 3 | 1 |
| C2 | 1000 | 2 | 5 | 1 | 5 | 3 | 1 |
| C3 | 1000 | 3 | 5 | 1 | 5 | 3 | 1 |
| C4 | 1000 | 5 | 3 | 1 | 4 | 4 | 1 |
| C5 | 1000 | 4 | 5 | 1 | 4 | 4 | 0 |
| C6 | 1000 | 4 | 5 | 1 | 4 | 4 | 1 |
| C7 | 1000 | 3 | 5 | 1 | 4 | 4 | 1 |
| C8 | 1000 | 2 | 5 | 3 | 4 | 4 | 2 |
| C11 | 1000 | 1 | 5 | 1 | 3 | 2 | 0 |
| C12 | 1000 | 2 | 5 | 1 | 5 | 3 | 0 |
| C13 | 1000 | 4 | 5 | 1 | 5 | 4 | 0 |
| C14 | 1000 | 4 | 5 | 1 | 5 | 4 | 1 |
| C15 | 1000 | 3 | 5 | 1 | 5 | 3 | 1 |
| C16 | 1000 | 3 | 5 | 1 | 5 | 4 | 1 |
| C17 | 1000 | 2 | NT | 0 | 5 | 3 | 0 |
| C19 | 1000 | 1 | NT | 0 | 4 | 3 | 0 |
| C20 | 1000 | 2 | NT | 0 | 4 | 3 | 0 |
| C21 | 1000 | 2 | NT | 0 | 5 | 3 | 0 |
| C22 | 1000 | 2 | NT | 0 | 4 | 3 | 0 |
| C23 | 1000 | 3 | 5 | 0 | 5 | 3 | 0 |
| C24 | 1000 | 4 | 5 | 1 | 5 | 4 | 1 |
| C26 | 1000 | 4 | 5 | 0 | 5 | 4 | 1 |
| C27 | 1000 | 3 | 5 | 1 | 5 | 4 | 1 |
| C28 | 1000 | 3 | 5 | 0 | 5 | 4 | 0 |
| C29 | 1000 | 3 | 5 | 0 | 5 | 4 | 0 |
| C30 | 1000 | 3 | 5 | 0 | 5 | 4 | 0 |
| C31 | 1000 | 3 | 5 | 0 | 5 | 3 | 0 |
| C33 | 1000 | 1 | 3 | 0 | 2 | 2 | 0 |
| C34 | 1000 | 2 | 5 | 1 | 4 | 3 | 1 |
| C35 | 1000 | 2 | 5 | 0 | 5 | 3 | 0 |
| C36 | 1000 | 1 | 5 | 0 | 5 | 2 | 1 |
| C37 | 1000 | 2 | 5 | 0 | 5 | 3 | 0 |
| C38 | 1000 | 2 | 5 | 0 | 4 | 3 | 0 |
| C39 | 1000 | 2 | 5 | 0 | 5 | 3 | 1 |
| C40 | 1000 | 2 | 5 | 0 | 3 | 3 | 0 |
| C42 | 1000 | 2 | 5 | 0 | 5 | 4 | 1 |
| C44 | 1000 | 3 | 5 | 1 | 5 | 3 | 0 |
| C45 | 1000 | 2 | 5 | 0 | 5 | 2 | 1 |
| C46 | 1000 | 1 | 4 | 0 | 3 | 2 | 0 |
| C47 | 1000 | 3 | 5 | 1 | 5 | 4 | 0 |
| C49 | 1000 | 3 | 5 | 1 | 5 | 4 | 0 |
| C50 | 1000 | 1 | 4 | 1 | 2 | 3 | 0 |
| C51 | 1000 | 1 | 4 | 0 | 2 | 2 | 0 |
| C52 | 1000 | 2 | 5 | 0 | 4 | 4 | 0 |
| C53 | 1000 | 4 | 5 | 0 | 5 | 4 | 1 |
| C54 | 1000 | 3 | 4 | 1 | 5 | 3 | 0 |
| C55 | 1000 | 2 | 4 | 1 | 4 | 3 | 0 |
| C56 | 1000 | 2 | 4 | 0 | 4 | 3 | 1 |
| C57 | 1000 | 2 | 4 | 0 | 4 | 2 | 0 |
| C58 | 1000 | 1 | 5 | 0 | 4 | 2 | 0 |
| C59 | 1000 | 3 | 4 | 1 | 5 | 3 | 0 |
| C60 | 1000 | 3 | 4 | 0 | 4 | 3 | 0 |
| C61 | 1000 | 2 | 4 | 1 | 4 | 2 | 0 |
| C62 | 1000 | 2 | 5 | 1 | 5 | 4 | 1 |
| C63 | 1000 | 2 | 4 | 1 | 4 | 2 | 0 |
| C65 | 1000 | 3 | 5 | 0 | 5 | 4 | 0 |
| C67 | 1000 | 2 | 4 | 0 | 4 | 2 | 0 |
| C69 | 1000 | NT | 4 | 0 | 3 | NT | 0 |
| C70 | 1000 | 1 | 3 | 0 | 2 | 2 | 0 |
| C71 | 1000 | NT | 5 | 0 | 4 | NT | 0 |
| C72 | 1000 | NT | 3 | 0 | 2 | NT | 0 |
| C73 | 1000 | NT | 5 | 0 | 4 | NT | 0 |
| C74 | 1000 | NT | 3 | 0 | 2 | NT | 0 |
| C76 | 1000 | NT | 4 | 0 | 3 | NT | 1 |
| C77 | 1000 | NT | 2 | 0 | 1 | NT | 0 |
| C78 | 1000 | NT | 3 | 0 | 1 | NT | 0 |
| C79 | 1000 | NT | 3 | 0 | 3 | NT | 0 |
| C80 | 1000 | 1 | 5 | 1 | 3 | 2 | 1 |
| C81 | 1000 | NT | 5 | 0 | 4 | NT | 0 |
| C82 | 1000 | NT | 2 | 0 | 1 | NT | 0 |

TABLE B2a-continued

Test 2a

| Compound ID | Rate (g/ha) | LOLPE | SETFA | ALOMY | ECHCG | AVEFA | TRAZW |
|---|---|---|---|---|---|---|---|
| C83 | 1000 | NT | 3 | 0 | 2 | NT | 0 |
| C84 | 1000 | NT | 4 | 1 | 3 | NT | 0 |
| C85 | 1000 | 1 | 4 | 0 | 4 | 2 | 1 |
| C86 | 1000 | NT | 1 | 0 | 1 | NT | 0 |
| C87 | 1000 | NT | 4 | 0 | 3 | NT | 0 |
| C88 | 1000 | 1 | 2 | 1 | 1 | 1 | 1 |
| C89 | 1000 | NT | 4 | 0 | 4 | NT | 0 |
| C90 | 1000 | 1 | 4 | 0 | 4 | 2 | 1 |
| C94 | 1000 | 2 | 5 | 0 | 4 | 2 | 0 |
| C95 | 1000 | 2 | 5 | 1 | 5 | 2 | 1 |
| C96 | 1000 | NT | 4 | 0 | 3 | NT | 0 |
| C97 | 1000 | NT | 3 | 0 | 2 | NT | 0 |
| C98 | 1000 | NT | 0 | 0 | 1 | NT | 0 |
| C99 | 1000 | 2 | 5 | 0 | 4 | 2 | 0 |
| C100 | 1000 | NT | 5 | 0 | 4 | NT | 0 |
| C101 | 1000 | NT | 2 | 0 | 2 | NT | 0 |
| C102 | 1000 | NT | 2 | 0 | 2 | NT | 0 |
| C103 | 1000 | 1 | 2 | 0 | 1 | 2 | 0 |
| C104 | 250 | NT | 2 | 0 | 1 | NT | 0 |
| C106 | 1000 | NT | 5 | 0 | 4 | NT | 0 |
| C107 | 1000 | NT | 5 | 0 | 4 | NT | 0 |
| C108 | 1000 | NT | 4 | 0 | 3 | NT | 0 |
| C109 | 1000 | 2 | 5 | 0 | 5 | 3 | 1 |
| C110 | 1000 | 2 | 5 | 0 | 5 | 3 | 1 |
| C111 | 1000 | 2 | 5 | 1 | 5 | 4 | 0 |
| C112 | 1000 | 3 | 1 | 0 | 4 | 3 | 1 |
| C113 | 1000 | 3 | 5 | 1 | 5 | 4 | 3 |
| C114 | 1000 | 1 | 5 | 1 | 4 | 2 | 1 |
| C115 | 1000 | 1 | 5 | 0 | 4 | 2 | 0 |
| C116 | 1000 | 1 | 5 | 0 | 4 | 2 | 0 |
| C117 | 250 | 1 | 4 | 1 | 1 | 3 | 0 |
| C119 | 1000 | 3 | 5 | 1 | 5 | 4 | 3 |
| C120 | 1000 | 3 | 5 | 1 | 5 | 3 | 2 |
| C121 | 250 | 3 | 5 | 1 | 4 | 4 | 1 |

TABLE B2b

Test 2b

| Compound ID | Rate (g/ha) | LOLPE | AMARE | SETFA | ECHCG | ZEAMX | ABUTH |
|---|---|---|---|---|---|---|---|
| C9 | 1000 | 3 | 2 | 5 | 4 | 5 | 2 |
| C10 | 1000 | 3 | 1 | 4 | 4 | 5 | 1 |

The invention claimed is:

1. A compound of Formula (I)

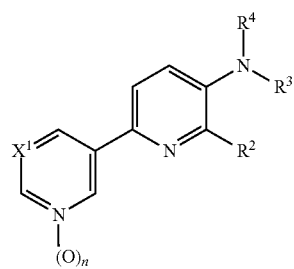

(I)

or a salt or N-oxide thereof, wherein, $X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)OC$_1$-$C_6$alkyl, —S(O)$_p$C$_1$-$C_6$alkyl, NR$^6$R$^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)OC$_1$-$C_6$alkyl, —S(O)$_p$(C$_1$-$C_6$alkyl), $C_1$-$C_6$alkoxy and $C_1$-$C_6$haloalkoxy;

$R^3$ is —C(O)R$^9$;

$R^6$ and $R^7$ are independently selected from the group consisting of hydrogen and $C_1$-$C_6$alkyl;

$R^4$ and $R^9$ together with the atoms to which they are joined form a 5-7 membered ring system containing from 1 to 3 heteroatoms, wherein at least one heteroatom is N, and any additional heteroatom is independently selected from S, O and N and wherein when said ring system comprises a ring carbon directly bonded to the nitrogen to which $R^4$ is attached, said ring carbon is optionally substituted by an oxo moiety;

n is independently 0 or 1; and p is 0, 1, or 2.

2. The compound of claim 1, wherein $X^i$ is N.

3. The compound of claim 1, wherein $X^i$ is $CR^1$ and $R^1$ is halogen or cyano.

4. The compound of claim 1, wherein $R^2$ is halogen, cyano, $C_1$-$C_6$alkyl or $C_1$-$C_6$haloalkyl.

5. The compound of claim 1, wherein the compound is selected from:

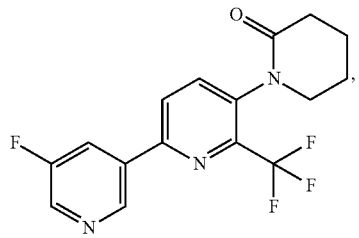

,

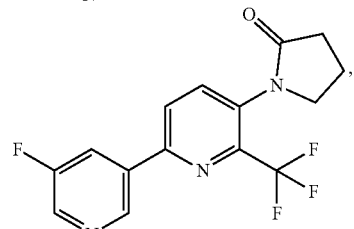

,

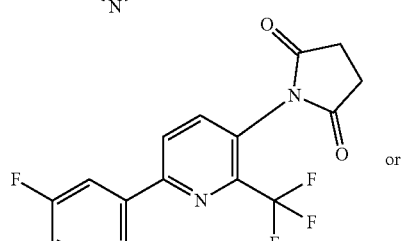

or

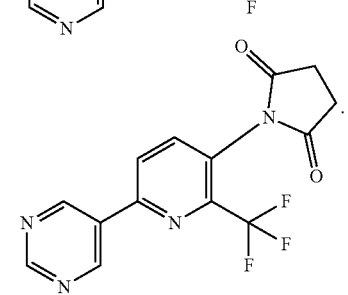

.

6. The compound of claim 1, wherein the ring system formed by $R^4$ and $R^9$ is a 5- or 6-membered heterocyclic ring system.

7. The compound of claim 1, wherein the ring system formed by $R^4$ and $R^9$ is selected from the group consisting of a pyrrolidinone, a pyrrolidinedione, and a piperidone ring.

8. The compound of claim 2, wherein $R^2$ is halogen, cyano, $C_1$-$C_6$alkyl or $C_1$-$C_6$haloalkyl.

9. The compound of claim 8, wherein the ring system formed by $R^4$ and $R^9$ is a 5- or 6-membered heterocyclic ring system.

10. The compound of claim 9, wherein the ring system formed by $R^4$ and $R^9$ is selected from the group consisting of a pyrrolidinone, a pyrrolidinedione, and a piperidone ring.

11. The compound of claim 3, wherein $R^2$ is halogen, cyano, $C_1$-$C_6$alkyl or $C_1$-$C_6$haloalkyl.

12. The compound of claim 8, wherein the ring system formed by $R^4$ and $R^9$ is a 5- or 6-membered heterocyclic ring system.

13. The compound of claim 9, wherein the ring system formed by $R^4$ and $R^9$ is selected from the group consisting of a pyrrolidinone, a pyrrolidinedione, and a piperidone ring.

14. A herbicidal composition comprising a compound of Formula (I) according to claim 1 and an agriculturally acceptable formulation adjuvant.

15. A herbicidal composition according to claim 14, further comprising at least one pesticide.

16. A herbicidal composition according to claim 15, wherein the pesticide is a herbicide or herbicide safener.

17. A method, comprising: applying to a weed or the locus of the weed a weed controlling amount of a compound of Formula (I) according to claim 1.

* * * * *

UNITED STATES PATENT AND TRADEMARK OFFICE
CERTIFICATE OF CORRECTION

| | | |
|---|---|---|
| PATENT NO. | : 11,230,538 B2 | Page 1 of 1 |
| APPLICATION NO. | : 16/087074 | |
| DATED | : January 25, 2022 | |
| INVENTOR(S) | : Carter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 217 days.

Signed and Sealed this
Eighteenth Day of February, 2025

Coke Morgan Stewart
*Acting Director of the United States Patent and Trademark Office*